(12) United States Patent
Anderson et al.

(10) Patent No.: US 6,838,262 B1
(45) Date of Patent: Jan. 4, 2005

(54) ISOLATED DNA MOLECULE ENCODING RANK LIGAND

(75) Inventors: Dirk M. Anderson, Seattle, WA (US); Laurent J. Galibert, Seattle, WA (US)

(73) Assignee: Immunex Corporation, Seattle, WA (US)

(*) Notice: Subject to any disclaimer, the term of this patent is extended or adjusted under 35 U.S.C. 154(b) by 477 days.

(21) Appl. No.: 09/688,459

(22) Filed: Oct. 13, 2000

Related U.S. Application Data

(62) Division of application No. 08/995,659, filed on Dec. 22, 1997, now Pat. No. 6,242,213.
(60) Provisional application No. 60/064,671, filed on Oct. 14, 1997, provisional application No. 60/077,181, filed on Mar. 7, 1997, and provisional application No. 60/059,978, filed on Dec. 23, 1996.

(51) Int. Cl.[7] .................. C12P 21/02; C12N 15/19; C07H 21/04; C07K 14/175
(52) U.S. Cl. .................. 435/69.7; 435/69.5; 435/6; 435/320.1; 435/252.3; 435/254.2; 435/348; 435/354; 435/366; 536/23.5; 530/351
(58) Field of Search .................. 536/23.5; 530/350; 435/69.1, 320.1, 32.5

(56) References Cited

U.S. PATENT DOCUMENTS

| | | | |
|---|---|---|---|
| 5,194,596 A | * 3/1993 | Tischer et al. | 530/399 |
| 5,350,836 A | * 9/1994 | Kopchick et al. | 530/399 |
| 5,766,223 A | 6/1998 | Wiley | |
| 5,843,678 A | 12/1998 | Boyle | |
| 6,017,729 A | 1/2000 | Anderson et al. | |
| 6,242,586 B1 | * 6/2001 | Gorman et al. | 536/23.4 |
| 6,316,408 B1 | 11/2001 | Boyle | |

FOREIGN PATENT DOCUMENTS

| | | |
|---|---|---|
| EP | 0816380 | 1/1998 |
| WO | WO 96/34095 | 10/1996 |
| WO | WO 97/23614 | 7/1997 |
| WO | WO 98/25958 | 6/1998 |
| WO | WO 98/46644 | 10/1998 |
| WO | WO 98/46751 | 10/1998 |

OTHER PUBLICATIONS

Vukicevic et al., 1996, PNAS USA 93:9021–9026.*
Anderson et al., *Nature* 390:175–79; 1997.
Boyle v. Gorman and Mattson, Board of Patent Appeals and Interferences, Interference No. 104,336, Paper No. 39.
EMBL Database entry HS 421358; Accession No. W74421, Jun. 21, 1996; Hillier et al., Homo sapiens cDNA clone 346544 contains Alu repetitive element.
Gray et al., Genetics 144(4):1601–1610, Accession AFO12089, Dec. 1996.
Lacey et al., *Cell* 93:165; 1998.
Marra et al., The WashU–HMI Mouse EST project, Accession No. AA170348, Feb. 16, 1997.
Suda et al., *Endocr. Rev.* 13:66; 1992.
Suda et al., *Bone* 17:87S; 1995.
Suda et al., in *Endocrine Review Monographs*, eds. Bikle, D.D. & Negrovilar, A. (Endocrine Soc., Bethesda), vol. 4, pp. 266–270; 1995.
Wiley et al., *Immunity* 3 (6):673–82, 1995.
Wong et al., *J. Biol. Chem.* 272 (40):25190–94, 1997.
Yasuda et al., *Proc. Natl. Acad. Sci.* 95:3597; 1998.

* cited by examiner

*Primary Examiner*—Lorraine Spector
*Assistant Examiner*—Eileen B. O'Hara
(74) *Attorney, Agent, or Firm*—Diana K. Sheiness; Patricia A. Perkins

(57) ABSTRACT

Isolated ligands, DNAs encoding such ligands, and pharmaceutical compositions made therefrom, are disclosed. The isolated ligands can be used to regulate an immune response. The ligands are also useful in screening for inhibitors thereof.

34 Claims, 2 Drawing Sheets

ISOLATED DNA MOLECULE ENCODING RANK LIGAND

CROSS-REFERENCE TO RELATED PATENT APPLICATIONS

This application is a divisional of U.S. patent application Ser. No. 08/995,659, filed Dec. 22, 1997, now U.S. Pat. No. 6,242,213, which claims benefit of priority under 35 U.S.C. §119(e) from U.S. Ser. No. 60/064,671, filed Oct. 14, 1997, U.S. Ser. No. 60/077,181, filed Mar. 7, 1997, and U.S. Ser. No. 60/059,978, filed Dec. 23, 1996.

TECHNICAL FIELD OF THE INVENTION

The present invention relates generally to the field of cytokines, and more specifically to cytokine receptor/ligand pairs having immunoregulatory activity.

BACKGROUND OF THE INVENTION

Efficient functioning of the immune system requires a fine balance between cell proliferation and differentiation and cell death, to ensure that the immune system is capable of reacting to foreign, but not self antigens. Integral to the process of regulating the immune and inflammatory response are various members of the Tumor Necrosis Factor (TNF) Receptor/Nerve Growth Factor. Receptor superfamily (Smith et al., *Science* 248:1019; 1990). This family of receptors includes two different TNF receptors (Type I and Type II; Smith et al., *supra*; and Schall et al., *Cell* 61:361, 1990), nerve growth factor receptor (Johnson et al., *Cell* 47:545, 1986), B cell antigen CD40 (Stamenkovic et al., *EMBO J.* 8:1403, 1989), CD27 (Camerini et al., *J. Immunol.* 147:3165, 1991), CD30 (Durkop et al., *Cell* 68:421, 1992), T cell antigen OX40 (Mallett et al., *EMBO J.* 9:1063, 1990), human Fas antigen (Itoh et al., *Cell* 66:233, 1991), murine 4-1BB receptor (Kwon et al., *Proc. Natl. Acad. Sci. USA* 86:1963, 1989) and a receptor referred to as Apoptois-Inducing Receptor (AIR; U.S. Ser. No. 08/720,864, filed Oct. 4, 1996).

CD40 is a receptor present on B lymphocytes, epithelial calls and some carcinoma cell lines that interacts with a ligand found on activated T cells, CD40L (U.S. Ser. No. 08/249,189, filed May 24, 1994). The interaction of this ligand/receptor pair is essential for both the cellular and humoral immune response. Signal transduction via CD40 is mediated through the association of the cytoplasmic domain of this molecule with members of the TNF receptor-associated factors (TRAFs; Baker and Reddy, *Oncogene* 12:1, 1996). It has recently been found that mice that are defective in TRAF3 expression due to a targeted disruption in the gene encoding TRAF3 appear normal at birth but develop progressive hypoglycemia and depletion of peripheral white cells, and die by about ten days of age (Xu et al., *Immunity* 5:407, 1996). The immune responses of chimeric mice reconstituted with TRAF3$^{-/-}$ fetal liver cells resemble those of CD40-deficient mice, although TRAF3$^{-/-}$ B cells appear to be functionally normal.

The critical role of TRAF3 in signal transduction may be in its interaction with one of the other members of the TNF receptor superfamily, for example, CD30 or CD27, which are present on T cells. Alternatively, there may be other, as yet unidentified members of this family of receptors that interact with TRAF3 and play an important role in postnatal development as well as in the development of a competent immune system. Identifying additional members of the TNF receptor superfamily would provide an additional means of regulating the immune and inflammatory response, as well as potentially providing further insight into post-natal development in mammals.

SUMMARY OF THE INVENTION

The present invention provides a counterstructure, or ligand, for a novel receptor referred to as RANK (for receptor activator of NF-κB), that is a member of the TNF superfamily. The ligand, which is referred to as RANKL, is a Type 2 transmembrane protein with an intracellular domain of less than about 50 amino acids, a transmembrane domain and an extracellular domain of from about 240 to 250 amino acids. Similar to other members of the TNF family to which it belongs, RANKL has a 'spacer' region between the transmembrane domain and the receptor binding domain that is not necessary for receptor binding. Accordingly, soluble forms of RANKL can comprise the entire extracellular domain or fragments thereof that include the receptor binding region.

RANK is a Type I transmembrane protein having 616 amino acid residues that is a member of the TNFR superfamily, and interacts with TRAF3. Triggering of RANK by over-expression, co-expression of RANK and membrane bound RANKL, or by soluble RANKL or agonistic antibodies to RANK, results in the upregulation of the transcription factor NF-κB, a ubiquitous transcription factor that is most extensively utilized in cells of the immune system.

These and other aspects of the present invention will become evident upon reference to the following detailed description of the invention.

DETAILED DESCRIPTION OF THE INVENTION

Figure 1:
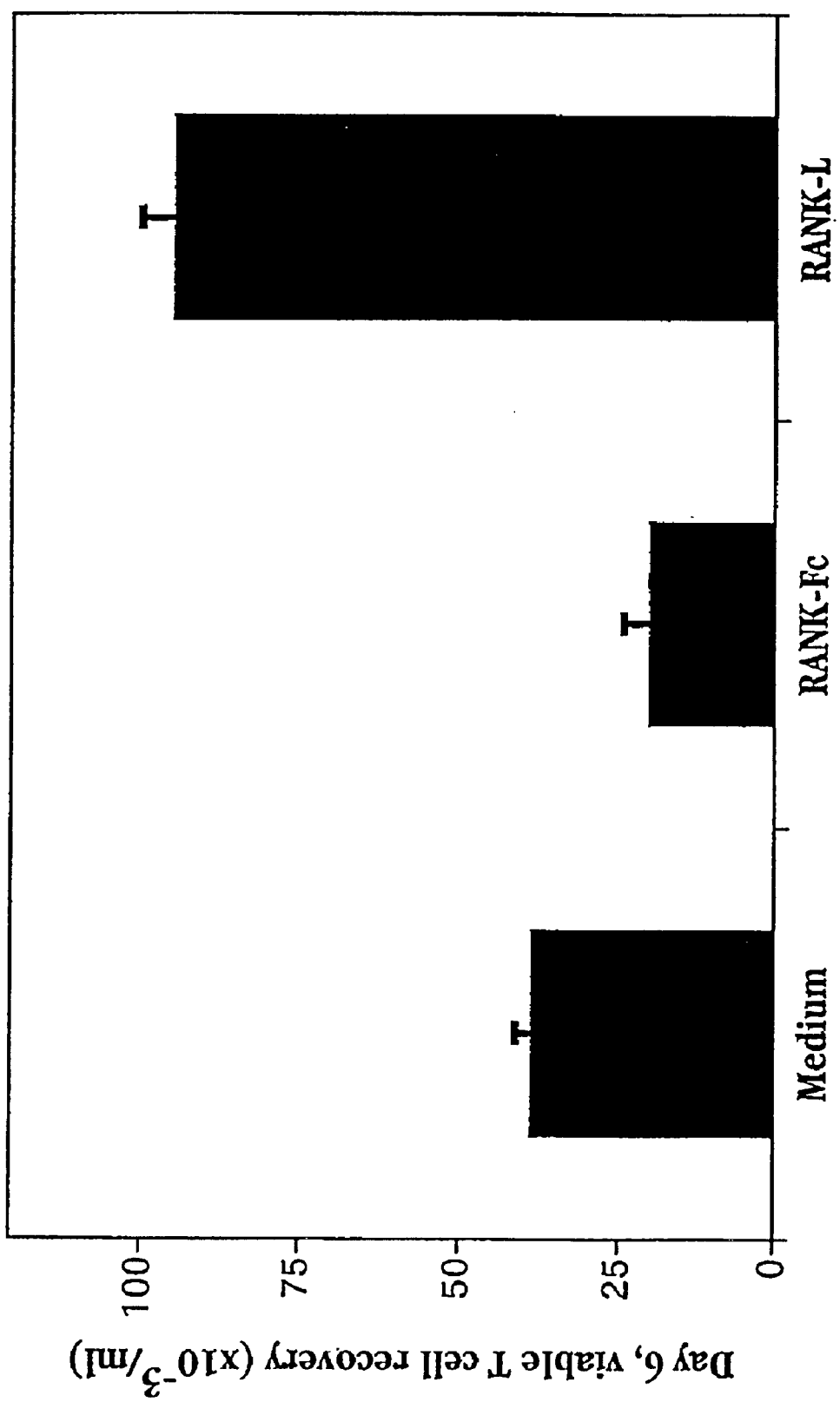
FIG. 1 demonstrates the influence of RANK.Fc and hRANKL on activated T cell growth. Human peripheral blood T cells were cultured as described in Example 12; viable T cell recovery was determined by triplicate trypan blue countings.

A novel partial cDNA insert with a predicted open reading frame having some similarity to CD40 was identified in a database containing sequence information from cDNAs generated from human bone marrow-derived dendritic cells (DC). The insert was used to hybridize to colony blots generated from a DC cDNA library containing full-length cDNAs. Several colony hybridizations were performed, and two clones (SEQ ID NOs:1 and 3) were isolated. SEQ ID NO:5 shows the nucleotide and amino acid sequence of a predicted full-length protein based on alignment of the overlapping sequences of SEQ ID NOs:1 and 3.

RANK is a member of the TNF receptor superfamily; it most closely resembles CD40 in the extracellular region. Similar to CD40, RANK associates with TRAF2,and TRAF3 (is determined by co-immunoprecipitation assays substantially as described by Rothe et al., *Cell* 83:1243, 1995). TRAFs are critically important in the regulation of the immune and inflammatory response. Through their association with various members of the TNF receptor superfamily, a signal is transduced to a cell. That signal results in the proliferation, differentiation or apoptosis of the cell, depending on which receptor(s) is/are triggered and which TRAF(s) associate with the receptor(s); different signals can be transduced to a cell via coordination of various signaling events. Thus, a signal transduced through one member of this family may be proliferative, differentiative or apoptotic, depending on other signals being transduced to the cell, and/or the state of differentiation of the cell. Such exquisite regulation of this proliferative/apoptotic pathway is necessary to develop and maintain protection against pathogens; imbalances can result in autoimmune disease.

RANK is expressed on epithelial cells, some B cell lines, and on activated T cells. However, its expression on activated T cells is late, about four days after activation. This time course of expression coincides with the expression of Fas, a known agent of apoptosis. RANK may act as an anti-apoptotic signal, rescuing cells that express RANK from apoptosis as CD40 is known to do. Alternatively, RANK may confirm an apoptotic signal under the appropriate circumstances, again similar to CD40. RANK and its ligand are likely to play an integral role in regulation of the immune and inflammatory response.

Moreover, the post-natal lethality of mice having a targeted disruption of the TRAF3 gene demonstrates the importance of this molecule not only in the immune response but in development. The isolation of RANK, as a protein that associates with TRAF3, and its ligand, RANKL, will allow further definition of this signaling pathway, and development of diagnostic and therapeutic modalities for use in the area of autoimmune and/or inflamatory disease.

DNAs, Proteins and Analogs

The present invention provides isolated RANKL polypeptides and analogs (or muteins) thereof having an activity exhibited by the native molecule (i.e, RANKL mutcins that bind specifically to a RANK expressed on cells or immobilized on a surface or to RANKL-specific antibodies; soluble forms thereof that inhibit RANK ligand-induced signaling through RANK). Such proteins are substantially free of contaminating endogenous materials and, optionally, without associated native-pattern glycosylation. Derivatives of RANKL within the scope of the invention also include various structural forms of the primary proteins which retain biological activity. Due to the presence of ionizable amino and carboxyl groups, for example a RANKL protein may be in the form of acidic or basic salts, or may be in neutral form. Individual amino acid residues may also be modified by oxidation or reduction. The primary amino acid structure may be modified by forming covalent or aggregative conjugates with other chemical moieties, such as glycosyl groups, lipids, phosphate, acetyl groups and the like, or by creating amino acid sequence mutants. Covalent derivatives are prepared by linking particular functional groups to amino acid side chains or at the N- or C-termini.

Derivatives of RANKL may also be obtained by the action of cross-linking agents, such as M-maleimidobenzoyl succinimide ester and N-hydroxysuccinimide, at cysteine and lysine residues. The inventive proteins may also be covalently bound through reactive side groups to various insoluble substrates, such as cyanogen bromide-activated, bisoxirane-activated, carbonyldiimidazole-activated or tosyl-activated agarose structures, or by adsorbing to polyolefin surfaces (with or without glutaraldehyde cross-linking). Once bound to a substrate, the proteins may be used to selectively bind (for purposes of assay or purification) antibodies raised against the proteins or against other proteins which are similar to RANKL, as well as other proteins that bind RANKL or homologs thereof.

Soluble forms of RANKL are also within the scope of the invention. The nucleotide and predicted amino acid sequence of the RANKL is shown in SEQ ID NOs:10 and 12 (murine and human, respectively). Computer analysis indicated that the RANKL is a Type 2 transmembrane protein; murine RANKL contains a predicted 48 amino acid intracellular domain, 21 amino acid transmembrane domain and 247 amino acid extracellular domain, and human RANKL contains a predicted 47 amino acid intracellular domain, 21 amino acid transmembrane domain and 249 amino acid extracellular domain.

Soluble RANKL comprises a signal peptide and the extracellular domain or a fragment thereof. An exemplary signal peptide is that shown in SEQ ID NO:9; other signal (or leader) peptides are well-known in the art, and include that of murine Interleukin-7 or human growth hormone. RANKL is similar to other members of the TNF family in having a region of amino acids between the transmembrane domain and the receptor binding region that does not appear to be required for biological activity; this is referred to as a 'spacer' region. Amino acid sequence alignment indicates that the receptor binding region is from about amino acid 162 of human RANKL to about amino acid 317 (corresponding to amino acid 139 through 294 of murine RANKL, SEQ ID NO:11), beginning with an Ala residue that is conserved among many members of the family (amino acid 162 of SEQ ID NO: 13).

Moreover, fragments of the extracellular domain will also provide soluble forms of RANKL. Those skilled in the art will recognize that the actual receptor binding region may be different than that predicted by computer analysis. Thus, the N-terminal amino acid of a soluble RANKL is expected to be within about five amino acids on either side of the conserved Ala residue. Alternatively, all or a portion of the spacer region may be included at the N-terminus of a soluble RANKL, as may be all or a portion of the transmembrane and/or intracellular domains, provided that the resulting soluble RANKL is not membrane-associated. Accordingly, a soluble RANKL will have an N-terminal amino acid selected from the group consisting of amino acids 1 through 162 of SEQ ID NO:13 (1 through 139 of SEQ ID NO:11). Preferably, the amino terminal amino acid is between amino acids 69 and 162 of SEQ ID NO:13 (human RANKL; amino acids 48 and 139 of SEQ ID NO:11). Similarly, the carboxy terminal amino acid can be between amino acid 313 and 317 of SEQ ID NO:13 (human RANKL; corresponding to amino acids 290 through 294 of SEQ ID NO: 11). Those skilled in the art can prepare these and additional soluble forms through routine experimentation.

Fragments can be prepared using known techniques to isolate a desired portion of the extracellular region, and can be prepared, for example, by comparing the extracellular region with those of other members of the TNF family (of which RANKL is a member) and selecting forms similar to those prepared for other family members. Alternatively, unique restriction sites or PCR techniques that are known in the art can be used to prepare numerous truncated forms which can be expressed and analyzed for activity.

Other derivatives of the RANKL proteins within the scope of this invention include covalent or aggregative conjugates of the proteins or their fragments with other proteins or polypeptides, such as by synthesis in recombinant culture as N-terminal or C-terminal fusions. For example, the conjugated peptide may be a signal (or leader) polypeptide sequence at the N-terminal region of the protein which co-translationally or post-translationally directs transfer of the protein from its site of synthesis to its site of function inside or outside of the cell membrane or wall (e.g., the yeast α-factor leader).

Protein fusions can comprise peptides added to facilitate purification or identification of RANKL proteins and homologs (e.g., poly-His). The amino acid sequence of the inventive proteins can also be linked to an identification peptide such as that described by Hopp et al., *Bio/Technology* 6:1204 (1988). Such a highly antigenic peptide provides an epitope reversibly bound by a specific monoclonal antibody, enabling rapid assay and facile purification of expressed recombinant protein. The sequence of Hopp et al. is also specifically cleaved by bovine mucosal enterokinase, allowing removal of the peptide from the purified protein. Fusion proteins capped with such peptides may also be resistant to intracellular degradation in *E. coli*.

Fusion proteins further comprise the amino acid sequence of a RANKL linked to an immunoglobulin Fc region. An exemplary Fc region is a human $IgG_1$ having a nucleotide an amino acid sequence set forth in SEQ ID NO:8. Fragments of an Fc region may also be used, as can Fe muteins. For example, certain residues within the hinges region of an Fc region are critical for high affinity binding to FcγRI. Canfield and Morrison (*J. Exp. Med.* 173:1483; 1991) reported that $Leu_{(234)}$ and $Leu_{(235)}$ were critical to high affinity binding of $IgG_3$ to FcγRI present on U937 cells. Similar results were obtained by Lund et al. (*J. Immunol.* 147:2657, 1991; *Molecular Immunol.* 29:53, 1991). Such mutations, alone or in combination, can be made in an $IgG_1$ Fc region to decrease the affinity of $IgG_1$ for FcR. Depending on the portion of the Fc region used, a fusion protein may be expressed as a dimer, through formation of interchain disulfide bonds. If the fusion proteins are made with both heavy and light chains of an antibody, it is possible to form a protein oligomer with as many as four RANKL regions.

In another embodiment, RANKL proteins further comprise an oligomerizing peptide such as a leucine zipper domain. Leucine zippers were originally identified in several DNA-binding proteins (Landschulz et al., *Science* 240:1759, 1988). Leucine zipper domain is a term used to refer to a conserved peptide domain present in these (and other) proteins, which is responsible for dimerization of the proteins. The leucine zipper domain (also referred to herein as an oligomerizing, or oligomer-forming, domain) comprises a repetitive heptad repeat, with four or five leucine residues interspersed with other amino acids. Examples of leucine zipper domains are those found in the yeast transcription factor GCN4 and a heat-stable DNA-binding protein found in rat liver (C/EBP; Landschulz et al., *Science* 243:1681, 1989). Two nuclear transforming proteins, fos and jun, also exhibit leucine zipper domains, as does the gene product of the murine proto-oncogene, c-myc (Landschulz et al., *Science* 240:1759, 1988). The products of the nuclear oncogenes fos and jun comprise leucine zipper domains preferentially form a heterodimer (O'Shea et al., *Science* 245:646, 1989; Turner and Tjian, *Science* 243:1689, 1989). The leucine zipper domain is necessary for biological activity (DNA binding) in these proteins.

The fusogenic proteins of several different viruses, including paramyxovirus, coronavirus, measles virus and many retroviruses, also possess leucine zipper domains (Buckland and Wild, *Nature* 338:547,1989; Britton, *Nature* 353:394, 1991; Delwart and Mosialos, *AIDS Research and Human retroviruses* 6:703, 1990). The leucine zipper domains in these fusogenic viral proteins are near the transmembrane region of the proteins; it has been suggested that the leucine zipper domains could contribute to the oligomeric structure of the fusogenic proteins. Oligomerization of fusogenic viral proteins is involved in fusion pore formation (Spruce et al, *Proc. Natl. Acad. Sci. U.S.A.* 88:3523, 1991). Leucine zipper domains have also been recently reported to play a role in oligomerization of heat-shock transcription factors (Rabindran et al., *Science* 259:230, 1993).

Leucine zipper domains fold as short, parallel coiled coils. (O'Shea et al., *Science* 254:539; 1991). The general architecture of the parallel coiled coil has been well characterized, with a "knobs-into-holes" packing as proposed by Crick in 1953 (*Acta Crystallogr.* 6:689). The dimer formed by a leucine zipper domain is stabilized by the heptad repeat, designated $(abcdefg)_n$ according to the notation of McLachlan and Stewart (*J. Mol. Biol.* 98:293; 1975), in which residues a and d are generally hydrophobic residues, with d being a leucine, which line up on the same face of a helix. Oppositely-charged residues commonly occur at positions g and e. Thus, in a parallel coiled coil formed from two helical leucine zipper domains, the "knobs" formed by the hydrophobic side chains of the first helix are packed into the "holes" formed between the side chains of the second helix.

The leucine residues at position d contribute large hydrophobic stabilization energies, and are important for dimer formation (Krystek et al., Int. *J. Peptide Res.* 38:229, 1991). Lovejoy et al. recently reported the synthesis of a triple-stranded α-helical bundle in which the helices run up-updown (*Science* 259:1288, 1993). Their studies confirmed that hydrophobic stabilization energy provides the main driving force for the formation of coiled coils from helical monomers. These studies also indicate that electrostatic interactions contribute to the stoichiometry and geometry of coiled coils.

Several studies have indicated that conservative amino acids may be substituted for individual leucine residues with minimal decrease in the ability to dimerize; multiple changes, however, usually result in loss of this ability (Landschulz et al., *Science* 243:1681, 1989; Turner and Tjian, *Science* 243:1689, 1989; Hu et al., *Science* 250:1400, 1990). van Heekeren et al. reported that a number of different amino residues can be substituted for the leucine residues in the leucine zipper domain of GCN4, and further found that some GCN4 proteins containing two leucine substitutions were weakly active (*Nucl. Acids Res.* 20:3721, 1992). Mutation of the first and second heptadic leucines of the leucine zipper domain of the measles virus fusion protein (MVF) did not affect syncytium formation (a measure of virally-induced cell fusion); however, mutation of all four leucine residues prevented fusion completely (Buckland et al., *J. Gen. Virol.* 73:1703, 1992). None of the mutations affected the ability of MVF to form a tetramer.

Amino acid substitutions in the a and d residues of a synthetic peptide representing the GCN4 leucine zipper domain have been found to change the oligomerization properties of the leucine zipper domain (Alber, Sixth Symposium of the Protein Society, San Diego, Calif.). When all residues at position a are changed to isoleucine, the leucine zipper still forms a parallel dimer. When, in addition to this change, all leucine residues at position d are also changed to isoleucine, the resultant peptide spontaneously forms a trimeric parallel coiled coil in solution. Substituting all amino acids at position d with isoleucine and at position a with leucine results in a peptide that tetramerizes. Peptides containing these substitutions are still referred to as leucine zipper domains.

The present invention also includes RANKL with or without associated native-pattern glycosylation. Proteins expressed in yeast or mammalian expression systems, e,g., COS-7 cells, may be similar or slightly different in molecular weight and glycosylation pattern than the native molecules, depending upon the expression system. Expression of DNAs encoding the inventive proteins in bacteria such as $E.$ $coli$ provides non-glycosylated molecules. Functional mutant analogs of RANKL protein having inactivated N-glycosylation sites can be produced by oligonucleotide synthesis and ligation or by site-specific mutagenesis techniques. These analog proteins can be produced in a homogeneous, reduced-carbohydrate form in good yield using yeast expression systems. N-glycosylation sites in eukaryotic proteins are characterized by the amino acid triplet Asn-$A_1$-Z, where $A_1$ is any amino acid except Pro, and Z is Ser or Thr. In this sequence, asparagine provides a side chain amino group for covalent attachment of carbohydrate. Such a site can be eliminated by substituting another amino acid for Asn or for residue Z, deleting Asn or Z, or inserting a non-Z amino acid between $A_1$ and Z, or an amino acid other than Asn between Asn and $A_1$.

RANKL protein derivatives may also be obtained by mutations of the native RANKL or subunits thereof. A RANKL mutated protein, as referred to herein, is a polypeptide homologous to a native RANKL protein, but which has an amino acid sequence different from the native protein because of one or a plurality of deletions, insertions or substitutions. The effect of any mutation made in a DNA encoding a mutated peptide may be easily determined by analyzing the ability of the mutated peptide to bind its counterstructure in a specific manner. Moreover, activity of RANKL analogs, muteins or derivatives can be determined by any of the assays described herein (for example, induction of NF-κB activation).

Analogs of the inventive proteins may be constructed by, for example, making various substitutions of residues or sequences or deleting terminal or internal residues or sequences not needed for biological activity. For example, cysteine residues can be deleted or replaced with other amino acids to prevent formation of incorrect intramolecular disulfide bridges upon renaturation. Other approaches to mutagenesis involve modification of adjacent dibasic amino acid residues to enhance expression in yeast systems in which KEX2 protease activity is present.

When a deletion or insertion strategy is adopted, the potential effect of the deletion or insertion on biological activity should be considered. Subunits of the inventive proteins may be constructed by deleting terminal or internal residues or sequences. Soluble forms of RANKL can be readily prepared and tested for their ability to induce NF-κB activation. Polypeptides corresponding to the cytoplasmic regions, and fragments thereof (for example, a death domain) can be prepared by similar techniques. Additional guidance as to the type of mutation that can be made is provided by a comparison of the sequence of RANKL to proteins that have similar structures, as well as by performing structural analysis of the inventive RANKL protein.

Generally, substitution should be made conservatively; i.e., the most preferred substitute amino acids are those which do not affect the biological activity of RANKL (i.e., ability of the inventive proteins to bind antibodies to the corresponding native protein in substantially equivalent a manner, the ability to bind the counterstructure in substantially the same manner as the native protein, the ability to induce a RANKL signal, or ability to induce NF-κB activation). Examples of conservative substitutions include substitution of amino acids outside of the binding domain(s) (either ligand/receptor or antibody binding areas for the extracellular domain, or regions that interact with other, intracellular proteins for the cytoplasmic domain), and substitution of amino acids that do not alter the secondary and/or tertiary structure of the native protein. Additional examples include substituting one aliphatic residue for another, such as Ile, Val, Leu, or Ala for one another, or substitutions of one polar residue for another, such as between Lys and Arg; Glu and Asp; or Gln and Asn. Other such conservative substitutions, for example, substitutions of entire regions having similar hydrophobicity characteristics, are well known.

Mutations in nucleotide sequences constructed for expression of analog proteins or fragments thereof must, of course, preserve the reading frame phase of the coding sequences and preferably will not create complementary regions that could hybridize to produce secondary mRNA structures such as loops or hairpins which would adversely affect translation of the mRNA.

Not all mutations in the nucleotide sequence which encodes a RANKL protein or fragments thereof will be expressed in the final product, for example, nucleotide substitutions may be made to enhance expression, primarily to avoid secondary structure loops in the transcribed mRNA (see EPA 75,444A, incorporated herein by reference), or to provide codons that are more readily translated by the selected host, e.g., the well-known $E.$ $coli$ preference codons for $E.$ $coli$ expression.

Although a mutation site may be predetermined, it is not necessary that the nature of the mutation per se be predetermined. For example, in order to select for optimum characteristics of mutants, random mutagenesis may be conducted and the expressed mutated proteins screened for the desired activity. Mutations can be introduced at particular loci by synthesizing oligonucleotides containing a mutant sequence, flanked by restriction sites enabling ligation to fragments of the native sequence. Following ligation, the resulting reconstructed sequence encodes an analog having the desired amino acid insertion, substitution, or deletion.

Alternatively, oligonucleotide-directed site-specific mutagenesis procedures can be employed to provide in alerted gene having particular codons alerted according to the substitution, deletion, or insertion required. Exemplary methods of making the alterations set forth above are disclosed by Walder et al. (*Gene* 42:133, 1986); Bauer et al. (*Gene* 37:73, 1985); Craik (*BioTechniques*, January 1985, 12–19); Smith et al. (*Genetic Engineering: Principles and Methods*, Plenum Press, 1981); and U.S. Pat. Nos. 4,518,584 and 4,737,462 disclose suitable techniques, and are incorporated by reference herein.

Additional embodiments of the inventive proteins include RANKL polypeptides encoded by DNAs capable of hybridizing to the DNAS of SEQ ID NO:10 or 12 under moderately stringent conditions (prewashing solution of 5×SSC, 0.5% SDS, 1.0 mM EDTA (pH 8.0) and hybridization conditions of 50° C., 5×SSC, overnight) to the DNA sequences encoding RANKL, or more preferably under stringent conditions (for example, sequences which are degenerate to those which encode the RANKL. In one embodiment, RANKL polypeptides are at least about 70% identical in amino acid sequence to the amino acid sequence of native RANKL protein as set forth in SEQ ID NOs:10 and 12. In a preferred embodiment, RANKL polypeptides are at least about 80% identical in amino acid sequence to the native form of RANKL; most preferred polypeptides are those that are at least about 90% identical to native RANKL.

Percent identity may be determined using a computer program, for example, the GAP computer program described by Devereux et al. (*Nucl. Acids Res.* 12:387, 1984) and available from the University of Wisconsin Genetics Computer Group (UWGCG). For fragments derived from the RANKL protein, the identity is calculated based on that portion of the RANKL protein that is present in the fragment The biological activity of RANKL analogs or muteins can be determined by testing the ability of the analogs or muteins to induce a signal through RANK, for example, activation of transcription as described in the Examples herein Alternatively, suitable assays, for example, an enzyme immunoassay or a dot blot, employing an antibody that binds native RANKL, or a soluble form of RANK, can be used to assess the activity of RANKL analogs or muteins. Suitable assays also include, for example, assays that measure the ability of a RANKL peptide or mutein to bind cells expressing RANK, and/or the biological effects thereon. Such methods are well known in the art.

Fragments of the RANKL nucleotide sequences are also useful. In one embodiment, such fragments comprise at least about 17 consecutive nucleotides, preferably at least about 25 nucleotides, more preferably at least 30 consecutive nucleotides, of the RANKL DNA disclosed herein. DNA and RNA complements of such fragments arc provided herein, along with both single-stranded and double-stranded forms of the RANKL DNAs of SEQ ID NOs:10 and 12, and those encoding the aforementioned polypeptides. A fragment of RANKL DNA generally comprises at least about 17 nucleotides, preferably from about 17 to about 30 nucleotides. Such nucleic acid fragments (for example, a probe corresponding to the extracellular domain of RANKL) are used as a probe or as primers in a polylmerase chain reaction (PCR).

The probes also find use in detecting the presence of RANKL nucleic acids in in vitro assays and in such procedures as Northern and Southern blots. Cell types expressing RANKL can be identified as well. Such procedures are well known, and the skilled artisan can choose a probe of suitable length, depending on the particular intended application. For PCR, 5' and 3' primers corresponding to the termini of a desired RANKL DNA sequence are employed to amplify that sequence, using conventional techniques.

Other useful fragments of the RANKL nucleic acids are antisense or sense oligonucleotides comprising a single-stranded nucleic acid sequence (either RNA or DNA) capable of binding to target RANKL mRNA (sense) or RANKL DNA (antisense) sequences. The ability to create an antisense or a sense oligonucleotide, based upon a cDNA sequence for a given protein is described in, for example, Stein and Cohen, *Cancer Res.* 48:2659, 1988 and van der Krol et al., *BioTechniques* 6:958, 1988.

Uses of DNAs. Proteins and Analogs

The RANKL DNAs, proteins and analogs described herein will have numerous uses, including the preparation of pharmaceutical compositions. For example, soluble forms of RANKL will be useful to transduce signal via RANK. RANKL compositions (both protein and DNAs) will also be useful in development of antibodies to RANKL, both those that inhibit binding to RANK and those that do not. The inventive DNAs are useful for the expression of recombinant proteins, and as probes for analysis (either quantitative or qualitative) of the presence or distribution of RANKL transcripts.

The inventive proteins will also be useful in preparing kits that are used to detect soluble RANK or RANKL, or monitor RANK-related activity, for example, in patient specimens. RANKL proteins will also find uses in monitoring RANK-related activity in other samples or compositions, as is necessary when screening for antagonists or mimetics of this activity (for example, peptides or small molecules that inhibit or mimic, respectively, the interaction). A variety of assay formats are useful in such kits, including (but not limited to) ELISA, dot blot, solid phase binding assays (such as those using a biosensor), rapid format assays and bioassays.

The purified RANKL according to the invention will facilitate the discovery of inhibitors of RANK, and thus, inhibitors of an inflammatory response (via inhibition of NF-κB activation). The use of a purified RANKL polypeptide in the screening for potential inhibitors is important and can virtually eliminate the possibility of interfering reactions with contaminants. Such a screening assay can utilize either the extracellular domain of RANKL, or a fragment thereof. Detecting the inhibiting activity of a molecule would typically involve use of a soluble form of RANKL derived from the extracellular domain in a screening assay to detect molecules capable of binding RANK and inhibiting binding of the RANKL.

In addition, RANKL polypeptides can also be used for structure-based design of RANKL-inhibitors. Such structure-based design is also known as "rational drug design." The RANKL polypeptides can be three-dimensionally analyzed by, for example, X-ray crystallography, nuclear magnetic resonance or homology modeling, all of which are well-known methods. The use of RANKL structural information in molecular modeling software systems to assist in inhibitor design is also encompassed by the invention. Such computer-assisted modeling and drug design may utilize information such as chemical conformational analysis, electrostatic potential of the molecules, protein folding, etc. A particular method of the invention comprises analyzing the three dimensional structure of RANKL for likely binding sites of substrates, synthesizing a new molecule that incorporates a predictive reactive site, and assaying the new molecule as described above.

Moreover, as shown in the Examples herein, soluble forms of RANKL will be useful to induce maturation of dendritic cells (DC), and to enhance their allo-stimulatory capacity. Accordingly, RANKL proteins will be useful in augmenting an immune response, and can be used for these purposes either ex vivo (i.e., in obtaining cells such as DC from an individual, exposing them to antigen and cytokines ex vivo, and re-administering them to the individual) or in vivo (i.e., as a vaccine adjuvant that will augment humoral and/or cellular immunity). RANKL will also be useful promoting viability of T cells in the presence of TGFβ, which will also be helpful in regulating an immune response.

Expression of Recombinant RANKL

The proteins of the present invention are preferably produced by recombinant DNA methods by inserting a DNA sequence encoding RANKL protein or an analog thereof into a recombinant expression vector and expressing the DNA sequence in a recombinant expression system under conditions promoting expression. DNA sequences encoding the proteins provided by this invention can be assembled from cDNA fragments and short oligonucleotide linkers, or from a series of oligonucleotides, to provide a synthetic gene which is capable of being inserted in a recombinant expression vector and expressed in a recombinant transcriptional unit.

Recombinant expression vectors include synthetic or cDNA-derived DNA fragments encoding RANKL, or homologs, muteins or bioequivalent analogs thereof, operably linked to suitable transcriptional or translational regulatory elements derived from mammalian, microbial, viral or insect genes. Such regulatory elements include a transcriptional promoter, an optional operator sequence to control transcription, a sequence encoding suitable mRNA ribosomal binding sites, and sequence which control the termination of transcription and translation, as described in detail below. The ability to replicate in a host, usually conferred by an origin of replication, and a selection gene to facilitate recognition of transformants may additionally be incorporated.

DNA regions are operably linked when they are functionally related to each other. For example, DNA for a signal peptide (secretory leader) is operably linked to DNA for a polypeptide if it is expressed as a precursor which participates in the secretion of the polypeptide; a promoter is operably linked to a coding sequence if it controls the transcription of the sequence; or a ribosome binding site is operably linked to a coding sequence if it is positioned so as to permit translation. Generally, operably linked means contiguous and, in the case of secretory leaders, contiguous and in reading frame. DNA sequences encoding RANKL, or homologs or analogs thereof which are to be expressed in a microorganism will preferably contain no introns that could prematurely terminate transcription of DNA into mRNA.

Useful expression vectors for bacterial use can comprise a selectable marker and bacterial origin of replication derived from commercially available plasmids comprising genetic elements of the well known cloning vector pBR322 (ATCC 37017). Such commercial vectors include, for example, pKK223-3 (Pharmacia Fine Chemicals, Uppsala, Sweden) and pGEM1 (Promega Biotec, Madison, Wis., USA). These pBR322 "backbone" sections are combined with an appropriate promoter and the structural sequence to be expressed. *E. coli* is typically transformed using derivatives of pBR322, a plasmid derived from an *E. coli* species (Bolivar et al., *Gene* 2:95, 1977). pBR322 contains genes for ampicillin and tetracycline resistance and thus provides simple means for identifying transformed cells.

Promoters commonly used in recombinant microbial expression vectors include the β-lactamase (penicillinase) and lactose promoter system (Chang et al., *Nature* 275:615, 1978; and Goeddel et al., *Nature* 281:544, 1979), the tryptophan (trp) promoter system (Goeddel et al., *Nucl. Acids Res.* 8:4057, 1980; and EPA 36,776) and tac promoter (Maniatis, *Molecular Cloning: A Laboratory Manual*, Cold Spring Harbor Laboratory, p. 412, 1982). A particularly useful bacterial expression system employs the phage λ $P_L$ promoter and cI857ts thermolabile repressor. Plasmid vectors available from the American Type Culture Collection which incorporate derivatives of the λ $P_L$ promoter include plasmid pHUB2, resident in *E. coli* strain JMB9 (ATCC 37092) and pPLc28, resident in *E. coli* RR1 (ATCC 53082).

Suitable promoter sequences in yeast vectors include the promoters for metallothionein, 3-phosphoglycerate kinase (Hitzeman et al., *J. Biol.* 25:2073, 1980) or other glycolytic enzymes (Hess et al., *J. Adv. Enzyme Reg.* 7.149, 1968; and Holland et al., *Biochem.* 17:4900, 1978), such as enolase, glyceraldehydes-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isometrase, and glucokinase. Suitable vectors and promoters for use in yeast expression are further described in R: Hitzeman et al., EPA 73,657.

Preferred yeast vectors can be assembled using DNA sequences from pBR322 for selection and replication in *E. coli* (Amp$^r$ gene and origin of replication) and yeast DNA sequences including a glucose-repressible ADH2 promoter and α-factor secretion leader. The ADH2 promoter has been described by Russell et al. (*J. Biol. Chem.* 258:2674, 1982) and Beier et al. (*Nature* 300:724, 1982). The yeast α-factor leader, which directs secretion of heterologous proteins, can be inserted between the promoter and the structural gene to be expressed. See, e.g., Kuijan et al., *Cell* 30:933, 1982; and Bitter et al., *Proc. Natl. Acad. Sci. USA* 81:5330, 1984. The leader sequence may be modified to contain, near its 3' end, one or more useful restriction sites to facilitate fusion of the leader sequence to foreign genes.

The transcriptional and translational control sequences in expression vectors to be used in transforming vertebrate cells may be provided by viral sources. For example, commonly used promoters and enhancers are derived from Polyoma, Adenovirus 2, Simian Virus 40 (SV40), and human cytomegalovirus. DNA sequences derived from the SV40 viral genome, for example, SV40 origin, early and late promoter, enhancer, splice, and polyadenylation sites may be used to provide the other genetic elements required for expression of a heterologous DNA sequence. The early and late promoters are particularly useful because both are obtained easily from the virus as a fragment which also contains the SV40 viral origin of replication (Fiers et al., *Nature* 273:113, 1978). Smaller or larger SV40 fragments may also be used, provided the approximately 250 bp sequence extending from the Hind III site toward the BglI site located in the viral origin of replication is included. Further, viral genomic promoter, control and/or signal sequences may be utilized, provided such control sequences are compatible with the host cell chosen. Exemplary vectors can be constructed as disclosed by Okayama and Berg (*Mol. Cell. Biol.* 3:280, 1983).

A useful system for stable high level expression of mammalian receptor cDNAs in C127 murine mammary epithelial cells can be constructed substantially as described by Cosman et al. (*Mol. Immunol.* 23:935, 1986). A preferred eukaryotic vector for expression of RANKL DNA is referred to as pDC406 (McMahan et al., *EMBO J.* 10:2821, 1991), and includes regulatory sequences derived from SV40, human immunodeficiency virus (HIV), and Epstein-Barr virus (EBV). Other preferred vectors include pDC409 and pDC410, which are derived from pDC406. pDC410 was derived from pDC406 by substituting the EBV origin of replication with sequences encoding the SV40 large T antigen. pDC409 differs from pDC406 in that a Bgl II restriction site outside of the multiple cloning site has been detected, making the Bgl II site within the multiple cloning site unique.

A useful cell line that allows for episomal replication of expression vectors, such as pDC406 and pDC409, which contain the EBV origin of replication, is CV-1/EBNA (ATCC CRL 10478). The CV-1/EBNA cell line was derived by transfection of the CV-1 cell line with a gene encoding Epstein-Barr virus nuclear antigen-1 (EBNA-1) and constitutively express EBNA-1 driven from human CMV immediate-early enhancer/promoter.

Host Cells

Transformed host cells are cells which have been transformed or taansfected with expression vectors constructed using recombinant DNA techniques and which contain sequences encoding the proteins of the present invention. Transformed host cells may express the desired protein (RANKL, or homologs or analogs thereof), but host cells transformed for purposes of cloning or amplifying the inventive DNA do not need to express the protein. Expressed proteins will preferably be secreted into the culture supernatant, depending on the DNA selected, but may be deposited in the cell membrane.

Suitable host cells for expression of proteins include prokaaryotes, yeast or higher eukaryotic cells under the control of appropriate promoters. Prokaryotes include gram negative or gram positive organisms, for example *E. coli* or Bacillus spp. Higher eukaryotic cells include established cell lines of mammalian origin as described below. Cell-free translation systems could also be employed to produce proteins using RNAs derived from the DNA constructs disclosed herein. Appropriate cloning and expression vectors for use with bacterial, fungal, yeast, and mammalian cellular hosts are described by Pouwels et al. (*Cloning Vectors: A Laboratory Manual*, Elsevier, N.Y., 1985), the relevant disclosure of which is hereby incorporated by reference.

Prokaryotic expression hosts may be used for expression of RANKL, or homologs or analogs thereof that do not require extensive proteolytic and disulfide processing. Prokaryotic expression vectors generally comprise one or more phenotypic selectable markers, for example a gene encoding proteins conferring antibiotic resistance or supplying an autotrophic requirement, and an origin of replication recognized by the host to ensure amplification within the host. Suitable prokaryotic hosts for transformation include *E. coli, Bacillus subtilis, Salmonella typhimurium*, and various species within the genera Pseudomzonas, Streplomyces, and Staphylococcus, although others may also be employed as a matter of choice.

Recombinant RANKL may also be expressed in yeast hosts, preferably from the Saccharomyces species, such as *S. cerevisiae*. Yeast of other genera, such as Pichia or Kluyveromyces may also be employed. Yeast vector will generally contain an origin of replication from the 2u yeast plasmid or an autonomously replicating sequence (ARS), promoter. DNA encoding, the protein, sequences for polyadenylation and transcription termination and a selection gene. Preferably, yeast vectors will include an origin of replication and selectable marker permiting transformation of both yeast and *E. coli*, e.g., the ampicillin resistance gene of *E. coli* and *S. cerevisiae* trp1 gene, which provides a selection marker for a mutant strain of yeast lacking the ability to grow in tryptophan, and a promoter derived from a highly expressed yeast gene to induce transcription of a structural sequence downstream. The presence of the trp1 lesion in the yeast host cell genome then provides an effective environment for detecting transformation by growth in the absence of tryptophan.

Suitable yeast transformation protocols are known to those of skill in the art; an exemplary technique is described by Hinnen et al., *Proc. Natl. Acad. Sci. USA* 75:1929, 1978, selecting for Trp$^+$ transformants in a selective medium consisting of 0.67% yeast nitrogen base, 0.5% casamino acids, 2% glucose, 10 μg/ml adenine and 20 μg/ml uracil. Host strains transformed by vectors comprising the ADH2 promoter may be grown for expression in a rich medium consisting of 1% yeast extract, 2% peptone, and 1% glucose supplemented with 80 μg/ml adenine and 80 μg/ml uracil. Depression of the ADH2 promoter occurs upon exhaustion of medium glucose. Crude yeast supernatants are harvested by filtration and held at 4° C. prior to further purification.

Various mammalian or insect cell culture systems can be employed to express recombinant protein. Baculovirus systems for production of heterologous proteins in insect cells are reviewed by Luckow and Summers, *Bio/Technology* 6:47 (1988). Examples of suitable mammalian host cell lines include the COS-7 lines of monkey kidney cells, described by Gluzman (*Cell* 23:175, 1981), and other cell lines capable of expressing an appropriate vector including, for example, CV-1/EBNA (ATCC CRL 10478), L cells, C127, 3T3, Chinese hamster ovary (CHO), HeLa and BHK cell lines. Mammalian expression vectors may comprise nontranscribed elements such as an origin of replication, a suitable promoter and enhancer linked to the gene to be expressed, and other 5' or 3' flanking nontranscribed sequences, and 5' or 3' nontranslated sequences, such as necessary ribosome binding sites, a polyadenylation site, splice donor and acceptor sites, and transcriptional termination sequences.

Purification of Recombinant RANKL

Purified RANKL, and homologs or analogs thereof are prepared by culturing suitable host/vector systems to express the recombinant translation products of the DNAs of the present invention, which are then purified from culture media or cell extracts. For example, supernatants from systems which secrete recombinant protein into culture media can be first concentrated using a commercially available protein concentration filter, for example, an Amicon or Millipore Pellicon ultrafiltration unit.

Following, the concentration step, the concentrate can be applied to a suitable purificatioin matrix. For example, a suitable affinity matrix can comprise a counter structure protein or lectin or antibody molecule bound to a suitable support. Alternatively, an anion exchange resin can be employed, for example, a matrix or substrate having pendant diethylaminoethyl (DEAE) groups. The matrices can be acrylamide, agarose, dextran, cellulose or other types commonly employed in protein purification. Alternatively, a cation exchange step can be employed. Suitable cation exchangers include various insoluble matrices comprising sulfopropyl or carboxymethyl groups. Sulfopropyl groups are preferred. Gel filtration chromatography also provides a means of purifying the inventive proteins.

Affinity chromatography is a particularly preferred method of purifying RANKL and homologs thereof. For example, a RANKL expressed as a fusion protein comprising an immunoglobulin Fc region can be purified using Protein A or Protein G affinity chromatography. Moreover, a RANKL protein comprising an oligomerizing zipper domain may be purified on a resin comprising an antibody specific to the oligomerizing zipper domain. Monoclonal antibodies against the RANKL protein may also be useful in affinity chromatography purification, by utilizing methods that are well-known in the art. A ligand may also be used to prepare an affinity matrix for affinity purification of RANKL.

Finally, one or more reversed-phase high performance liquid chromatography (RP-HPLC) steps employing hydrophobic RP-HPLC media, e.g., silica gel having pendant methyl or other aliphatic groups, can be employed to further purify a RANKL composition. Some or all of the foregoing purification steps, in various combinations, can also be employed to provide a homogeneous recombinant protein.

Recombinant protein produced in bacterial culture is usually isolated by initial extraction from cell pellets, followed by one or more concentration, salting-out, aqueous ion exchange or size exclusion chromatography steps. Finally, high performance liquid chromatography (HPLC) can be employed for final purification steps. Microbial cells employed in expression of recombinant protein can be disrupted by any convenient method, including freeze-thaw cycling, sonication, mechanical disruption, or use of cell lysing agents.

Fermentation of yeast which express the inventive protein as a secreted protein greatly simplifies purification. Secreted recombinant protein resulting from a large-scale fermentation can be purified by methods analogous to those disclosed by Urdal et al. (*J. Chromatog.* 296:171, 1984). This reference describes two sequential, reversed-phase HPCL steps for purification of recombinant human GM-CSF on a preparative HPLC column.

Protein synthesized in recombinant culture is characterized by the presence of cell components, including proteins, in amounts and of a character which depend upon the purification steps taken to recover the inventive protein from the culture. These and preferably are present in innocuous contaminant quantities, on the order of less than about 1 percent by weight. Further, recombinant cell culture enables the production of the inventive proteins free of other proteins which may be normally associated with the proteins as they are found in the species of origin.

Uses and Administration of RANKL Compositions

The present invention provides methods of using therapeutic compositions comprising an effective amount of a protein and a suitable diluent and carrier, and methods for regulating an immune or inflammatory response. The use of RANKL in conjunction with soluble cytokine receptors or cytokines, or other immunoregulatory molecules is also contemplated.

For therapeutic use, purified protein is administered to a patient, preferably a human, for treatment in a manner appropriate to the indication. Thus, for example, RANKL protein compositions administered to regulate immune function can be given by bolus injection, continuous infusion, sustained release from implants, or other suitable technique. Typically, a therapeutic agent will be administered in the form of a composition comprising purified RANKL, in conjunction with physiologically acceptable carriers, excipients or diluents. Such carriers will be nontoxic to recipients at the dosages and concentrations employed.

Ordinarily, the preparation of such protein compositions entails combining the inventive protein with buffers, antioxidants such as ascorbic acid, low molecular weight (less than about 10 residues) polypeptides, proteins, amino acids, carbohydrates including glucose, sucrose or dextrins, chelating agents such as EDTA, glutathione and other stabilizers and excipients. Neutral buffered saline or saline mixed with conspecific serum albumin are exemplary appropriate diluents. Preferably, product is formulated as a lyophilizate using appropriate excipient solutions (e.g., sucrose) as diluents. Appropriate dosages can be determined in trials. The amount and frequency of administration will depend, of course, on such factors as the nature and severity of the indication being treated, the desired response, the condition of the patient, and so forth.

As shown herein, RANKL has beneficial effects on various cells important in the immune system. Accordingly, RANKL may be administered to an individual as a vaccine adjuvant, or as a therapeutic agent to upregulate an immune response, for example, ininfectious disease. Moreover, NF-κB has been found to play a protective role in preventing apoptotic death of cells induced by TNF-α or chemotherapy. Accordingly, agonists of RANK (i.e., RANKL and agonistic antibodies) will be useful in protecting RANK-expressing cells from the negative effects of chemotherapy or the presence of high levels of TNF-α such as occur in sepsis (see, i.e., Barinaga, *Science* 274:724, 1996, and the articles by Beg and Baltimore and Wang et al., pages 782 and 794 of that same issue of *Science*).

The following examples are offered by way of illustration, and not by way of limitation. Those skilled in the art will recognize that variations of the invention embodied in the examples can be made, especially in light of the teachings of the various references cited herein, the disclosures of which are incorporated by reference.

EXAMPLE 1

The example describes the identification and isolation of a DNA encoding a novel member of the TNF receptor superfamily. A partial cDNA insert with a predicted open reading frame having some similarity to CD40 (a cell-surface antigen present on the surface of both normal and neoplastic human B cells that has been shown to play an important role in B-cell proliferation and differentiation; Stamenkovic et al., *EMBO J.* 8:1403, 1989), was identified in a database containing sequence information from cDNAs generated from human bone marrow-derived dendritic cells (DC). The insert was excised from the vector by restriction endonuclease digestion, gel purified. labeled with $^{32}$P, and used to hybridize to colony blots generated from a DC cDNA library containing larger cDNA inserts using high stringency hybridization and washing techniques (hybridization in 5×SSC, 50% formamide at 42° C. overnight, washing in 0.5×SSC at 63° C.); other suitable high stringency conditions are disclosed in Sambrook et al. in *Molecular Cloning: A Laboratory Manual*, 2nd ed. (Cold Spring Harbor Laboratory, Cold Spring Harbor, N.Y.; 1989), 9.52–9.55. Initial experiments yielded a clone referred to as 9D-8A (SEQ ID NO:1); subsequent analysis indicated that this clone contained all but the extreme 5' end of a novel cDNA, with predicted intron sequence at the extreme 5' end (nucleotides 1-92 of SEQ ID NO:1). Additional colony hybridizations were performed, and a second clone was isolated. The second clone, referred to as 9D-15C (SEQ ID NO:3), contained the 5' end without intron interruption but not the full 3'end. SEQ ID NO:5 shows the nucleotide and amino acid sequence of a predicted full-length protein based on alignment of the overlapping sequences of SEQ ID NOs:1 and 3.

The encoded protein was designated RANK, for receptor of NF-κB. The cDNA encodes a predicted Type 1 transmembrane protein having 616 amino acid residues, with a predicted 24 amino acid signal sequence (the computer predicted cleavage site is after Leu24), a 188 amino acid extacellular domain, a 21 amino acid transmembrane domain, and a 383 amino acid cytoplasmic tail. The extracellular region of RANK displayed significant amino acid homology (38.5% identity, 52.3% similarity) to CD40. A cloning vector (pBluescriptSK⁻) containing human RANK sequence, designated pBluescript:huRANK (in *E. coli* DH10B), was deposited with the American Type Culture Collection, Rockville, Md. (ATCC) on Dec. 20, 1996, under terms of the Budapest Treaty, and given accession number 98285.

EXAMPLE 2

This example describes construction of a RANK DNA construct to express a RANK/Fc fusion protein. A soluble form of RANK fused to the Fc region of human $IgG_1$ was constructed in the mammalian expression vector pDC409 (U.S. Ser. No. 08/571,579). This expression vector encodes the leader sequence of the Cytomegalovirus (CMV) open reading frame R27080 (SEQ ID NO:9), followed by amino acids 33–213 of RANK, followed by a mutated form of the constant domain of human $IgG_1$ that exhibits reduced affinity for Fc receptors (SEQ ID NO:8; for the fusion protein, the Fc portion of the construct consisted of Arg3 through Lys232). An alternative expression vector encompassing amino acids 1–213 of RANK (using the native leader sequence) followed by the $IgG_1$ mutein was also prepared. Both expression vectors were found to induce high levels of expression of the RANK/Fc fusion protein in transfected cells.

To obtain RANK/Fc protein, a RANK/Fc expression plasmid is transfected into CV-1/EBNA cells, and supernatants are collected for about one week. The RANK/Fc fusion protein is purified by means well-known in the art for purification of Fc fusion proteins, for example, by protein A sepharose column chromatography according to manufacturer's recommendations (i.e., Pharmacia, Uppsala, Sweden). SDS-polyacrylamide gel electrophoresis analysis indicted that the purified RANK/Fc protein migrated with a molecular weight of ~55 kDa in the presence of a reducing agent, and at a molecular weight of ~110 kDa in the absence of a reducing agent.

N-terminal amino acid sequencing of the purified protein made using the CMV R27080 leader showed 60% cleavage after Ala20, 20% cleavage after Pro22 and 20% cleavage after Arg28 (which is the Furin cleavage site; amino acid residues are relative to SEQ ID NO:9); N-terminal amino acid analysis of the fusion protein expressed with the native leader showed cleavage predominantly after Gla25 (80% after Gla25 and 20% after Arg23; amino acid resides are relative to SEQ ID NO:6, full-length RANK). Both fusion proteins were able to bind a ligand for RANK is a specific manner (i.e., they bound to the surface of various cell lines such as a murine thymoma cell line. EL4), indicating that the presence of additional amino acids at the N-terminus of RANK does not interfere with its ability to bind RANKL. Moreover, the construct comprising the CMV leader encoded RANK beginning at amino acid 33; thus, a RANK peptide having an N-terminus at an amino acid between Arg23 and Pro33, inclusive, is expected to be able to bind a ligand for RANK in a specific manner.

Other members of the TNF receptor superfamily have a region of amino acids between the transmembrane domain and the ligand binding domain that is referred to as a 'spacer' region, which is not necessary for ligand binding. In RANK, the amino acids between 196 and 213 are predicted to form such a spacer region. Accordingly, a soluble form of RANK that terminates with an amino acid in this region is expected to retain the ability to bind a ligand for RANK in a specific manner. Preferred C-terminal amino acids for soluble RANK peptides are selected from the group consisting of amino acids 213 and 196 of SEQ ED NO:6, although other amino acids in the spacer region may be utilized as a C-terminus.

EXAMPLE 3

This example illustrates the preparation of monoclonal antibodies against RANK. Preparations of purified recombinant RANK, for example, or transfected cells expressing high levels of RANK, are employed to generate monoclonal antibodies against RANK using conventional techniques, such as those disclosed in U.S. Pat. No 4,411,993. DNA encoding RANK can also be used as an immunogen, for example, as reviewed by Pardoll and Beckerleg in *Immunity* 3:165, 1995. Such antibodies are likely to be useful in interfering with RANK-induced signaling (antagonistic or blocking antibodies) or in inducing a signal by cross-linking RANK (agonistic antibodies), as components of diagnostic or research assays for RANK or RANK activity, or in affinity purification of RANK.

To immunize rodents, RANK immunogen is emulsified in an adjuvant (such as complete or incomplete Freund's adjuvant, alum, or another adjuvant, such as Ribi adjuvant R700 (Ribi, Hamilton, Mont.), and injected in amounts ranging from 10–100 μg subcutaneously into a selected rodent, for example, BALB/c mice or Lewis rats. DNA may be given intradermally (Raz et al., *Proc. Natl. Acad. Sci. USA* 91:9519, 1994) or intamuscularly (Wang et al., *Proc. Natl. Acad. Sci. USA* 90:4156, 1993); saline has been found to be a suitable diluent for DNA-based antigens. Ten days to three weeks days later, the immunized animals are boosted with additional immunogen and periodically boosted thereafter on a weekly, biweekly or every third week immunization schedule.

Serum samples are periodically taken by retro-orbital bleeding or tail-tip excision for testing by dot-blot assay (antibody sandwhich), ELISA (enzyme-linked immunosorbent assay), immunoprecipitation, or other suitable assays, including FACS analysis. Following detection of an appropriate antibody titer, positive animals are given an intravenous injection of antigen in saline. Three to four days later, the animals are sacrificed, splenocytes harvested, and fused to a murine myeloma cell line (e.g., NSI or preferably Ag 8.653 [ATCC CRL 1580]. Hybridoma cell lines generated by this procedure are plated in multiple microtiter plates in a selective medium (for example, one containing hypoxanthine, aminopterin, and thymidine, or HAT) to inhibit proliferation of non-fused cells, myeloma-myeloma hybrids, and splenocyte-splenoctyte hybrids.

Hybridoma clones thus generated can be screened by ELISA for reactivity with RANK, for example, by adaptations of the techniques disclosed by Engvall et al., *Immunochem.* 8:871 (1971) and in U.S. Pat. No. 4,703,004. A preferred screening technique is the antibody capture technique described by Beckman et al., *J. Immunol.* 144:4212 (1990). Positive clones are then injected into the peritoneal cavities of syngeneic rodents to produce ascites containing high concentrations (>1 mg/ml) of anti-RANK monoclonal antibody. The resulting monoclonal antibody can be purified by ammonium sulfate precipitation followed by gel exclusion chromatography. Alternatively, affinity chromatography based upon binding of antibody to protein A or protein G can also be used, as can affinity chromatography based upon binding to RANK protein.

Monoclonal antibodies were generated using RANK/Fc fusion protein as the immunogen. These reagents were screened to confirm reactivity against the RANK protein. Using the methods described herein to monitor the activity of the mAbs, both blocking (i.e., antibodies that bind RANK and inhibit binding of a ligand to RANK) and non-blocking (i.e., antibodies that bind RANK and do not inhibit ligand binding) were isolated.

EXAMPLE 4

This example illustrates the induction of NF-κB activity by RANK in 293/EBNA cells (cell line was derived by transfection of the 293 cell line with a gene encoding Epstein-Barr virus nuclear antigen-1 (EBNA-1) that constitutively express EBNA-1 driven from human CMV immediate-early enhancer/promoter). Activation of NF-κB activity was measured in 293/EBNA cells essentially as described by Yao et al. (*Immunity* 3:811, 1995). Nuclear extracts were prepared and analyzed for NF-κB activity by a gel retardation assay using a 25 base pair oligonucleotide spanning the NF-κB binding sites. Two million cells were seeded into 10 cm dishes two days prior to DNA transfection and cultured in DMEM-F12 media containing 2.5% FBS (fetal bovine serum). DNA transfection were performed as described herein for the IL-8 promoter/reporter assays.

Nuclear extracts were prepared by solubilization of isolated nuclei with 400 mM NaCl (Yao et al., supra). Oligonucleotides containing an NF-κB binding site were annealed and endlabeled with $^{32}P$ using T4 DNA polynucleotide kinase. Mobility shift reactions contained 10 μof nuclear extract, 4 μg of poly(dI-dC) and 15,000 cpm labeled double-stranded oligonucleotide and incubated at room temperature for 20 minutes. Resulting protein-DNA complexes were resolved on a 6% native polyacrylamide gel in 0.25×Tris-borate-EDTA buffer.

Overexpression of RANK resulted in induction of NF-κB activity as shown by an appropriate shift in the mobility of the radioactive probe on the gel. Similar results were observed when RANK was triggered by a ligand that binds RANK and transduces a signal to cells expressing the receptor (i.e., by co-transfecting cells with human RANK and murine RANKL DNA; see Example 7 below), and would be expected to occur when triggering is done with agonistic antibodies.

EXAMPLE 5

This example describes a gene promoter/reporter system based on the human Interleukin-8 (IL-8) promoter used to analyze the activation of gene transcription in vivo. The induction of human IL-8 gene transcription by the cytokines Interleukin-1 (IL-1) or tumor necrosis factor-alpha TNF-α) is known to be dependent upon intact NF-κB and NF-IL-6 transcription factor binding sites. Fusion of the cytokine-responsive IL-8 promoter with a cDNA encoding the murine IL-4 receptor (mIL4R) allows measurement of promoter activation by detection of the heterologous reporter protein (mIL-4R) on the cell surface of transfected cells.

Human kidney epithelial cells (293/EBNA) are transfected (via the DEAE/DEXTRAN method) with plasmids encoding: 1). the reporter/promoter construct (referred to as pIL-8rep), and 2). the cDNA(s) of interest. DNA concentrations are always kept constant by the addition of empty vector DNA. The 293/EBNA cells are plated at a density of $2.5×10^4$ cells/ml (3 ml/well) in a 6 well plate and incubated for two days prior to transfection. Two days after transfection, the mIL-4 receptor is detected by a radioimmunoassay (RIA) described below.

In one such experiment, the 293/EBNA cells were co-transfected with DNA encoding RANK and with DNA encoding RANKL (sec Example 7 below). Co-expression of this receptor and its counterstructure by cells results in activation of the signaling process of RANK. For such co-transfection studies, the DNA concentration/well for the DEAE transfection were as follows: 40 ng of pIL-8rep [pBluescriptSK- vector (Stratagene)]; 0.4 ng CD40 (DNA encoding CD40, a control receptor, pCDM8 vector); 0.4 ng RANK (DNA encoding RANK; pDC409 vector), and either 1–50 ng CD40L (DNA encoding the ligand for CD40, which act as a positive control when co-transfected with CD40 and as a negative control when co-transfected with RANK; in pDC304) or RANKL (DNA encoding a ligand for RANK; in pDC406). Similar experiment can be done using soluble RANKL or agonistic antibodies to RANK to trigger cells transfected with RANK.

For the mIL-4R-specific RIA, a monoclonal antibody reactive with mIL-4R is labeled with $^{125}I$ via a Chloramine T conjugation method; the resulting specific activity is typically $1.5×10^{16}$ cpm/nmol. After 48 hour, transfected cells are washed once with media (DMEM/F12 5% FBS). Non-specific binding sites are blocked by the addition of pre-warmed binding media containing 5% non-fat dry milk and incubation at 37° C./5% $CO_2$ in a tissue culture incubator for one hour. The blocking media is decanted and binding buffer containing $^{125}I$ anti-mIL-4R (clone M1; rat IgG1) is added to the cells and incubated with rocking at room temperature for 1 hour. After incubation of the cells with the radio-labeled antibody, cells are washed extensively with binding buffer (2×) and twice with phosphate-buffered saline (PBS). Cells are lysed in 1 ml of 0.5M NaOH, and total radioactivity is measured with a gamma counter.

Using this assay, 293/EBNA co-transfected with DNAs encoding RANK demonstrated transcriptional activation, as shown by detection of muIL-4R on the cell surface. Overexpression of RANK resulted in transcription of muIL-4R, as did triggering of the RANK by RANKL. Similar results are observed when RANK is triggered by agonistic antibodies.

EXAMPLE 6

This example illustrates the association of RANK with TRAF proteins. Interaction of RANK with cytoplasmic TRAF proteins was demonstrated by co-immunoprecipitation assays essentially as described by Hsu et al. (*Cell* 84:299; 1996). Briefly, 293/EBNA cells were co-transfected with plasmids that direct the synthesis of RANK and epitope-tagged (FLAG®; SEQ ID NO:7) TRAF2 or TRAF3. Two days after transfection, surface proteins were labeled with biotin-ester, and cells were lysed in a buffer containing 0.5% NP-40. RANK and proteins associated with this receptor were immunoprecipitated with anti-RANK, washed extensively, resolved by electrophoretic separation on a 6–10% SDS polyacrylamide gel and electrophoretically transferred to a nitrocellulose membrane for Western blotting. The association of TRA2 and TRAF3 proteins with RANK was visualized by probing the membrane with an antibody that specifically recognizes the FLAG® epitope. TRAFs 2 and 3 did not immunopreciptitate with anti-RANK in the absence of RANK expression.

EXAMPLE 7

This example describes isolation of a ligand for RANK, referred to as RANKL, by direct expression cloning. The ligand was cloned essentially as describe in U.S. Ser. No. 08/249,189, filed May 24, 1994 (the relevant disclosure of which is incorporated by thymoma cell line EL-4 (ATCC TIB 39), called EL-40.5, derived by sorting five times with biotinylated CD40/Fe fusion protein in a FACS (fluorescence activated cell sorter). The cDNA library was made using standard methodology; the plasmid DNA was isolated and transfected into sub-confluent CV1-EBNA cells using a DEAE-dextran method. Transfectants were screened by slide autoradiography for expression of RANKL using a two-step binding method with RANK/Fc fusion protein as prepared in Example 2 followed by radioiodinated goal anti-human IgG antibody.

A clone encoding a protein that specifically bound RANK was isolated and sequenced; the clone was referred to as 11H. An expression vector containing murine RANKL sequence, designated pDC406:muRANK-L (in E. coli DH10B), was deposited with the American Type Culture Collection, Manassas, Va. (ATCC) on Dec. 20, 1996, under terms of the Budapest Treaty, and given accession number 98284. The nucleotide sequence and predicted amino acid sequence of this clone are illustrated in SEQ ID NO:10. This clone did not contain an initiator methionine; additional, fill-length clones were obtained from a 7B9 library (prepared substantially as described in U.S. Pat. No. 5,599,905, issued Feb. 4, 1997); the 5' region was found to be identical to that of human RANKL as shown in SEQ ID NO:13, amino acids 1 through 22, except for substitution of a Gly for a Thr at residue 9.

This ligand is useful for assessing the ability of RANK to bind RANKL by a number of different assays. For example, transfected cells expressing RANKL can be used in a FACS assay (or similar assay) to evaluate the ability of soluble RANK to bind RANKL. Moreover, soluble forms of RANKL can be prepared and used in assays that are known in the art (i.e., ELISA or BIAcore assays essentially as described in U.S. Ser. No. 08/249,189, filed May 24, 1994). RANKL is also useful in affinity purification of RANK, and as a reagent in methods to measure the levels of RANK in a sample. Soluble RANKL is also useful in inducing NF-κB activation and thus protecting cells that express RANK from apoptosis.

EXAMPLE 8

This example describes the isolation of a human RANK ligand (RANKL) using a PCR-based technique. Murine RANK ligand-specific oligonucleotide primers were used in PCR reactions using human cell line-derived first strand cDNAs as templates. Primers corresponded to nucleotides 478–497 and to the complement of nucleotides 858–878 of murine RANK ligand (SEQ ID NO:10). An amplified band approximately 400 bp in length from one reaction using the human epidermoid cell line KB (ATCC CCL-17) was gel purified, and its nucleotide sequence determined; the sequence was 85% identical to the corresponding region of murine RANK ligand, confirming that the fragment was from human RANKL.

To obtain full-length human RANKL cDNAs, two human RANKL-specific oligonucleotides derived from the KB PCR product nucleotide sequence were radiolabeled and used as hybridization probes to screen a human PBL cDNA library prepared in lambda gt10 (Stratagene, La Jolla, Calif., substantially as described in U.S. Pat. No. 5,599,905, issued Feb. 4, 1997. Several positive hybridizing plaques were identified and purified, their inserts subcloned into pBluescript SK[31] (Stratagene, La Jolla, Calif.), and their nucleotide sequence determined. One isolate, PBL3, was found to encode most of the predicted human RANKL, but appeared to be missing approximately 200 bp of 5' coding region. A second isolate, PBL5 was found to encode much of the predicted human RANKL, including the entire 5' end and an additional 200 bp of 5' untranslated sequence.

The 5' end of PBL5 and the 3' end of PBL3 were ligated together to form a full length cDNA encoding human RANKL. The nucleotide and predicted amino acid sequence of the full-length human RANK ligand is shown in SEQ ID NO: 12. Human RANK ligand shares 83% nucleotide and 84% amino acid identity with murine RANK ligand. A plasmid vector containing human RANKL sequence, designated pBluescript:huRANK-L (in E. coli DH10B), was deposited with the American Type Culture Collection, Rockville, Md. (ATCC) on Mar. 11, 1997 under terms of the Budapest Treaty, and given accession number 98354.

Murine and human RANKL are Type 2 transmembrane proteins. Murine RANKL contains a predicted 48 amino acid intracellular domain, 21 amino acid transmembrane domain and 247 amino acid extracellular domain. Human RANKL contains a predicted 47 amino acid intracellular domain, 21 amino acid transmembrane domain and 249 amino acid extracellular domain.

EXAMPLE 9

This example describes the chromosomal mapping of human RANK using PCR-based mapping strategies. Initial human chromosomal assignments were made using RANK and RANKL-specific PCR primers and a BIOS Somatic Cell Hybrid PCRable DNA kit from BIOS Laboratories (New Haven, Conn.), following the manufacturer's instructions. RANK mapped to human chromosome 18; RANK ligand mapped to human chromosome 13. More detailed mapping was performed using a radiation hybrid mapping panel Genebridge 4 Radiation Hybrid Panel (Research Genetics, Huntsville, Ala.; described in Walter, Mass. et al., *Nature Genetics* 7:22–28, 1994). Data from this analysis was then submitted electronically to the MIT Radiation Hybrid Mapper (URL: http://www-genome.wi.mit.edu/cgi-bin/contig/rhmapper.pl) following the instructions contained therein. This analysis yield specific genetic market names which when submitted electronically to the NCBI Entrez browser (URL: http://www3.ncbi.nlm.nih.gov/htbin-post/Entrez/query?db=c&form=0), yielded the specific map locations map locations. RANK mapped to chromosome 18q22.1, and RANKL mapped to chromosome 13q14.

EXAMPLE 10

This example illustrates the preparation of monoclonal antibodies against RANKL. Preparations of purified recombinant RANKL, for example, or transfixed cells expressing high levels of RANKL, are employed to generate monoclonal antibodies against RANKL using conventional, techniques, such as those disclosed in U.S. Pat. No. 4,411,993. DNA encoding RANKL can also be used as an immunogen, for example, as reviewed by Pardoll and Beckerleg in *Immunity* 3:165, 1995. Such antibodies are likely to be useful in interfering with RANKL signaling (antagonistic or blocking antibodies), as components of diagnostic or research assays for RANKL or RANKL activity, or in affinity purification of RANKL.

To immunize rodents, RANKL immunogen is emulsified in an adjuvant (such as complete or incomplete Freund's adjuvant, alum, or another adjuvant, such as Ribi adjuvant R700 (Ribi, Hamilton, Mont.), and injected in amounts ranging from 10–100 μg subcutaneously into a selected rodent, for example, BALB/c mice or Lewis rats. DNA may be given intradermally (Raz et al., *Proc. Natl. Acad. Sci. USA* 91:9519, 1994) or intamuscularly (Wang et al., *Proc. Natl. Acad. Sci. USA* 90:4156, 1993); saline has been found to be a suitable diluent for DNA-based antigens. Ten days to three weeks days later, the immunized animals are boosted with additional immunogen and periodically boosted thereafter on a weekly, biweekly or every third week immunization schedule.

Serum samples are periodically taken by retro-orbital bleeding or tail-tip excision for testing by dot-blot assay (antibody sandwich), ELISA (enzyme-linked immunosorbent assay), immunoprecipitation, or other suitable assays, including FACS analysis. Following detection of an appropriate antibody titer, positive animals are given an intravenous injection of antigen in saline. Three to four days later, the animals are sacrificed, splenocytes harvested, and fused to a murine myeloma cell line (e.g., NS1 or preferably Ag 8.653 [ATCC CRL 1580]). Hybridoma cell lines generated by this procedure are plated in multiple microtiter plates in a selective medium (for example, one containing hypoxanthine, aminopterin, and thymidine, or HAT) to inhibit proliferation of non-fused cells, myeloma-myeloma hybrids, and splenocyte-splenocyte hybrids.

Hybridoma clones thus generated can be screened by ELISA for reactivity with Immunochem. 8:871 (1971) and in U.S. Pat. No. 4,703,004. A preferred screening technique is the antibody capture technique described by Beckman et al., J. Immunol. 144:4212 (1990). Positive clones are then injected into the peritoneal cavities of syngeneic of rodents to produce ascites containing high concentrations (>1 mg/ml) of anti-RANK monoclonal antibody. The resulting monoclonal antibody can be purified by ammonia sulfate precipitation followed by gel exclusion chromatography. Alternatively, affinity chromatograhy based upon binding of antibody to protein A or protein G can also be used, as can affinity chromatography based binding to RANKL protein. Using the methods described herein to monitor the activity of the mAbs, both blocking (i.e., antibodies that bind RANKL and inhibit binding to RANK) and non-blocking (i.e., antibodies that bind RANKL and do not inhibit binding) are isolated.

EXAMPLE 11

This example demonstrates that RANK expression can be unregulated. Human peripheral blood T cells were purified by flow cytometry sorting or by negative selection using antibody coated beads, and activated with anti-CD3 (OKT3, Dako) coated plates or phytohemagglutinin in the presence or absence of various cytokines, including Interleukin-4 (IL-4), Transforming Growth Factor-β (TGF-β) and other commercially available cytokines ( IL1-α, IL-2, IL-3, IL-6, IL-7, IL-8, IL-10, IL-12, IL-15, IFN-γ, TNF-α). Expression of RANK was evaluated by FACS in a time course experiment for day 2 to day 8, using a mouse monoclonal antibody mAb144 (prepared as described in Example 3), as shown in the table below. Results are expressed as '+' to '++++' referring to the relative increase in intensity of staining with anti-RANK. Double labeling experiments using both anti-RANK and anti-CD8 or anti-CD4 antibodies were also performed.

TABLE 1

| Upregulation of RANK by Cytokines | |
|---|---|
| Cytokine (concentration) | Results: |
| IL-4 (50 ng/ml) | + |
| TGF-3 (5 ng/ml) | + to ++ |
| IL-4 (50 ng/ml) + TGF-β (5 ng/ml) | ++++ |
| IL1-α (10 ng/ml) | − |
| IL-2 (20 ng/ml) | − |
| IL-3 (25 ng/ml) | − |
| IL-7 (20 ng/ml) | − |
| IL-8 (10 ng/ml) | − |
| IL-10 (50 ng/ml) | − |
| IL-12 (10 ng/ml) | − |
| IL-15 (10 ng/ml) | − |
| IFN-γ (100 U/ml) | − |
| TNF-α (10 ng/ml) | − |

TABLE 1-continued

Of the cytokines tested, IL-4 and TGF-β increased the level of RANK expression on both CD8+ cytotoxic and CD4+ helper T cells from day 4 to day 8. The combination of IL-4 and TGF-β acted synergistically to upregulate expression of this receptor on activated T cells. This particular combination of cytokines is secreted by T cells, and is believed to be important in the generation of tolerance (reviewed in Mitchison and Sieper, Z. Rheumatol. 54:141, 1995), implicating the interaction of RANK in regulator of an immune response towards either tolerance or induction of an active immune response.

EXAMPLE 12

This example illustrates the influence of RANK.Fc and hRANKL on activated T cell growth. The addition of TGFβ to anti-CD3 activated human peripheral blood T lymphocytes induces proliferation arrest and ultimately death of most lymphocytes within the first few days of culture. We tested the effect of RANK:RANKL interactions on TGFβ-treated T cells by adding RANK.Fc or soluble human RANKL to T cell cultures.

Human peripheral blood T cells ($7 \times 10^5$ PBT) were cultured for six days on anti-CD3 (OKT3, 5 µg/ml) and anti-Flag (M1, 5 µg/ml) coated 24 well plates in the presence of TGFβ (1 ng/ml) and IL-4 (10 ng/ml), with or without recombinant FLAG-tagged soluble hRANKL (1 µg/ml) or RANK.Fc (10 µg/ml). Viable T cell recovery was determined by triplicate trypan blue countings.

The addition of RANK.Fc significantly reduced the number of viable T cells recovered after six days, whereas soluble RANKL greatly increased the recovery of viable T cells (FIG. 1). Thus, endogenous or exogenous RANKL enhances the number of viable T cells generated in the presence of TGFβ. TGFβ, along with IL-4, has been implicated in immune response regulation when secreted by the $T_H3$/regulatory T cell subset. These T cells are believed to mediate bystander suppression of effector T cells. Accordingly, RANK and its ligand may act in an auto/paracrine fashion to influence T cell tolerance. Moreover, TGFβ is known to play a role in the evasion of the immune system effected by certain pathogenic or opportunistic organisms. In addition to playing a role in the development of tolerance, RANK may also play a role in immune system evasion by pathogens.

EXAMPLE 13

This example illustrates the influence of the interaction of RANK on CD1a+ dendritic cells (DC). Functionally mature dendritic cells (DC) were generated in vitro from CD34+ bone marrow (BM) progenitors. Briefly, human BM cells from normal healthy volunteers were density fractionated using Ficoll medium and CD34+ cells immunoaffinity isolated using an anti-CD34 matrix column (Ceprate, Cell Pro). The CD34+ BM cells were then culture in human GM-CSF (20 ng/ml), human IL-4 (20 ng/ml), human TNF-β(20 ng/ml), human CHO-derived Flt3L (FL; 100 ng/ml) in Super McCoy's medium supplemented with 10% fetal calf serum in a fully humidified 37° C. incubator (5% $CO_2$) for 14 days. $CD1a^+$, $HLA-DR^+$ DC were then sorted using a FACStar Plus™, and used for biological evaluation of RANK On human $CD1a^+$ DC derived from $CD34^+$ bone marrow cells, only a subser (20–30%) of $CD1a^+$ DC expressed RANK at the cell surface as assessed by flow cytometric analysis. However, addition of CD40L to the DC cultures resulted in RANK surface expression on the majority of $CD1a^+$ DC. CD40L has been shown to activate DC by enhancing in vitro cluster formation, inducing DC morphological changes and upregulating HLA-DR, CD54, CD58, CD80 and CD86 expression Addition of RANKL to DC cultures significantly increased the degree of DC aggregation and cluster formation above control cultures, similar to the effects seen with CD40L. Sorted human $CD1a^+$ DC were cultured in a cytokine cocktail (GM-CSF, IL-4, TNF-α and FL), in cocktail plus CD40L (1 μg/ml), in cocktail plus RANKL (1 μg/ml), or in cocktail plus heat inactivated (ΔH) RANKL (1 g/ml) in 24-well flat bottomed culture plates in 1 ml culture media for 48–72 hours and then photographed using an inversion microscope. An increase in DC aggregation and cluster formation above control cultures was not evident when heat inactivated RANKL was used, indicating that this effect was dependent on biologically active protein. However, initial phenotypic analysis of adhesion molecule expression indicated that RANKL-induced clustering was not due to increased levels of CD2, CD11a, CD54 or CD58.

Figure 2:
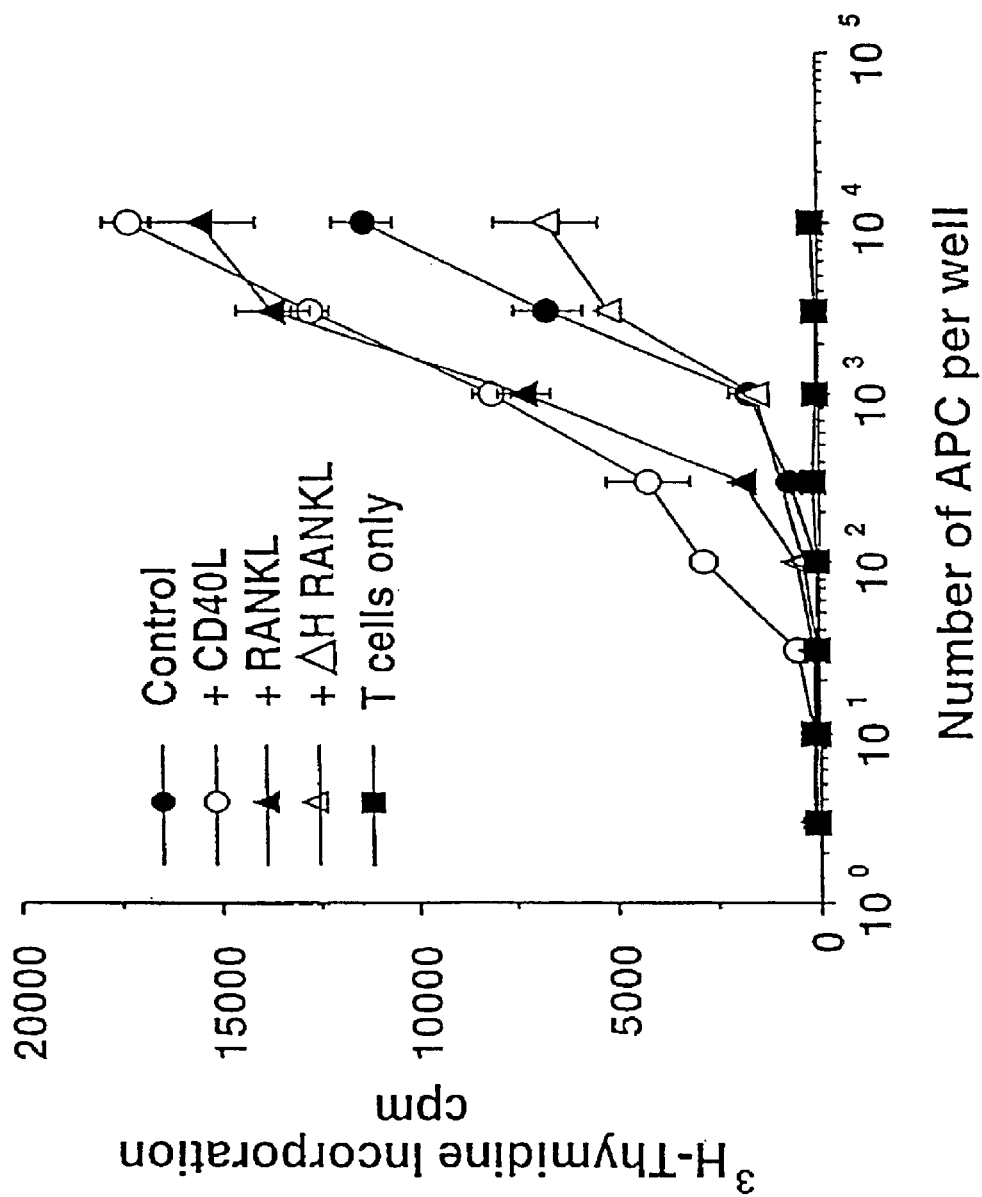
FIG. 2 demonstrates that RANKL enhances DC allostimulatory capacity. Allogeneic T cells were incubated with varying numbers of irradiated DC cultured as described in Example 13. The cultures were pulsed with [$^3$H]-thymidine and the cells harvested onto glass fiber sheets for counting. Values represent the ± standard deviation (SD) of triplicate cultures.

The addition of RANKL to $CD1a^+$ DC enhanced their allo-stimulatory capacity in a mixed lymphocyte reaction (MLR) by at least 3- to 10-fold, comparable to CD40L-cultured DC (FIG. 2). Allogeneic T cells ($1 \times 10^5$) were incubated with varying numbers of irradiated (2000 rad) DC cultured as indicated above in 96-well round bottomed culture plates in 0.2 ml culture medium for four days. The cultures were pulsed with 0.5 mCi [$^3$H]-thymidine for eight hours and the cells harvested onto glass fiber sheets for counting on a gas phase β counter. The background counts for either T cells or DC cultured alone were <100 cpm. Values represent the mean ± SD of triplicate cultures. Heat inactivated RANKL had no effect. DC allo-stimulatory activity was not further enhanced when RANKL and CD40L were used in combination, possibly due to DC functional capacity having reached a maximal level with either cytokine alone. Neither RANKL nor CD40L enhanced the in vitro growth of DC over the three day culture period. Unlike CD40L, RANKL did not significantly increase the levels of HLA-DR expression nor the expression of CD80 or CD86.

RANKL can enhance DC cluster formation and functional capacity without modulating known molecules involved in cell adhesion (CD18, CD54), antigen presentation (HLA-DR) or costimulation (CD86), all of which are regulated by CD40/CD40L signaling. The lack of an effect on the expression of these molecules suggests that RANKL may regulate DC function via an alternate pathway(s) distinct from CD40/CD40L. Given that CD40L regulates RANK surface expression on in vitro-generated DC and that CD40L is upregulate on activated T cells during DC-T cell interactions, RANK and its ligand may form an important part of the activation cascade that is induced during DC-mediated T cell expansion. Furthermore, culture of DC in RANKL results in decreased levels of CD1b/c expression, and increased levels of CD83. Both of these molecules are similarly modulated during DC maturation by CD40L (Caux et al. *J. Exp. Med.* 180:1263; 1994), indicating that RANKL induces DC maturation.

Dendritic cells are referred to as "professional" antigen presenting cells, and have a high capacity for sensitizing MHC-restricted T cells. There is growing interest in using dendritic cells ex vivo as tumor or infectious disease vaccine adjuvants (see, for example, Romani, et al., *J. Exp. Med.*, 180:83, 1994). Therefore, an agent such as RANKL that induces DC maturation and enhances the ability of dendritic cells to stimulate an immune response is likely to be useful in immunotherapy of various diseases.

EXAMPLE 14

This example describes the isolation of the murine homolog of RANK, referred to as muRANK. MuRANK was isolated by a combination of cross-species PCR and colony hybridization. The conservation of Cys residues in the Cys-rich pseudorepeats of the extracellular domains of TNFR superfamily member proteins was exploited to design human RANK-based PCR primers to be used on murine first strand cDNA from various sources. Both the sense upstream primer and the antisense downstream primer were designed to have their 3' ends terminate within Cys residues.

The upstream sense primer encoded nucleotides 272–295 of SEQ ID NO:5 (region encoding amino acids 79–86); the downstream antisense primer encoded the complement of nucleotides 409–427 (region encoding amino acids 124–130). Standard PCR reactions were set up and run, using theses primers and first strand cDNA from various murine cell line or tissue sources. Thirty reaction cycles of 94° C. for 30 seconds, 50° C. for 30 seconds, and 72° C. for 20 seconds were run. PCR products were analyzed by electrophoresis, and specific bands were seen in several samples. The band from one sample was gel purified 85% identical to the corresponding human RANK nucleotide sequence.

A plasmid based-cDNA library prepared from the murine fetal liver epithelium line FLE18 (one of the cell lines identified as positive in the PCR screen) was screened for full-length RANK cDNAs using murine RANK-specific oligonucleotide probes derived from the murine RANK sequence determined from sequencing the PCR product. Two cDNAs, one encoding the 5' end and one encoding the 3' end of full-length murine RANK (based on sequence comparison with the full-length human RANK) were recombined to generate a full-length murine RANK cDNA. The nucleotide and amino acid sequence of muRANK are shown in SEQ ID) Nos:14 and 15.

The cDNA encodes a predicted Type 1 transmembrane protein having 625 amino acid residues, with a predicted 30 amino acid signal sequence, a 184 amino acid extracellular domain, a 21 amino acid transmembrane domain, and a 390 amino acid cytoplasmic tail. The extracellular region of muRANK displayed significant amino acid homology (69.7% identity, 80.8% similarity) to huRANK. Those of skill in the art will recognize that the actual cleavage site can be different from that predicted by computer; accordingly, the N-terminal of RANK may be from amino acid 25 to amino acid 35.

Other members of the TNF receptor superfamily have a region of amino acids between the transmembrane domain and the ligand binding domain that is referred to as a 'spacer' region, which is not necessary for ligand binding. In muRANK, the amino acids between 197 and 214 are predicted to form such a spacer region. Accordingly, a soluble form of RANK that terminates with an amino acid in this region is expected to retain the ability to bind a ligand for RANK in a specific manner. Preferred C-terminal amino acids for soluble RANK peptides are selected from the group consisting of amino acids 214, and 197 of SEQ ID NO:14, although other amino acids in the spacer region may be utilized is a C-terminus.

EXAMPLE 15

This example illustrates the preparation of several different soluble forms of RANK and RANKL. Standard techniques of restriction enzyme cutting and ligation, in combination with PCR-based isolation of fragments for which no convenient restriction sites existed, were used. When PCR was utilized, PCR products were sequence to ascertain whether any mutations had been introduced, no such mutations were found.

In addition to the huRANK/Fc described in Example 2, another RANK/Fc fusion protein was prepared by ligating DNA encoding amino acids 1–213 of SEQ ID NO.6, to DNA encoding amino acids 3–232 of the Fc mutein described previously (SEQ ID NO:8). A similar construct was prepared for murine RANK, ligating DNA encoding amino acids 1–213 of full-length murine RANK (SEQ ID NO:15) to DNA encoding amino acids 3–232 of the Fc mutein SEQ ID NO:8).

A soluble, tagged, poly-His version of huRANKL was prepared by ligating DNA encoding the leader peptide from the immunoglobulin kappa chain (SEQ ID NO:16) to DNA encoding a short version of the FLAG™ tag (SEQ ID NO:17), followed by codons encoding Gly Ser, then a poly-His tag (SEQ ID NO:18), followed by codons encoding, Gly Thr Ser, and DNA encoding amino acids 138–317 of SEQ ID NO:13. A soluble, poly-His tagged version of murine RANKL was prepared by ligating DNA encoding the CMV leader (SEQ ID NO:9) to codons encoding Arg Thr Ser, followed by DNA encoding poly-His (SEQ ID NO:18) followed by DNA encoding amino acids 119–294 of SEQ ID No:11.

A soluble, oligomeric form of huRANKL was prepared by ligating DNA encoding the CMV leader (SEQ ID NO:9) to a codon encoding Asp followed by DNA ending a trimer-former "leucine" zipper (SEQ ID NO:19), then by codons encoding Thr Arg Ser followed by amino acids 138–317 of SEQ ID NO:13.

These and other constructs are prepared by routine experimentation. The various DNAs are then inserted into a suitable expression vector, and expressed. Particularly preferred expression vectors are those which can be used in mammalian cells. For example, pDC409 and pDC304, described herein, are useful for transient expression. For stable transfection, the use of CHO cells is preferred; several useful vectors are described in U.S. Ser. No. 08/785,150, now allowed, for example, one of the 2A5-3 λ-derived expression vectors discussed therein.

EXAMPLE 16

This example demonstrates that RANKL expression can be up-regulated on murine T cells. Cells were obtained from mesenteric lymph nodes of C57BL/6 mice, and activated with anti-CD3 coated plates, Concanavalin A (ConA) or phorbol myristate acetate in combination with ionomycin (anti-CD33: 500A2; Immunex Corporation, Seattle Wash., ConA, PMA, ionomycin, Sigma, St. Louis, Mo.) Substantially as described as described herein, and cultured from about 2 to 5 days. Expression of RANKL was evaluated in a three color analysis by FACS, using antibodies to the T cell markers CD4, CD8 and CD45RB, and RANK/Fc, prepared as described herein.

RANKL was not expressed on unstimulated murine T cells. T cells stimulated with either anti-CD3, ConA, or PMA/ionomycin, showed differential expression of RANKL: $CD4^+/CD45RB^{Lo}$ and $CD4^+/CD45R^{Hi}$ cells were positive for RANKL, but CD8+ cells were not. RANKL was not observed on B cells, similar to results observed with human cells.

EXAMPLE 17

This example illustrated the effects of murine RANKL on cell proliferation and activation. Various cells of cell lines representative of cells that play role in an immune response (murine spleen, thymus and hymphnode) were evaluated by culturing them under conditions promoting their viability, in the presence or absence of RANKL. RANKL did not stimulate any of the tested cells to proliferate. One cell line, a macro cell line referred to as RAW 264.7 (ATCC accession number TIB 71) exhibited some signs of activation.

RAW cells constitutively produce small amounts of TNF-α. Incubation with either human of murine RANKL enhanced production of TNF-α by these cells in a dose dependent manner. The results were not due to contamination of RANKL preparations with endotoxin, since boiling RANKL for 10 minutes abrogated TNF-α production, whereas a similar treatment of purified endotoxin (LPS) did not affect the ability of the LPS to stimulate TNF-α production. Despite the fact that RANKL activated the macrophage cell line RAW T64.7 for TNF-α production, neither human RANKL nor murine RANKL stimulated nitric oxide production by these cells.

EXAMPLE 18

This example illustrates the effects of murine RANKL on growth and development of the thymus in fetal mice. Pregnant mice were injected with 1 mg of RANK/Fc or vehicle control protein (murine serum albumin; MSA) on days 13, 16 and 19 of gestation. After birth, the neonates continued to be injected with RANK/Fc intraperitoneally (IP) on a daily basis, beginning at a dose of 1 μg, and doubling the dose about every four days, for a final dosage of 4 μg. Neonates were taken at days 1, 8 and 15 post birth, their thymuses and spleens harvested and examined for size, cellular and phenotypic composition.

A slight reduction in thymic size at day 1 was observed in the neonates born to the female injected with RANK/Fc; a similar decrease in size was not observed in the control neonates. At day 8, thymic size and cellularity were reduced by about 50% in the RANK/Fc-treated animals as compared to MSA treated mice. Phenotype analysis demonstrated that the relative proportions of different T cell populations in the thymus were the same in the RANK/Fc mice as the control mice, indicating that the decreased cellularity was due to a global depression in the number of thymic T cells as opposed to a decrease in a specific population(s). The RANK/Fc-treated neonates were not significantly different from the control neonates at day 15 with respect to either size, cellularity or phenotype of thymic cells. No significant differences were observed in spleen size, cellularity or composition at any of the time points evaluated. The difference in cellularity on day 8 and not on day 15 may suggest that RANK/Fc may assert its effect early in thymic development.

EXAMPLE 19

This example demonstrate that the C-terminal region of the cytoplasmic domain of RANK is important for binding of several different TRAF proteins. RANK contains at least two recognizable PXQX(X)T motifs that are likely TRAF dockings sites. Accordingly, the important of various regions of the cytoplasmic domain of RANK for TRAF binding was evaluated. A RANK/GST fusion protein was prepared substantially as described in Smith and Johnson. *Gene* 67:31 (1988), and used in the preparation of various truncations as described below.

Comparison of the nucleotide sequence of murine and human RANK indicated that there were several conserved regions that could be important for TRAF binding. Accordingly, a PCR-based technique was developed to facilitate preparation of various C-terminal truncations that would retain the conserved regions. PCR primers were designed to introduce a stop codon and restriction enzyme site at selected points, yielding the truncations described in Table 2 below. Sequencing confirmed that no undesired mutations had been introduced in the constructs.

Radio-labeled ($^{35}$S-Met, Cys) TRAF proteins were prepared by in vitro translation using a commercially available reticulocyte lysate kit according to manufacturer's instructions (Promega). Truncated GST fusion proteins were purified substantially as described in Smith and Johnson (supra). Briefly, *E. coli* were transfected with an expression vector encoding a fusion protein, and induced to express the protein. The bacteria were lysed, insoluble material removed, and the fusion protein isolated by precipitation with glutathione-coated beads (Sepahrose 4B, Pharmacia, Uppsala Sweden)

The beads were washed, and incubated with various radiolabeled TRAF proteins. After incubation and wash steps, the fusion protein/TRAF complexes were removed from the beads by boiling in 0.1% SDS+β-mercaptoethanol, and loaded onto 12% SDS gels (Novex). The gels were subjected to autoradiography, and the presence or absence of radiolabled material recorded. The results are shown in Table 2 below.

TABLE 2

Binding of Various TRAF Proteins to the Cytoplasmic Domain of RANK

| C terminal Truncations: | E206-S339 | E206-Y421 | E206-M476 | E206-G544 | Full length |
|---|---|---|---|---|---|
| TRAF1 | − | − | − | − | ++ |
| TRAF2 | − | − | − | − | ++ |
| TRAF3 | − | − | − | − | ++ |
| TRAF4 | − | − | − | − | − |
| TRAF5 | − | − | − | − | + |
| TRAF6 | − | + | + | + | ++ |

These results indicate that TRAF1, TRAF2, TRAF3, TRAF 5 and TRAF6 bind to the most distal portion of the RANK cytoplasmic domain (between amino-acid G544 and A616). TRAF6also has a binding site between S339 and Y421. In this experiment, TRAF5 also bound the cytoplasmic of RANK.

We claim:

1. An isolated DNA molecule encoding a RANKL polypeptide that binds RANK, wherein said polypeptide comprises amino acids 1 to 294 of SEQ ID NO:11.

2. The isolated DNA molecule of claim 1, wherein said DNA molecule comprises nucleotides 3 to 884 of SEQ ID NO:10.

3. An expression vector comprising a DNA molecule of claim 2.

4. A host cell transformed or transfected with an expression vector of claim 3.

5. A process for preparing a RANKL polypeptide, comprising culturing a host cell of claim 4 under conditions promoting expression of RANKL polypeptide, and recovering the RANKL polypeptide so expressed.

6. An expression vector comprising a DNA molecule of claim 1.

7. A host cell transformed or transfected with an expression vector of claim 6.

8. A process for preparing a RANKL polypeptide, comprising culturing a host cell of claim 7 under conditions promoting expression of RANKL polypeptide, and recovering the RANKL polypeptide so expressed.

9. An isolated DNA molecule encoding a RANKL polypeptide that binds RANK, wherein said polypeptide comprises amino acids 48 to 290 of SEQ ID NO:11.

10. The isolated DNA molecule of claim 9, wherein said DNA molecule comprises nucleotides 144 to 872 of SEQ ID NO:10.

11. An expression vector comprising a DNA molecule of claims 10.

12. A host cell transformed or transfected with an expression vector of claim 11.

13. A process for preparing a RANKL polypeptide, comprising culturing a host cell of claim 12 under conditions promoting expression of RANKL polypeptide, and recovering the RANKL polypeptide so expressed.

14. An expression vector comprising a DNA molecule of claim 9.

15. A host cell transformed or transfected with an expression vector of claim 14.

16. A process for preparing a RANKL polypeptide, comprising culturing a host cell of claim 15 under conditions promoting expression of RANKL polypeptide, and recovering the RANKL polypeptide so expressed.

17. An isolated or recombinant nucleic acid encoding a RANKL polypeptide selected from the group consisting of:
   a) the RANKL of SEQ ID NO:11; and
   b) a fusion protein comprising the RANKL of SEQ ID NO:11,
wherein said RANKL polypeptide is from a mammal.

18. A cell comprising said recombinant nucleic acid of claim 17.

19. The cell of claim 18, wherein said cell is:
   a) a prokaryotic cell;
   b) a eukaryotic cell;
   c) a bacterial cell;
   d) a yeast cell;
   e) an insect cell;
   f) a mammalian cell;
   g) a mouse cell; or
   h) a human cell.

20. A method of making a protein, comprising culturing said cell of claim 18 an environment resulting in expressing said protein and recovering said protein.

21. A kit comprising said nucleic acid of claim 17.

22. An isolated or recombinant nucleic acid according to claim 17, wherein said RANKL polypeptide is a RANKL immunogen.

23. A cell comprising said nucleic acid of claim 22.

24. A method of making a protein, comprising culturing said cell of claim 23 in an environment resulting in expressing said protein and recovering said protein.

25. A method of making a double-stranded nucleic acid comprising contacting said nucleic acid of claim 22 with a complementary nucleic acid under selective hybridization conditions at least as stringent as the conditions of hybridizing at 50° C. in 5×SSC, thereby forming said double-stranded nucleic acid.

26. An isolated or recombinant nucleic acid according to claim 17, which exhibits 100% identity over the protein coding portion of a DNA encoding said RANKL sequence.

27. A cell comprising said nucleic acid of claim 26.

28. A vector comprising a nucleic acid according to claim 17 and;
   a) transcriptional regulatory sequences operably linked to said RANKL coding sequence; or
   b) an origin of replication.

29. A cell comprising said vector of claim 28.

30. A method of making a protein, comprising culturing said cell of claim 29 in an environment resulting in expressing said protein and recovering said protein.

31. An isolated or recombinant nucleic acid according to claim 17, wherein said nucleic acid:
   a) is from a natural source;
   b) comprises a detectable label;
   c) comprises synthetic nucleotide sequence; or
   d) comprises a full length coding sequence.

32. A cell comprising said nucleic acid of claim 31.

33. A kit comprising a nucleic acid of claim 31.

34. A method of making a nucleic acid of claim 17, comprising amplifying said nucleic acid using PCR amplification methods.

* * * * *

UNITED STATES PATENT AND TRADEMARK OFFICE
CERTIFICATE OF CORRECTION

| | |
|---|---|
| PATENT NO. | : 6,838,262 B1 |
| APPLICATION NO. | : 09/688459 |
| DATED | : January 4, 2005 |
| INVENTOR(S) | : Anderson et al. |

It is certified that error appears in the above-identified patent and that said Letters Patent is hereby corrected as shown below:

In the Specification

Col. 1, line 38     "Apoptois" should read -- Apoptosis --;
       line 42     "calls" should read -- cells --.
Col. 2, lines 64-65     "TRAF2,and TRAF3 (is" should read -- TRAF2, and TRAF3 (as --.
Col. 3, line 34     "inflamatory" should read -- inflammatory --;
       line 36     "DNAs." should read -- DNAs, --;
       line 40     "mutcins" should read -- muteins --.
Col. 5, line 27     "Fe" should read -- Fc --;
       line 28     "hinges" should read -- hinge --.
Col. 6, line 35     "up-updown" should read -- up-up-down --.
Col. 7, line 8     "e,g.," should read -- e.g., --;
       line 61     "type of mutation" should read -- types of mutations --;
       line 64     "protein." should read -- proteins. --;
       line 65     "substitution" should read -- substitutions --.
Col. 8, lines 49-50     "in alerted" should read -- an altered --;
       line 50     "alerted" (second occurrence) should read -- altered --;
       line 66     after "example," insert -- hybridization in 6 × SSC at 63°C overnight; washing in 3 × SSC at 55°C), and other --.
Col. 9, line 33     "arc" should read -- are --;
       line 41     "polylmerase" should read -- polymerase --.
Col. 11, line 18     "sequence" should read -- sequences --;
       line 66     "Suitaible" should read -- suitable --.
Col. 12, line 1     "J. Biol. 25:" should read -- J. Biol. Chem. 255: --;
       line 4     "glyceraldehydes-3" should read -- glyceraldehyde-3 --;
       line 8     "isometrase," should read -- isomerase --;
       line 20     "Kuijan" should read -- Kurjan --;
       line 61     "detected" should read -- deleted --.
Col. 13, line 7     "taansfected" should read -- transfected --;
       line 18     "prokaaryotes" should read -- prokaryotes --;

Signed and Sealed this
Seventeenth Day of December, 2013

Margaret A. Focarino
*Commissioner for Patents of the United States Patent and Trademark Office*

CERTIFICATE OF CORRECTION (continued)

U.S. Pat. No. 6,838,262 B1

| | | |
|---|---|---|
| | line 42 | "Pseudomzonas, Streplomyces," should read -- Pseudomonas, Streptomyces, --; |
| | line 48 | "vector" should read -- vectors --; |
| | line 54 | "permiting" should read -- permitting --. |
| Col. 14, line 7 | | "Depression" should read -- Derepression --; |
| | line 39 | "Following," should read -- Following --; |
| | line 40 | "purificatioin" should read -- purification --. |
| Col. 15, line 20 | | "HPCL" should read -- HPLC --; |
| | line 27 | after "These" insert -- components ordinarily will be of yeast, prokaryotic or non-human higher eukaryotic origin --; |
| | line 32 | "in the" should read -- in nature in the --. |
| Col. 16, line 13 | | "794" should read -- 784 --; |
| | line 53 | after "receptor" insert -- activator --; |
| | line 58 | "extacellular" should read -- extracellular --. |
| Col. 17, line 40 | | "Gla25" should read -- Gln25 --; |
| | line 41 | "Gla25" should read -- Gln25 --; |
| | line 41 | "resides" should read -- residues --; |
| | line 65 | "SEQ ED" should read -- SEQ ID --. |
| Col. 18, line 32 | | "sandwhich" should read -- sandwich --; |
| | line 38 | "NSI" should read -- NS1 --; |
| | line 39 | "1580]" should read -- 1580]) --. |
| Col. 19, line 15 | | "transfection" should read -- transfections --; |
| | line 43 | "TNF-α)" should read -- (TNF-α) --; |
| | line 62 | "(sec" should read -- (see --. |
| Col. 20, line 4 | | "act as" should read -- acts as --; |
| | line 7 | "experiment" should read -- experiments --; |
| | line 13 | "48 hour," should read -- 48 hours, --; |
| | line 50 | "TRA2" should read -- TRAF2 --; |
| | line 59 | "describe" should read -- described --; |
| | line 61 | after "by" insert -- reference herein), for CD40L. Briefly, a library was prepared from a clone of a mouse --. |
| Col. 21, line 3 | | "goal" should read -- goat --; |
| | line 16 | "fill-length" should read -- full-length --. |
| Col. 22, line 33 | | "yield" should read -- yields --; |
| | line 33 | "market" should read -- marker --; |
| | line 37 | delete "map locations". |
| Col. 23, line 17 | | after "with" insert -- RANKL, for example, by adaptations of the techniques disclosed by Engvall et al., --; |
| | line 21 | delete "of" (second occurrence); |
| | line 24 | "ammonia" should read -- ammonium --; |
| | line 26 | "chromatograhy" should read -- chromatography --; |
| | line 28 | after "based" insert -- upon --; |
| | line 38 | "unregulated" should read -- up-regulated --; |
| | line 60 | "TGF-3 (5 ng/ml)" should read -- TGF-β (5 ng/ml) --. |
| Col. 24, line 17 | | "by T cells" should read -- by suppresser T cells --; |

CERTIFICATE OF CORRECTION (continued)
U.S. Pat. No. 6,838,262 B1

| | |
|---|---|
| Col. 30, line 10 | "radiolabled" should read -- radiolabeled --; |
| line 20 | "regulator" should read -- regulation --; |
| line 65 | "Cell Pro" should read -- CellPro --; |
| line 66 | "culture" should read -- cultured --; |
| line 67 | "TNF-β(20" should read -- TNF-α (20 --. |
| Col. 25, line 7 | "subser" should read -- subset --; |
| line 58 | "upregulate" should read -- upregulated --. |
| Col. 26, line 19 | "cDNA" should read -- cDNAs --; |
| line 27 | "theses" should read -- these --; |
| line 27 | "cDNA" should read -- cDNAs --; |
| line 32 | after "purified" insert -- and DNA sequencing revealed that the sequence between the primers was approximately --; |
| line 36 | "based-cDNA" should read -- based cDNA --. |
| Col. 27, line 4 | "is" should read -- as --; |
| line 12 | "sequence" should read -- sequenced --; |
| line 13 | "introduced," should read -- introduced; --; |
| line 22 | "Fc mutein SEQ" should read -- Fc mutein (SEQ --; |
| line 61 | "anti-CD33:" should read -- anti-CD3: --; |
| line 63 | delete "as described" (second occurrence). |
| Col. 28, line 4 | "CD4$^+$/CD45R$^{Hi}$" should read -- CD4$^+$/CD45RB$^{Hi}$ --; |
| line 11 | "illustrated" should read -- illustrates --; |
| line 12 | "of" should read -- or --; |
| line 13 | "play role" should read -- play a role --; |
| line 14 | "hymphnode" should read -- lymphnode --; |
| line 18 | "macro" should read -- macrophage --; |
| line 22 | "of" should read -- or --; |
| line 46 | "cellular" should read -- cellularity --; |
| line 54 | "Phenotype" should read -- Phenotypic --. |
| Col. 29, line 3 | "demonstrate" should read -- demonstrates --; |
| line 7 | "dockings" should read -- docking --; |
| line 7 | "important" should read -- importance --.--; |
| lines 30-31 | after "cytoplasmic" insert -- domain --. |

In the Claims

| | |
|---|---|
| Column 76, Claim 11, line 2 | "claims 10" should read -- claim 10 --. |
| Column 77, Claim 20, line 2 | "claim 18 an" should read -- claim 18 in an --. |

```
                        SEQUENCE LISTING (1) GENERAL INFORMATION:

(iii) NUMBER OF SEQUENCES: 19

(2) INFORMATION FOR SEQ ID NO:1:

(i) SEQUENCE CHARACTERISTICS:
         (A) LENGTH: 3115 base pairs
         (B) TYPE: nucleic acid
         (C) STRANDEDNESS: single
         (D) TOPOLOGY: linear (ii) MOLECULE TYPE: cDNA (iii) HYPOTHETICAL: NO (iv) ANTI-SENSE: NO (vi) ORIGINAL SOURCE:
         (A) ORGANISM: HOMO SAPIENS (vii) IMMEDIATE SOURCE:
         (A) LIBRARY: BONE-MARROW DERIVED DENDRITIC CELLS
         (B) CLONE: 9D-8A (ix) FEATURE:
         (A) NAME/KEY: CDS
         (B) LOCATION: 93..1868

(xi) SEQUENCE DESCRIPTION: SEQ ID NO:1:

GCTGCTGCTG CTCTGCGCGC TGCTCGCCCG GCTGCAGTTT TATCCAGAAA GAGCTGTGTG       60

GACTCTCTGC CTGACCTCAG TGTTCTTTTC AG GTG GCT TTG CAG ATC GCT CCT      113
                                   Val Ala Leu Gln Ile Ala Pro
```

-continued

```
                                 1                   5
CCA TGT ACC AGT GAG AAG CAT TAT GAG CAT CTG GGA CGG TGC TGT AAC      161
Pro Cys Thr Ser Glu Lys His Tyr Glu His Leu Gly Arg Cys Cys Asn
             10                  15                  20

AAA TGT GAA CCA GGA AAG TAC ATG TCT TCT AAA TGC ACT ACT ACC TCT      209
Lys Cys Glu Pro Gly Lys Tyr Met Ser Ser Lys Cys Thr Thr Thr Ser
         25                  30                  35

GAC AGT GTA TGT CTG CCC TGT GGC CCG GAT GAA TAC TTG GAT AGC TGG      257
Asp Ser Val Cys Leu Pro Cys Gly Pro Asp Glu Tyr Leu Asp Ser Trp
 40                  45                  50                  55

AAT GAA GAA GAT AAA TGC TTG CTG CAT AAA GTT TGT GAT ACA GGC AAG      305
Asn Glu Glu Asp Lys Cys Leu Leu His Lys Val Cys Asp Thr Gly Lys
                 60                  65                  70

GCC CTG GTG GCC GTG GTC GCC GGC AAC AGC ACG ACC CCC CGG CGC TGC      353
Ala Leu Val Ala Val Val Ala Gly Asn Ser Thr Thr Pro Arg Arg Cys
             75                  80                  85

GCG TGC ACG GCT GGG TAC CAC TGG AGC CAG GAC TGC GAG TGC TGC CGC      401
Ala Cys Thr Ala Gly Tyr His Trp Ser Gln Asp Cys Glu Cys Cys Arg
         90                  95                 100

CGC AAC ACC GAG TGC GCG CCG GGC CTG GGC GCC CAG CAC CCG TTG CAG      449
Arg Asn Thr Glu Cys Ala Pro Gly Leu Gly Ala Gln His Pro Leu Gln
105                 110                 115

CTC AAC AAG GAC ACA GTG TGC AAA CCT TGC CTT GCA GGC TAC TTC TCT      497
Leu Asn Lys Asp Thr Val Cys Lys Pro Cys Leu Ala Gly Tyr Phe Ser
120                 125                 130                 135

GAT GCC TTT TCC TCC ACG GAC AAA TGC AGA CCC TGG ACC AAC TGT ACC      545
Asp Ala Phe Ser Ser Thr Asp Lys Cys Arg Pro Trp Thr Asn Cys Thr
             140                 145                 150

TTC CTT GGA AAG AGA GTA GAA CAT CAT GGG ACA GAG AAA TCC GAT GCG      593
Phe Leu Gly Lys Arg Val Glu His His Gly Thr Glu Lys Ser Asp Ala
         155                 160                 165

GTT TGC AGT TCT TCT CTG CCA GCT AGA AAA CCA CCA AAT GAA CCC CAT      641
Val Cys Ser Ser Ser Leu Pro Ala Arg Lys Pro Pro Asn Glu Pro His
170                 175                 180

GTT TAC TTG CCC GGT TTA ATA ATT CTG CTT CTC TTC GCG TCT GTG GCC      689
Val Tyr Leu Pro Gly Leu Ile Ile Leu Leu Leu Phe Ala Ser Val Ala
185                 190                 195

CTG GTG GCT GCC ATC ATC TTT GGC GTT TGC TAT AGG AAA AAA GGG AAA      737
Leu Val Ala Ala Ile Ile Phe Gly Val Cys Tyr Arg Lys Lys Gly Lys
200                 205                 210                 215

GCA CTC ACA GCT AAT TTG TGG CAC TGG ATC AAT GAG GCT TGT GGC CGC      785
Ala Leu Thr Ala Asn Leu Trp His Trp Ile Asn Glu Ala Cys Gly Arg
             220                 225                 230

CTA AGT GGA GAT AAG GAG TCC TCA GGT GAC AGT TGT GTC AGT ACA CAC      833
Leu Ser Gly Asp Lys Glu Ser Ser Gly Asp Ser Cys Val Ser Thr His
         235                 240                 245

ACG GCA AAC TTT GGT CAG CAG GGA GCA TGT GAA GGT GTC TTA CTG CTG      881
Thr Ala Asn Phe Gly Gln Gln Gly Ala Cys Glu Gly Val Leu Leu Leu
250                 255                 260

ACT CTG GAG GAG AAG ACA TTT CCA GAA GAT ATG TGC TAC CCA GAT CAA      929
Thr Leu Glu Glu Lys Thr Phe Pro Glu Asp Met Cys Tyr Pro Asp Gln
265                 270                 275

GGT GGT GTC TGT CAG GGC ACG TGT GTA GGA GGT GGT CCC TAC GCA CAA      977
Gly Gly Val Cys Gln Gly Thr Cys Val Gly Gly Gly Pro Tyr Ala Gln
280                 285                 290                 295

GGC GAA GAT GCC AGG ATG CTC TCA TTG GTC AGC AAG ACC GAG ATA GAG     1025
Gly Glu Asp Ala Arg Met Leu Ser Leu Val Ser Lys Thr Glu Ile Glu
             300                 305                 310

GAA GAC AGC TTC AGA CAG ATG CCC ACA GAA GAT GAA TAC ATG GAC AGG     1073
```

```
Glu Asp Ser Phe Arg Gln Met Pro Thr Glu Asp Glu Tyr Met Asp Arg
            315                 320                 325

CCC TCC CAG CCC ACA GAC CAG TTA CTG TTC CTC ACT GAG CCT GGA AGC       1121
Pro Ser Gln Pro Thr Asp Gln Leu Leu Phe Leu Thr Glu Pro Gly Ser
            330                 335                 340

AAA TCC ACA CCT CCT TTC TCT GAA CCC CTG GAG GTG GGG GAG AAT GAC       1169
Lys Ser Thr Pro Pro Phe Ser Glu Pro Leu Glu Val Gly Glu Asn Asp
            345                 350                 355

AGT TTA AGC CAG TGC TTC ACG GGA ACA CAG AGC ACA GTG GGT TCA GAA       1217
Ser Leu Ser Gln Cys Phe Thr Gly Thr Gln Ser Thr Val Gly Ser Glu
360                     365                 370                 375

AGC TGC AAC TGC ACT GAG CCC CTG TGC AGG ACT GAT TGG ACT CCC ATG       1265
Ser Cys Asn Cys Thr Glu Pro Leu Cys Arg Thr Asp Trp Thr Pro Met
                    380                 385                 390

TCC TCT GAA AAC TAC TTG CAA AAA GAG GTG GAC AGT GGC CAT TGC CCG       1313
Ser Ser Glu Asn Tyr Leu Gln Lys Glu Val Asp Ser Gly His Cys Pro
            395                 400                 405

CAC TGG GCA GCC AGC CCC AGC CCC AAC TGG GCA GAT GTC TGC ACA GGC       1361
His Trp Ala Ala Ser Pro Ser Pro Asn Trp Ala Asp Val Cys Thr Gly
            410                 415                 420

TGC CGG AAC CCT CCT GGG GAG GAC TGT GAA CCC CTC GTG GGT TCC CCA       1409
Cys Arg Asn Pro Pro Gly Glu Asp Cys Glu Pro Leu Val Gly Ser Pro
            425                 430                 435

AAA CGT GGA CCC TTG CCC CAG TGC GCC TAT GGC ATG GGC CTT CCC CCT       1457
Lys Arg Gly Pro Leu Pro Gln Cys Ala Tyr Gly Met Gly Leu Pro Pro
440                     445                 450                 455

GAA GAA GAA GCC AGC AGG ACG GAG GCC AGA GAC CAG CCC GAG GAT GGG       1505
Glu Glu Glu Ala Ser Arg Thr Glu Ala Arg Asp Gln Pro Glu Asp Gly
                    460                 465                 470

GCT GAT GGG AGG CTC CCA AGC TCA GCG AGG GCA GGT GCC GGG TCT GGA       1553
Ala Asp Gly Arg Leu Pro Ser Ser Ala Arg Ala Gly Ala Gly Ser Gly
            475                 480                 485

AGC TCC CCT GGT GGC CAG TCC CCT GCA TCT GGA AAT GTG ACT GGA AAC       1601
Ser Ser Pro Gly Gly Gln Ser Pro Ala Ser Gly Asn Val Thr Gly Asn
            490                 495                 500

AGT AAC TCC ACG TTC ATC TCC AGC GGG CAG GTG ATG AAC TTC AAG GGC       1649
Ser Asn Ser Thr Phe Ile Ser Ser Gly Gln Val Met Asn Phe Lys Gly
505                     510                 515

GAC ATC ATC GTG GTC TAC GTC AGC CAG ACC TCG CAG GAG GGC GCG GCG       1697
Asp Ile Ile Val Val Tyr Val Ser Gln Thr Ser Gln Glu Gly Ala Ala
520                     525                 530                 535

GCG GCT GCG GAG CCC ATG GGC CGC CCG GTG CAG GAG GAG ACC CTG GCG       1745
Ala Ala Ala Glu Pro Met Gly Arg Pro Val Gln Glu Glu Thr Leu Ala
                    540                 545                 550

CGC CGA GAC TCC TTC GCG GGG AAC GGC CCG CGC TTC CCG GAC CCG TGC       1793
Arg Arg Asp Ser Phe Ala Gly Asn Gly Pro Arg Phe Pro Asp Pro Cys
            555                 560                 565

GGC GGC CCC GAG GGG CTG CGG GAG CCG GAG AAG GCC TCG AGG CCG GTG       1841
Gly Gly Pro Glu Gly Leu Arg Glu Pro Glu Lys Ala Ser Arg Pro Val
            570                 575                 580

CAG GAG CAA GGC GGG GCC AAG GCT TGA GCGCCCCCCA TGGCTGGGAG             1888
Gln Glu Gln Gly Gly Ala Lys Ala
585                     590

CCCGAAGCTC GGAGCCAGGG CTCGCGAGGG CAGCACCGCA GCCTCTGCCC CAGCCCCGGC     1948

CACCCAGGGA TCGATCGGTA CAGTCGAGGA AGACCACCCG GCATTCTCTG CCCACTTTGC     2008

CTTCCAGGAA ATGGGCTTTT CAGGAAGTGA ATTGATGAGG ACTGTCCCCA TGCCCACGGA     2068

TGCTCAGCAG CCCGCCGCAC TGGGGCAGAT GTCTCCCCTG CCACTCCTCA AACTCGCAGC     2128
```

-continued

```
AGTAATTTGT GGCACTATGA CAGCTATTTT TATGACTATC CTGTTCTGTG GGGGGGGGGT    2188

CTATGTTTTC CCCCCATATT TGTATTCCTT TTCATAACTT TTCTTGATAT CTTTCCTCCC    2248

TCTTTTTTAA TGTAAAGGTT TTCTCAAAAA TTCTCCTAAA GGTGAGGGTC TCTTTCTTTT    2308

CTCTTTTCCT TTTTTTTTTC TTTTTTTGGC AACCTGGCTC TGGCCCAGGC TAGAGTGCAG    2368

TGGTGCGATT ATAGCCCGGT GCAGCCTCTA ACTCCTGGGC TCAAGCAATC CAAGTGATCC    2428

TCCCACCTCA ACCTTCGGAG TAGCTGGGAT CACAGCTGCA GGCCACGCCC AGCTTCCTCC    2488

CCCCGACTCC CCCCCCCCAG AGACACGGTC CCACCATGTT ACCCAGCCTG GTCTCAAACT    2548

CCCCAGCTAA AGCAGTCCTC CAGCCTCGGC CTCCCAAAGT ACTGGGATTA CAGGCGTGAG    2608

CCCCCACGCT GGCCTGCTTT ACGTATTTTC TTTTGTGCCC CTGCTCACAG TGTTTTAGAG    2668

ATGGCTTTCC CAGTGTGTGT TCATTGTAAA CACTTTTGGG AAAGGGCTAA ACATGTGAGG    2728

CCTGGAGATA GTTGCTAAGT TGCTAGGAAC ATGTGGTGGG ACTTTCATAT TCTGAAAAAT    2788

GTTCTATATT CTCATTTTTC TAAAAGAAAG AAAAAAGGAA ACCCGATTTA TTTCTCCTGA    2848

ATCTTTTTAA GTTTGTGTCG TTCCTTAAGC AGAACTAAGC TCAGTATGTG ACCTTACCCG    2908

CTAGGTGGTT AATTTATCCA TGCTGGCAGA GGCACTCAGG TACTTGGTAA GCAAATTTCT    2968

AAAACTCCAA GTTGCTGCAG CTTGGCATTC TTCTTATTCT AGAGGTCTCT CTGGAAAAGA    3028

TGGAGAAAAT GAACAGGACA TGGGGCTCCT GGAAAGAAAG GGCCCGGGAA GTTCAAGGAA    3088

GAATAAAGTT GAAATTTTAA AAAAAA                                        3115
```

(2) INFORMATION FOR SEQ ID NO:2:

(i) SEQUENCE CHARACTERISTICS:
        (A) LENGTH: 591 amino acids
        (B) TYPE: amino acid
        (D) TOPOLOGY: linear (ii) MOLECULE TYPE: protein (xi) SEQUENCE DESCRIPTION: SEQ ID NO:2:

```
Val Ala Leu Gln Ile Ala Pro Pro Cys Thr Ser Glu Lys His Tyr Glu
 1               5                  10                  15

His Leu Gly Arg Cys Cys Asn Lys Cys Glu Pro Gly Lys Tyr Met Ser
            20                  25                  30

Ser Lys Cys Thr Thr Thr Ser Asp Ser Val Cys Leu Pro Cys Gly Pro
        35                  40                  45

Asp Glu Tyr Leu Asp Ser Trp Asn Glu Glu Asp Lys Cys Leu Leu His
    50                  55                  60

Lys Val Cys Asp Thr Gly Lys Ala Leu Val Ala Val Ala Gly Asn
65                  70                  75                  80

Ser Thr Thr Pro Arg Arg Cys Ala Cys Thr Ala Gly Tyr His Trp Ser
                85                  90                  95

Gln Asp Cys Glu Cys Cys Arg Arg Asn Thr Glu Cys Ala Pro Gly Leu
            100                 105                 110

Gly Ala Gln His Pro Leu Gln Leu Asn Lys Asp Thr Val Cys Lys Pro
        115                 120                 125

Cys Leu Ala Gly Tyr Phe Ser Asp Ala Phe Ser Ser Thr Asp Lys Cys
    130                 135                 140

Arg Pro Trp Thr Asn Cys Thr Phe Leu Gly Lys Arg Val Glu His His
145                 150                 155                 160

Gly Thr Glu Lys Ser Asp Ala Val Cys Ser Ser Ser Leu Pro Ala Arg
                165                 170                 175
```

```
Lys Pro Pro Asn Glu Pro His Val Tyr Leu Pro Gly Leu Ile Ile Leu
            180                 185                 190
Leu Leu Phe Ala Ser Val Ala Leu Val Ala Ala Ile Ile Phe Gly Val
        195                 200                 205
Cys Tyr Arg Lys Lys Gly Lys Ala Leu Thr Ala Asn Leu Trp His Trp
    210                 215                 220
Ile Asn Glu Ala Cys Gly Arg Leu Ser Gly Asp Lys Glu Ser Ser Gly
225                 230                 235                 240
Asp Ser Cys Val Ser Thr His Thr Ala Asn Phe Gly Gln Gln Gly Ala
                245                 250                 255
Cys Glu Gly Val Leu Leu Leu Thr Leu Glu Glu Lys Thr Phe Pro Glu
                260                 265                 270
Asp Met Cys Tyr Pro Asp Gln Gly Val Cys Gln Gly Thr Cys Val
            275                 280                 285
Gly Gly Gly Pro Tyr Ala Gln Gly Glu Asp Ala Arg Met Leu Ser Leu
        290                 295                 300
Val Ser Lys Thr Glu Ile Glu Glu Asp Ser Phe Arg Gln Met Pro Thr
305                 310                 315                 320
Glu Asp Glu Tyr Met Asp Arg Pro Ser Gln Pro Thr Asp Gln Leu Leu
                325                 330                 335
Phe Leu Thr Glu Pro Gly Ser Lys Ser Thr Pro Pro Phe Ser Glu Pro
            340                 345                 350
Leu Glu Val Gly Glu Asn Asp Ser Leu Ser Gln Cys Phe Thr Gly Thr
        355                 360                 365
Gln Ser Thr Val Gly Ser Glu Ser Cys Asn Cys Thr Glu Pro Leu Cys
    370                 375                 380
Arg Thr Asp Trp Thr Pro Met Ser Ser Glu Asn Tyr Leu Gln Lys Glu
385                 390                 395                 400
Val Asp Ser Gly His Cys Pro His Trp Ala Ala Ser Pro Ser Pro Asn
                405                 410                 415
Trp Ala Asp Val Cys Thr Gly Cys Arg Asn Pro Pro Gly Glu Asp Cys
            420                 425                 430
Glu Pro Leu Val Gly Ser Pro Lys Arg Gly Pro Leu Pro Gln Cys Ala
        435                 440                 445
Tyr Gly Met Gly Leu Pro Pro Glu Glu Glu Ala Ser Arg Thr Glu Ala
    450                 455                 460
Arg Asp Gln Pro Glu Asp Gly Ala Asp Gly Arg Leu Pro Ser Ser Ala
465                 470                 475                 480
Arg Ala Gly Ala Gly Ser Ser Pro Gly Gly Gln Ser Pro Ala
                485                 490                 495
Ser Gly Asn Val Thr Gly Asn Ser Asn Ser Thr Phe Ile Ser Ser Gly
            500                 505                 510
Gln Val Met Asn Phe Lys Gly Asp Ile Ile Val Val Tyr Val Ser Gln
        515                 520                 525
Thr Ser Gln Glu Gly Ala Ala Ala Ala Glu Pro Met Gly Arg Pro
    530                 535                 540
Val Gln Glu Glu Thr Leu Ala Arg Arg Asp Ser Phe Ala Gly Asn Gly
545                 550                 555                 560
Pro Arg Phe Pro Asp Pro Cys Gly Gly Pro Glu Gly Leu Arg Glu Pro
                565                 570                 575
Glu Lys Ala Ser Arg Pro Val Gln Glu Gln Gly Gly Ala Lys Ala
            580                 585                 590
```

-continued (2) INFORMATION FOR SEQ ID NO:3:

(i) SEQUENCE CHARACTERISTICS:
        (A) LENGTH: 1391 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (vi) ORIGINAL SOURCE:
        (A) ORGANISM: HOMO SAPIENS (vii) IMMEDIATE SOURCE:
        (A) LIBRARY: BONE-MARROW DERIVED DENDRITIC CELLS
        (B) CLONE: 9D-15C (ix) FEATURE:
        (A) NAME/KEY: CDS
        (B) LOCATION: 39..1391

(xi) SEQUENCE DESCRIPTION: SEQ ID NO:3:

```
CCGCTGAGGC CGCGGCGCCC GCCAGCCTGT CCCGCGCC ATG GCC CCG CGC GCC          53
                                           Met Ala Pro Arg Ala
                                           1               5

CGG CGG CGC CGC CCG CTG TTC GCG CTG CTG CTC TGC GCG CTG CTC          101
Arg Arg Arg Arg Pro Leu Phe Ala Leu Leu Leu Cys Ala Leu Leu
            10              15                  20

GCC CGG CTG CAG GTG GCT TTG CAG ATC GCT CCT CCA TGT ACC AGT GAG      149
Ala Arg Leu Gln Val Ala Leu Gln Ile Ala Pro Pro Cys Thr Ser Glu
        25                  30                  35

AAG CAT TAT GAG CAT CTG GGA CGG TGC TGT AAC AAA TGT GAA CCA GGA      197
Lys His Tyr Glu His Leu Gly Arg Cys Cys Asn Lys Cys Glu Pro Gly
            40                  45              50

AAG TAC ATG TCT TCT AAA TGC ACT ACT ACC TCT GAC AGT GTA TGT CTG      245
Lys Tyr Met Ser Ser Lys Cys Thr Thr Thr Ser Asp Ser Val Cys Leu
        55                  60                  65

CCC TGT GGC CCG GAT GAA TAC TTG GAT AGC TGG AAT GAA GAA GAT AAA      293
Pro Cys Gly Pro Asp Glu Tyr Leu Asp Ser Trp Asn Glu Glu Asp Lys
70                  75                  80                  85

TGC TTG CTG CAT AAA GTT TGT GAT ACA GGC AAG GCC CTG GTG GCC GTG      341
Cys Leu Leu His Lys Val Cys Asp Thr Gly Lys Ala Leu Val Ala Val
                90                  95                  100

GTC GCC GGC AAC AGC ACG ACC CCC CGG CGC TGC GCG TGC ACG GCT GGG      389
Val Ala Gly Asn Ser Thr Thr Pro Arg Arg Cys Ala Cys Thr Ala Gly
            105                 110                 115

TAC CAC TGG AGC CAG GAC TGC GAG TGC TGC CGC CGC AAC ACC GAG TGC      437
Tyr His Trp Ser Gln Asp Cys Glu Cys Cys Arg Arg Asn Thr Glu Cys
        120                 125                 130

GCG CCG GGC CTG GGC GCC CAG CAC CCG TTG CAG CTC AAC AAG GAC ACA      485
Ala Pro Gly Leu Gly Ala Gln His Pro Leu Gln Leu Asn Lys Asp Thr
    135                 140                 145

GTG TGC AAA CCT TGC CTT GCA GGC TAC TTC TCT GAT GCC TTT TCC TCC      533
Val Cys Lys Pro Cys Leu Ala Gly Tyr Phe Ser Asp Ala Phe Ser Ser
150                 155                 160                 165

ACG GAC AAA TGC AGA CCC TGG ACC AAC TGT ACC TTC CTT GGA AAG AGA      581
Thr Asp Lys Cys Arg Pro Trp Thr Asn Cys Thr Phe Leu Gly Lys Arg
                170                 175                 180

GTA GAA CAT CAT GGG ACA GAG AAA TCC GAT GCG GTT TGC AGT TCT TCT      629
Val Glu His His Gly Thr Glu Lys Ser Asp Ala Val Cys Ser Ser Ser
            185                 190                 195
```

```
CTG CCA GCT AGA AAA CCA CCA AAT GAA CCC CAT GTT TAC TTG CCC GGT        677
Leu Pro Ala Arg Lys Pro Pro Asn Glu Pro His Val Tyr Leu Pro Gly
        200                 205                 210

TTA ATA ATT CTG CTT CTC TTC GCG TCT GTG GCC CTG GTG GCT GCC ATC        725
Leu Ile Ile Leu Leu Leu Phe Ala Ser Val Ala Leu Val Ala Ala Ile
    215                 220                 225

ATC TTT GGC GTT TGC TAT AGG AAA AAA GGG AAA GCA CTC ACA GCT AAT        773
Ile Phe Gly Val Cys Tyr Arg Lys Lys Gly Lys Ala Leu Thr Ala Asn
230                 235                 240                 245

TTG TGG CAC TGG ATC AAT GAG GCT TGT GGC CGC CTA AGT GGA GAT AAG        821
Leu Trp His Trp Ile Asn Glu Ala Cys Gly Arg Leu Ser Gly Asp Lys
                250                 255                 260

GAG TCC TCA GGT GAC AGT TGT GTC AGT ACA CAC ACG GCA AAC TTT GGT        869
Glu Ser Ser Gly Asp Ser Cys Val Ser Thr His Thr Ala Asn Phe Gly
            265                 270                 275

CAG CAG GGA GCA TGT GAA GGT GTC TTA CTG CTG ACT CTG GAG GAG AAG        917
Gln Gln Gly Ala Cys Glu Gly Val Leu Leu Leu Thr Leu Glu Glu Lys
        280                 285                 290

ACA TTT CCA GAA GAT ATG TGC TAC CCA GAT CAA GGT GGT GTC TGT CAG        965
Thr Phe Pro Glu Asp Met Cys Tyr Pro Asp Gln Gly Gly Val Cys Gln
    295                 300                 305

GGC ACG TGT GTA GGA GGT GGT CCC TAC GCA CAA GGC GAA GAT GCC AGG       1013
Gly Thr Cys Val Gly Gly Gly Pro Tyr Ala Gln Gly Glu Asp Ala Arg
310                 315                 320                 325

ATG CTC TCA TTG GTC AGC AAG ACC GAG ATA GAG GAA GAC AGC TTC AGA       1061
Met Leu Ser Leu Val Ser Lys Thr Glu Ile Glu Glu Asp Ser Phe Arg
                330                 335                 340

CAG ATG CCC ACA GAA GAT GAA TAC ATG GAC AGG CCC TCC CAG CCC ACA       1109
Gln Met Pro Thr Glu Asp Glu Tyr Met Asp Arg Pro Ser Gln Pro Thr
            345                 350                 355

GAC CAG TTA CTG TTC CTC ACT GAG CCT GGA AGC AAA TCC ACA CCT CCT       1157
Asp Gln Leu Leu Phe Leu Thr Glu Pro Gly Ser Lys Ser Thr Pro Pro
        360                 365                 370

TTC TCT GAA CCC CTG GAG GTG GGG GAG AAT GAC AGT TTA AGC CAG TGC       1205
Phe Ser Glu Pro Leu Glu Val Gly Glu Asn Asp Ser Leu Ser Gln Cys
    375                 380                 385

TTC ACG GGA ACA CAG AGC ACA GTG GGT TCA GAA AGC TGC AAC TGC ACT       1253
Phe Thr Gly Thr Gln Ser Thr Val Gly Ser Glu Ser Cys Asn Cys Thr
390                 395                 400                 405

GAG CCC CTG TGC AGG ACT GAT TGG ACT CCC ATG TCC TCT GAA AAC TAC       1301
Glu Pro Leu Cys Arg Thr Asp Trp Thr Pro Met Ser Ser Glu Asn Tyr
                410                 415                 420

TTG CAA AAA GAG GTG GAC AGT GGC CAT TGC CCG CAC TGG GCA GCC AGC       1349
Leu Gln Lys Glu Val Asp Ser Gly His Cys Pro His Trp Ala Ala Ser
            425                 430                 435

CCC AGC CCC AAC TGG GCA GAT GTC TGC ACA GGC TGC CGG AAC              1391
Pro Ser Pro Asn Trp Ala Asp Val Cys Thr Gly Cys Arg Asn
        440                 445                 450

(2) INFORMATION FOR SEQ ID NO:4:

(i) SEQUENCE CHARACTERISTICS:
        (A) LENGTH: 451 amino acids
        (B) TYPE: amino acid
        (D) TOPOLOGY: linear (ii) MOLECULE TYPE: protein (xi) SEQUENCE DESCRIPTION: SEQ ID NO:4:

Met Ala Pro Arg Ala Arg Arg Arg Pro Leu Phe Ala Leu Leu Leu
 1               5                  10                  15
```

```
Leu Cys Ala Leu Leu Ala Arg Leu Gln Val Ala Leu Gln Ile Ala Pro
            20                  25                  30
Pro Cys Thr Ser Glu Lys His Tyr Glu His Leu Gly Arg Cys Cys Asn
            35                  40                  45
Lys Cys Glu Pro Gly Lys Tyr Met Ser Ser Lys Cys Thr Thr Thr Ser
            50                  55                  60
Asp Ser Val Cys Leu Pro Cys Gly Pro Asp Glu Tyr Leu Asp Ser Trp
 65                  70                  75                  80
Asn Glu Glu Asp Lys Cys Leu Leu His Lys Val Cys Asp Thr Gly Lys
                85                  90                  95
Ala Leu Val Ala Val Ala Gly Asn Ser Thr Thr Pro Arg Arg Cys
                100                 105                 110
Ala Cys Thr Ala Gly Tyr His Trp Ser Gln Asp Cys Glu Cys Cys Arg
            115                 120                 125
Arg Asn Thr Glu Cys Ala Pro Gly Leu Gly Ala Gln His Pro Leu Gln
 130                 135                 140
Leu Asn Lys Asp Thr Val Cys Lys Pro Cys Leu Ala Gly Tyr Phe Ser
 145                 150                 155                 160
Asp Ala Phe Ser Ser Thr Asp Lys Cys Arg Pro Trp Thr Asn Cys Thr
                165                 170                 175
Phe Leu Gly Lys Arg Val Glu His His Gly Thr Glu Lys Ser Asp Ala
                180                 185                 190
Val Cys Ser Ser Ser Leu Pro Ala Arg Lys Pro Pro Asn Glu Pro His
                195                 200                 205
Val Tyr Leu Pro Gly Leu Ile Ile Leu Leu Leu Phe Ala Ser Val Ala
 210                 215                 220
Leu Val Ala Ala Ile Ile Phe Gly Val Cys Tyr Arg Lys Lys Gly Lys
 225                 230                 235                 240
Ala Leu Thr Ala Asn Leu Trp His Trp Ile Asn Glu Ala Cys Gly Arg
                245                 250                 255
Leu Ser Gly Asp Lys Glu Ser Ser Gly Asp Ser Cys Val Ser Thr His
                260                 265                 270
Thr Ala Asn Phe Gly Gln Gln Gly Ala Cys Glu Gly Val Leu Leu Leu
                275                 280                 285
Thr Leu Glu Glu Lys Thr Phe Pro Glu Asp Met Cys Tyr Pro Asp Gln
 290                 295                 300
Gly Gly Val Cys Gln Gly Thr Cys Val Gly Gly Pro Tyr Ala Gln
 305                 310                 315                 320
Gly Glu Asp Ala Arg Met Leu Ser Leu Val Ser Lys Thr Glu Ile Glu
                325                 330                 335
Glu Asp Ser Phe Arg Gln Met Pro Thr Glu Asp Glu Tyr Met Asp Arg
                340                 345                 350
Pro Ser Gln Pro Thr Asp Gln Leu Leu Phe Leu Thr Glu Pro Gly Ser
                355                 360                 365
Lys Ser Thr Pro Pro Phe Ser Glu Pro Leu Glu Val Gly Glu Asn Asp
                370                 375                 380
Ser Leu Ser Gln Cys Phe Thr Gly Thr Gln Ser Thr Val Gly Ser Glu
 385                 390                 395                 400
Ser Cys Asn Cys Thr Glu Pro Leu Cys Arg Thr Asp Trp Thr Pro Met
                405                 410                 415
Ser Ser Glu Asn Tyr Leu Gln Lys Glu Val Asp Ser Gly His Cys Pro
                420                 425                 430
His Trp Ala Ala Ser Pro Ser Pro Asn Trp Ala Asp Val Cys Thr Gly
```

-continued

```
                435                 440                 445
Cys Arg Asn
    450

(2) INFORMATION FOR SEQ ID NO:5:

(i) SEQUENCE CHARACTERISTICS:
        (A) LENGTH: 3136 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (vi) ORIGINAL SOURCE:
        (A) ORGANISM: HOMO SAPIENS (vii) IMMEDIATE SOURCE:
        (A) LIBRARY: BONE-MARROW DERIVED DENDRITIC CELLS
        (B) CLONE: FULL LENGTH RANK (ix) FEATURE:
        (A) NAME/KEY: CDS
        (B) LOCATION: 39..1886

(xi) SEQUENCE DESCRIPTION: SEQ ID NO:5:

CCGCTGAGGC CGCGGCGCCC GCCAGCCTGT CCCGCGCC ATG GCC CCG CGC GCC         53
                                          Met Ala Pro Arg Ala
                                            1               5

CGG CGG CGC CGC CCG CTG TTC GCG CTG CTG CTG CTC TGC GCG CTG CTC      101
Arg Arg Arg Arg Pro Leu Phe Ala Leu Leu Leu Leu Cys Ala Leu Leu
             10                  15                  20

GCC CGG CTG CAG GTG GCT TTG CAG ATC GCT CCT CCA TGT ACC AGT GAG      149
Ala Arg Leu Gln Val Ala Leu Gln Ile Ala Pro Pro Cys Thr Ser Glu
         25                  30                  35

AAG CAT TAT GAG CAT CTG GGA CGG TGC TGT AAC AAA TGT GAA CCA GGA      197
Lys His Tyr Glu His Leu Gly Arg Cys Cys Asn Lys Cys Glu Pro Gly
     40                  45                  50

AAG TAC ATG TCT TCT AAA TGC ACT ACT ACC TCT GAC AGT GTA TGT CTG      245
Lys Tyr Met Ser Ser Lys Cys Thr Thr Thr Ser Asp Ser Val Cys Leu
 55                  60                  65

CCC TGT GGC CCG GAT GAA TAC TTG GAT AGC TGG AAT GAA GAA GAT AAA      293
Pro Cys Gly Pro Asp Glu Tyr Leu Asp Ser Trp Asn Glu Glu Asp Lys
 70                  75                  80                  85

TGC TTG CTG CAT AAA GTT TGT GAT ACA GGC AAG GCC CTG GTG GCC GTG      341
Cys Leu Leu His Lys Val Cys Asp Thr Gly Lys Ala Leu Val Ala Val
             90                  95                 100

GTC GCC GGC AAC AGC ACG ACC CCC CGG CGC TGC GCG TGC ACG GCT GGG      389
Val Ala Gly Asn Ser Thr Thr Pro Arg Arg Cys Ala Cys Thr Ala Gly
            105                 110                 115

TAC CAC TGG AGC CAG GAC TGC GAG TGC TGC CGC CGC AAC ACC GAG TGC      437
Tyr His Trp Ser Gln Asp Cys Glu Cys Cys Arg Arg Asn Thr Glu Cys
            120                 125                 130

GCG CCG GGC CTG GGC GCC CAG CAC CCG TTG CAG CTC AAC AAG GAC ACA      485
Ala Pro Gly Leu Gly Ala Gln His Pro Leu Gln Leu Asn Lys Asp Thr
        135                 140                 145

GTG TGC AAA CCT TGC CTT GCA GGC TAC TTC TCT GAT GCC TTT TCC TCC      533
Val Cys Lys Pro Cys Leu Ala Gly Tyr Phe Ser Asp Ala Phe Ser Ser
150                 155                 160                 165

ACG GAC AAA TGC AGA CCC TGG ACC AAC TGT ACC TTC CTT GGA AAG AGA      581
Thr Asp Lys Cys Arg Pro Trp Thr Asn Cys Thr Phe Leu Gly Lys Arg
```

```
                       170              175              180
GTA GAA CAT CAT GGG ACA GAG AAA TCC GAT GCG GTT TGC AGT TCT TCT          629
Val Glu His His Gly Thr Glu Lys Ser Asp Ala Val Cys Ser Ser Ser
            185              190              195

CTG CCA GCT AGA AAA CCA CCA AAT GAA CCC CAT GTT TAC TTG CCC GGT          677
Leu Pro Ala Arg Lys Pro Pro Asn Glu Pro His Val Tyr Leu Pro Gly
            200              205              210

TTA ATA ATT CTG CTT CTC TTC GCG TCT GTG GCC CTG GTG GCT GCC ATC          725
Leu Ile Ile Leu Leu Leu Phe Ala Ser Val Ala Leu Val Ala Ala Ile
    215              220              225

ATC TTT GGC GTT TGC TAT AGG AAA AAA GGG AAA GCA CTC ACA GCT AAT          773
Ile Phe Gly Val Cys Tyr Arg Lys Lys Gly Lys Ala Leu Thr Ala Asn
230              235              240              245

TTG TGG CAC TGG ATC AAT GAG GCT TGT GGC CGC CTA AGT GGA GAT AAG          821
Leu Trp His Trp Ile Asn Glu Ala Cys Gly Arg Leu Ser Gly Asp Lys
                250              255              260

GAG TCC TCA GGT GAC AGT TGT GTC AGT ACA CAC ACG GCA AAC TTT GGT          869
Glu Ser Ser Gly Asp Ser Cys Val Ser Thr His Thr Ala Asn Phe Gly
            265              270              275

CAG CAG GGA GCA TGT GAA GGT GTC TTA CTG CTG ACT CTG GAG GAG AAG          917
Gln Gln Gly Ala Cys Glu Gly Val Leu Leu Leu Thr Leu Glu Glu Lys
            280              285              290

ACA TTT CCA GAA GAT ATG TGC TAC CCA GAT CAA GGT GGT GTC TGT CAG          965
Thr Phe Pro Glu Asp Met Cys Tyr Pro Asp Gln Gly Gly Val Cys Gln
    295              300              305

GGC ACG TGT GTA GGA GGT GGT CCC TAC GCA CAA GGC GAA GAT GCC AGG         1013
Gly Thr Cys Val Gly Gly Gly Pro Tyr Ala Gln Gly Glu Asp Ala Arg
310              315              320              325

ATG CTC TCA TTG GTC AGC AAG ACC GAG ATA GAG GAA GAC AGC TTC AGA         1061
Met Leu Ser Leu Val Ser Lys Thr Glu Ile Glu Glu Asp Ser Phe Arg
                330              335              340

CAG ATG CCC ACA GAA GAT GAA TAC ATG GAC AGG CCC TCC CAG CCC ACA         1109
Gln Met Pro Thr Glu Asp Glu Tyr Met Asp Arg Pro Ser Gln Pro Thr
            345              350              355

GAC CAG TTA CTG TTC CTC ACT GAG CCT GGA AGC AAA TCC ACA CCT CCT         1157
Asp Gln Leu Leu Phe Leu Thr Glu Pro Gly Ser Lys Ser Thr Pro Pro
            360              365              370

TTC TCT GAA CCC CTG GAG GTG GGG GAG AAT GAC AGT TTA AGC CAG TGC         1205
Phe Ser Glu Pro Leu Glu Val Gly Glu Asn Asp Ser Leu Ser Gln Cys
    375              380              385

TTC ACG GGA ACA CAG AGC ACA GTG GGT TCA GAA AGC TGC AAC TGC ACT         1253
Phe Thr Gly Thr Gln Ser Thr Val Gly Ser Glu Ser Cys Asn Cys Thr
390              395              400              405

GAG CCC CTG TGC AGG ACT GAT TGG ACT CCC ATG TCC TCT GAA AAC TAC         1301
Glu Pro Leu Cys Arg Thr Asp Trp Thr Pro Met Ser Ser Glu Asn Tyr
                410              415              420

TTG CAA AAA GAG GTG GAC AGT GGC CAT TGC CCG CAC TGG GCA GCC AGC         1349
Leu Gln Lys Glu Val Asp Ser Gly His Cys Pro His Trp Ala Ala Ser
            425              430              435

CCC AGC CCC AAC TGG GCA GAT GTC TGC ACA GGC TGC CGG AAC CCT CCT         1397
Pro Ser Pro Asn Trp Ala Asp Val Cys Thr Gly Cys Arg Asn Pro Pro
            440              445              450

GGG GAG GAC TGT GAA CCC CTC GTG GGT TCC CCA AAA CGT GGA CCC TTG         1445
Gly Glu Asp Cys Glu Pro Leu Val Gly Ser Pro Lys Arg Gly Pro Leu
455              460              465

CCC CAG TGC GCC TAT GGC ATG GGC CTT CCC CCT GAA GAA GAA GCC AGC         1493
Pro Gln Cys Ala Tyr Gly Met Gly Leu Pro Pro Glu Glu Glu Ala Ser
470              475              480              485

AGG ACG GAG GCC AGA GAC CAG CCC GAG GAT GGG GCT GAT GGG AGG CTC         1541
```

```
Arg Thr Glu Ala Arg Asp Gln Pro Glu Asp Gly Ala Asp Gly Arg Leu
                490                 495                 500
CCA AGC TCA GCG AGG GCA GGT GCC GGG TCT GGA AGC TCC CCT GGT GGC        1589
Pro Ser Ser Ala Arg Ala Gly Ala Gly Ser Gly Ser Ser Pro Gly Gly
            505                 510                 515
CAG TCC CCT GCA TCT GGA AAT GTG ACT GGA AAC AGT AAC TCC ACG TTC        1637
Gln Ser Pro Ala Ser Gly Asn Val Thr Gly Asn Ser Asn Ser Thr Phe
        520                 525                 530
ATC TCC AGC GGG CAG GTG ATG AAC TTC AAG GGC GAC ATC ATC GTG GTC        1685
Ile Ser Ser Gly Gln Val Met Asn Phe Lys Gly Asp Ile Ile Val Val
    535                 540                 545
TAC GTC AGC CAG ACC TCG CAG GAG GGC GCG GCG GCG GCT GCG GAG CCC        1733
Tyr Val Ser Gln Thr Ser Gln Glu Gly Ala Ala Ala Ala Ala Glu Pro
550                 555                 560                 565
ATG GGC CGC CCG GTG CAG GAG GAG ACC CTG GCG CGC CGA GAC TCC TTC        1781
Met Gly Arg Pro Val Gln Glu Glu Thr Leu Ala Arg Arg Asp Ser Phe
                570                 575                 580
GCG GGG AAC GGC CCG CGC TTC CCG GAC CCG TGC GGC GGC CCC GAG GGG        1829
Ala Gly Asn Gly Pro Arg Phe Pro Asp Pro Cys Gly Gly Pro Glu Gly
            585                 590                 595
CTG CGG GAG CCG GAG AAG GCC TCG AGG CCG GTG CAG GAG CAA GGC GGG        1877
Leu Arg Glu Pro Glu Lys Ala Ser Arg Pro Val Gln Glu Gln Gly Gly
        600                 605                 610
GCC AAG GCT TGAGCGCCCC CCATGGCTGG GAGCCCGAAG CTCGGAGCCA                1926
Ala Lys Ala
        615
GGGCTCGCGA GGGCAGCACC GCAGCCTCTG CCCCAGCCCC GGCCACCCAG GGATCGATCG      1986
GTACAGTCGA GGAAGACCAC CCGGCATTCT CTGCCCACTT TGCCTTCCAG GAAATGGGCT      2046
TTTCAGGAAG TGAATTGATG AGGACTGTCC CCATGCCCAC GGATGCTCAG CAGCCCGCCG      2106
CACTGGGGCA GATGTCTCCC CTGCCACTCC TCAAACTCGC AGCAGTAATT TGTGGCACTA      2166
TGACAGCTAT TTTTATGACT ATCCTGTTCT GTGGGGGGGG GGTCTATGTT TTCCCCCCAT      2226
ATTTGTATTC CTTTTCATAA CTTTTCTTGA TATCTTTCCT CCCTCTTTTT TAATGTAAAG      2286
GTTTTCTCAA AAATTCTCCT AAAGGTGAGG GTCTCTTTCT TTTCTCTTTT CCTTTTTTTT      2346
TTCTTTTTTT GGCAACCTGG CTCTGGCCCA GGCTAGAGTG CAGTGGTGCG ATTATAGCCC      2406
GGTGCAGCCT CTAACTCCTG GGCTCAAGCA ATCCAAGTGA TCCTCCCACC TCAACCTTCG      2466
GAGTAGCTGG GATCACAGCT GCAGGCCACG CCCAGCTTCC TCCCCCCGAC TCCCCCCCCC      2526
CAGAGACACG GTCCCACCAT GTTACCCAGC CTGGTCTCAA ACTCCCCAGC TAAAGCAGTC      2586
CTCCAGCCTC GGCCTCCCAA AGTACTGGGA TTACAGGCGT GAGCCCCCAC GCTGGCCTGC      2646
TTTACGTATT TTCTTTTGTG CCCCTGCTCA CAGTGTTTTA GAGATGGCTT TCCCAGTGTG      2706
TGTTCATTGT AAACACTTTT GGGAAAGGGC TAAACATGTG AGGCCTGGAG ATAGTTGCTA      2766
AGTTGCTAGG AACATGTGGT GGGACTTTCA TATTCTGAAA AATGTTCTAT ATTCTCATTT      2826
TTCTAAAAGA AAGAAAAAAG GAAACCCGAT TTATTTCTCC TGAATCTTTT TAAGTTTGTG      2886
TCGTTCCTTA AGCAGAACTA AGCTCAGTAT GTGACCTTAC CCGCTAGGTG GTTAATTTAT      2946
CCATGCTGGC AGAGGCACTC AGGTACTTGG TAAGCAAATT TCTAAAACTC CAAGTTGCTG      3006
CAGCTTGGCA TTCTTCTTAT TCTAGAGGTC TCTCTGGAAA AGATGGAGAA AATGAACAGG      3066
ACATGGGGCT CCTGGAAAGA AAGGGCCCGG GAAGTTCAAG GAAGAATAAA GTTGAAATTT      3126
TAAAAAAAAA                                                            3136
```

(2) INFORMATION FOR SEQ ID NO:6:

(i) SEQUENCE CHARACTERISTICS:
    (A) LENGTH: 616 amino acids
    (B) TYPE: amino acid
    (D) TOPOLOGY: linear (ii) MOLECULE TYPE: protein (xi) SEQUENCE DESCRIPTION: SEQ ID NO:6:

```
Met Ala Pro Arg Ala Arg Arg Arg Pro Leu Phe Ala Leu Leu Leu
 1               5                  10                  15

Leu Cys Ala Leu Leu Ala Arg Leu Gln Val Ala Leu Gln Ile Ala Pro
            20                  25                  30

Pro Cys Thr Ser Glu Lys His Tyr Glu His Leu Gly Arg Cys Cys Asn
            35                  40                  45

Lys Cys Glu Pro Gly Lys Tyr Met Ser Ser Lys Cys Thr Thr Thr Ser
 50                  55                  60

Asp Ser Val Cys Leu Pro Cys Gly Pro Asp Glu Tyr Leu Asp Ser Trp
 65                  70                  75                  80

Asn Glu Glu Asp Lys Cys Leu Leu His Lys Val Cys Asp Thr Gly Lys
                85                  90                  95

Ala Leu Val Ala Val Ala Gly Asn Ser Thr Thr Pro Arg Arg Cys
                100                 105                 110

Ala Cys Thr Ala Gly Tyr His Trp Ser Gln Asp Cys Glu Cys Arg
            115                 120                 125

Arg Asn Thr Glu Cys Ala Pro Gly Leu Gly Ala Gln His Pro Leu Gln
    130                 135                 140

Leu Asn Lys Asp Thr Val Cys Lys Pro Cys Leu Ala Gly Tyr Phe Ser
145                 150                 155                 160

Asp Ala Phe Ser Ser Thr Asp Lys Cys Arg Pro Trp Thr Asn Cys Thr
                165                 170                 175

Phe Leu Gly Lys Arg Val Glu His His Gly Thr Glu Lys Ser Asp Ala
            180                 185                 190

Val Cys Ser Ser Ser Leu Pro Ala Arg Lys Pro Pro Asn Glu Pro His
    195                 200                 205

Val Tyr Leu Pro Gly Leu Ile Ile Leu Leu Leu Phe Ala Ser Val Ala
210                 215                 220

Leu Val Ala Ala Ile Ile Phe Gly Val Cys Tyr Arg Lys Lys Gly Lys
225                 230                 235                 240

Ala Leu Thr Ala Asn Leu Trp His Trp Ile Asn Glu Ala Cys Gly Arg
                245                 250                 255

Leu Ser Gly Asp Lys Glu Ser Ser Gly Asp Ser Cys Val Ser Thr His
            260                 265                 270

Thr Ala Asn Phe Gly Gln Gln Gly Ala Cys Glu Gly Val Leu Leu Leu
    275                 280                 285

Thr Leu Glu Glu Lys Thr Phe Pro Glu Asp Met Cys Tyr Pro Asp Gln
290                 295                 300

Gly Gly Val Cys Gln Gly Thr Cys Val Gly Gly Pro Tyr Ala Gln
305                 310                 315                 320

Gly Glu Asp Ala Arg Met Leu Ser Leu Val Ser Lys Thr Glu Ile Glu
                325                 330                 335

Glu Asp Ser Phe Arg Gln Met Pro Thr Glu Asp Glu Tyr Met Asp Arg
            340                 345                 350

Pro Ser Gln Pro Thr Asp Gln Leu Leu Phe Leu Thr Glu Pro Gly Ser
        355                 360                 365
```

```
Lys Ser Thr Pro Pro Phe Ser Glu Pro Leu Glu Val Gly Glu Asn Asp
    370                 375                 380

Ser Leu Ser Gln Cys Phe Thr Gly Thr Gln Ser Thr Val Gly Ser Glu
385                 390                 395                 400

Ser Cys Asn Cys Thr Glu Pro Leu Cys Arg Thr Asp Trp Thr Pro Met
                405                 410                 415

Ser Ser Glu Asn Tyr Leu Gln Lys Glu Val Asp Ser Gly His Cys Pro
            420                 425                 430

His Trp Ala Ala Ser Pro Ser Pro Asn Trp Ala Asp Val Cys Thr Gly
        435                 440                 445

Cys Arg Asn Pro Pro Gly Glu Asp Cys Glu Pro Leu Val Gly Ser Pro
    450                 455                 460

Lys Arg Gly Pro Leu Pro Gln Cys Ala Tyr Gly Met Gly Leu Pro Pro
465                 470                 475                 480

Glu Glu Glu Ala Ser Arg Thr Glu Ala Arg Asp Gln Pro Glu Asp Gly
                485                 490                 495

Ala Asp Gly Arg Leu Pro Ser Ser Ala Arg Ala Gly Ala Gly Ser Gly
            500                 505                 510

Ser Ser Pro Gly Gly Gln Ser Pro Ala Ser Gly Asn Val Thr Gly Asn
        515                 520                 525

Ser Asn Ser Thr Phe Ile Ser Ser Gly Gln Val Met Asn Phe Lys Gly
        530                 535                 540

Asp Ile Ile Val Val Tyr Val Ser Gln Thr Ser Gln Glu Gly Ala Ala
545                 550                 555                 560

Ala Ala Ala Glu Pro Met Gly Arg Pro Val Gln Glu Glu Thr Leu Ala
                565                 570                 575

Arg Arg Asp Ser Phe Ala Gly Asn Gly Pro Arg Phe Pro Asp Pro Cys
            580                 585                 590

Gly Gly Pro Glu Gly Leu Arg Glu Pro Glu Lys Ala Ser Arg Pro Val
        595                 600                 605

Gln Glu Gln Gly Gly Ala Lys Ala
    610                 615

(2) INFORMATION FOR SEQ ID NO:7:

(i) SEQUENCE CHARACTERISTICS:
        (A) LENGTH: 8 amino acids
        (B) TYPE: amino acid
        (C) STRANDEDNESS: Not Relevant
        (D) TOPOLOGY: linear (ii) MOLECULE TYPE: peptide (vii) IMMEDIATE SOURCE:
        (B) CLONE: FLAG_ peptide (xi) SEQUENCE DESCRIPTION: SEQ ID NO:7:

Asp Tyr Lys Asp Asp Asp Asp Lys
 1               5

(2) INFORMATION FOR SEQ ID NO:8:

(i) SEQUENCE CHARACTERISTICS:
        (A) LENGTH: 232 amino acids
        (B) TYPE: amino acid
        (C) STRANDEDNESS: Not Relevant
        (D) TOPOLOGY: linear (ii) MOLECULE TYPE: protein (vi) ORIGINAL SOURCE:
```

-continued (A) ORGANISM: Human (vii) IMMEDIATE SOURCE:
  (B) CLONE: IgG1 Fc mutein (xi) SEQUENCE DESCRIPTION: SEQ ID NO:8:

Glu Pro Arg Ser Cys Asp Lys Thr His Thr Cys Pro Pro Cys Pro Ala
1               5                   10                  15

Pro Glu Ala Glu Gly Ala Pro Ser Val Phe Leu Phe Pro Pro Lys Pro
                20                  25                  30

Lys Asp Thr Leu Met Ile Ser Arg Thr Pro Glu Val Thr Cys Val Val
            35                  40                  45

Val Asp Val Ser His Glu Asp Pro Glu Val Lys Phe Asn Trp Tyr Val
        50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Asp Tyr Lys Cys Lys Val Ser Asn Lys Ala
            100                 105                 110

Leu Pro Ala Pro Met Gln Lys Thr Ile Ser Lys Ala Lys Gly Gln Pro
        115                 120                 125

Arg Glu Pro Gln Val Tyr Thr Leu Pro Pro Ser Arg Asp Glu Leu Thr
130                 135                 140

Lys Asn Gln Val Ser Leu Thr Cys Leu Val Lys Gly Phe Tyr Pro Arg
145                 150                 155                 160

His Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
210                 215                 220

Ser Leu Ser Leu Ser Pro Gly Lys
225                 230

(2) INFORMATION FOR SEQ ID NO:9:

(i) SEQUENCE CHARACTERISTICS:
      (A) LENGTH: 31 amino acids
      (B) TYPE: amino acid
      (C) STRANDEDNESS: Not Relevant
      (D) TOPOLOGY: linear (ii) MOLECULE TYPE: peptide (iii) HYPOTHETICAL: NO (iv) ANTI-SENSE: NO (vi) ORIGINAL SOURCE:
      (A) ORGANISM: CMV (R2780 Leader)

(ix) FEATURE:
      (D) OTHER INFORMATION: Met1-Arg28 is the actual leader
          peptide; Arg29 strengthens the furin cleavage site;
          nucleotides encoding eThr30 and Ser31 add a SpeI site.

(xi) SEQUENCE DESCRIPTION: SEQ ID NO:9:

Met Ala Arg Arg Leu Trp Ile Leu Ser Leu Leu Ala Val Thr Leu Thr
1               5                   10                  15

```
Val Ala Leu Ala Ala Pro Ser Gln Lys Ser Lys Arg Arg Thr Ser
            20                  25                  30

(2) INFORMATION FOR SEQ ID NO:10:

(i) SEQUENCE CHARACTERISTICS:
        (A) LENGTH: 1630 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (vi) ORIGINAL SOURCE:
        (A) ORGANISM: Mus musculus (vii) IMMEDIATE SOURCE:
        (A) LIBRARY:
        (B) CLONE: RANKL (ix) FEATURE:
        (A) NAME/KEY: CDS
        (B) LOCATION: 3..884

(xi) SEQUENCE DESCRIPTION: SEQ ID NO:10:

CC GGC GTC CCA CAC GAG GGT CCG CTG CAC CCC GCG CCT TCT GCA CCG         47
   Gly Val Pro His Glu Gly Pro Leu His Pro Ala Pro Ser Ala Pro
   1               5                   10                  15

GCT CCG GCG CCG CCA CCC GCC GCC TCC CGC TCC ATG TTC CTG GCC CTC        95
Ala Pro Ala Pro Pro Pro Ala Ala Ser Arg Ser Met Phe Leu Ala Leu
                20                  25                  30

CTG GGG CTG GGA CTG GGC CAG GTG GTC TGC AGC ATC GCT CTG TTC CTG        143
Leu Gly Leu Gly Leu Gly Gln Val Val Cys Ser Ile Ala Leu Phe Leu
            35                  40                  45

TAC TTT CGA GCG CAG ATG GAT CCT AAC AGA ATA TCA GAA GAC AGC ACT        191
Tyr Phe Arg Ala Gln Met Asp Pro Asn Arg Ile Ser Glu Asp Ser Thr
        50                  55                  60

CAC TGC TTT TAT AGA ATC CTG AGA CTC CAT GAA AAC GCA GAT TTG CAG        239
His Cys Phe Tyr Arg Ile Leu Arg Leu His Glu Asn Ala Asp Leu Gln
    65                  70                  75

GAC TCG ACT CTG GAG AGT GAA GAC ACA CTA CCT GAC TCC TGC AGG AGG        287
Asp Ser Thr Leu Glu Ser Glu Asp Thr Leu Pro Asp Ser Cys Arg Arg
80                  85                  90                  95

ATG AAA CAA GCC TTT CAG GGG GCC GTG CAG AAG GAA CTG CAA CAC ATT        335
Met Lys Gln Ala Phe Gln Gly Ala Val Gln Lys Glu Leu Gln His Ile
                100                 105                 110

GTG GGG CCA CAG CGC TTC TCA GGA GCT CCA GCT ATG ATG GAA GGC TCA        383
Val Gly Pro Gln Arg Phe Ser Gly Ala Pro Ala Met Met Glu Gly Ser
            115                 120                 125

TGG TTG GAT GTG GCC CAG CGA GGC AAG CCT GAG GCC CAG CCA TTT GCA        431
Trp Leu Asp Val Ala Gln Arg Gly Lys Pro Glu Ala Gln Pro Phe Ala
        130                 135                 140

CAC CTC ACC ATC AAT GCT GCC AGC ATC CCA TCG GGT TCC CAT AAA GTC        479
His Leu Thr Ile Asn Ala Ala Ser Ile Pro Ser Gly Ser His Lys Val
    145                 150                 155

ACT CTG TCC TCT TGG TAC CAC GAT CGA GGC TGG GCC AAG ATC TCT AAC        527
Thr Leu Ser Ser Trp Tyr His Asp Arg Gly Trp Ala Lys Ile Ser Asn
160                 165                 170                 175

ATG ACG TTA AGC AAC GGA AAA CTA AGG GTT AAC CAA GAT GGC TTC TAT        575
Met Thr Leu Ser Asn Gly Lys Leu Arg Val Asn Gln Asp Gly Phe Tyr
                180                 185                 190
```

```
TAC CTG TAC GCC AAC ATT TGC TTT CGG CAT CAT GAA ACA TCG GGA AGC      623
Tyr Leu Tyr Ala Asn Ile Cys Phe Arg His His Glu Thr Ser Gly Ser
            195                 200                 205

GTA CCT ACA GAC TAT CTT CAG CTG ATG GTG TAT GTC GTT AAA ACC AGC      671
Val Pro Thr Asp Tyr Leu Gln Leu Met Val Tyr Val Val Lys Thr Ser
                210                 215                 220

ATC AAA ATC CCA AGT TCT CAT AAC CTG ATG AAA GGA GGG AGC ACG AAA      719
Ile Lys Ile Pro Ser Ser His Asn Leu Met Lys Gly Gly Ser Thr Lys
    225                 230                 235

AAC TGG TCG GGC AAT TCT GAA TTC CAC TTT TAT TCC ATA AAT GTT GGG      767
Asn Trp Ser Gly Asn Ser Glu Phe His Phe Tyr Ser Ile Asn Val Gly
240                 245                 250                 255

GGA TTT TTC AAG CTC CGA GCT GGT GAA GAA ATT AGC ATT CAG GTG TCC      815
Gly Phe Phe Lys Leu Arg Ala Gly Glu Glu Ile Ser Ile Gln Val Ser
                260                 265                 270

AAC CCT TCC CTG CTG GAT CCG GAT CAA GAT GCG ACG TAC TTT GGG GCT      863
Asn Pro Ser Leu Leu Asp Pro Asp Gln Asp Ala Thr Tyr Phe Gly Ala
            275                 280                 285

TTC AAA GTT CAG GAC ATA GAC TGAGACTCAT TCGTGGAAC ATTAGCATGG           914
Phe Lys Val Gln Asp Ile Asp
            290

ATGTCCTAGA TGTTTGGAAA CTTCTTAAAA AATGGATGAT GTCTATACAT GTGTAAGACT    974

ACTAAGAGAC ATGGCCCACG GTGTATGAAA CTCACAGCCC TCTCTCTTGA GCCTGTACAG   1034

GTTGTGTATA TGTAAAGTCC ATAGGTGATG TTAGATTCAT GGTGATTACA CAACGGTTTT   1094

ACAATTTTGT AATGATTTCC TAGAATTGAA CCAGATTGGG AGAGGTATTC CGATGCTTAT   1154

GAAAAACTTA CACGTGAGCT ATGGAAGGGG GTCACAGTCT CTGGGTCTAA CCCCTGGACA   1214

TGTGCCACTG AGAACCTTGA AATTAAGAGG ATGCCATGTC ATTGCAAAGA AATGATAGTG   1274

TGAAGGGTTA AGTTCTTTTG AATTGTTACA TTGCGCTGGG ACCTGCAAAT AAGTTCTTTT   1334

TTTCTAATGA GGAGAGAAAA ATATATGTAT TTTTATATAA TGTCTAAAGT TATATTTCAG   1394

GTGTAATGTT TTCTGTGCAA AGTTTTGTAA ATTATATTTG TGCTATAGTA TTTGATTCAA   1454

AATATTTAAA AATGTCTCAC TGTTGACATA TTTAATGTTT TAAATGTACA GATGTATTTA   1514

ACTGGTGCAC TTTGTAATTC CCCTGAAGGT ACTCGTAGCT AAGGGGGCAG AATACTGTTT   1574

CTGGTGACCA CATGTAGTTT ATTTCTTTAT TCTTTTTAAC TTAATAGAGT CTTCAG        1630

(2) INFORMATION FOR SEQ ID NO:11:

(i) SEQUENCE CHARACTERISTICS:
        (A) LENGTH: 294 amino acids
        (B) TYPE: amino acid
        (D) TOPOLOGY: linear (ii) MOLECULE TYPE: protein (xi) SEQUENCE DESCRIPTION: SEQ ID NO:11:

Gly Val Pro His Glu Gly Pro Leu His Pro Ala Pro Ser Ala Pro Ala
  1               5                  10                  15

Pro Ala Pro Pro Ala Ala Ser Arg Ser Met Phe Leu Ala Leu Leu
             20                  25                  30

Gly Leu Gly Leu Gly Gln Val Val Cys Ser Ile Ala Leu Phe Leu Tyr
         35                  40                  45

Phe Arg Ala Gln Met Asp Pro Asn Arg Ile Ser Glu Asp Ser Thr His
     50                  55                  60

Cys Phe Tyr Arg Ile Leu Arg Leu His Glu Asn Ala Asp Leu Gln Asp
 65                  70                  75                  80
```

```
Ser Thr Leu Glu Ser Glu Asp Thr Leu Pro Asp Ser Cys Arg Arg Met
             85                  90                  95

Lys Gln Ala Phe Gln Gly Ala Val Gln Lys Glu Leu Gln His Ile Val
            100                 105                 110

Gly Pro Gln Arg Phe Ser Gly Ala Pro Ala Met Met Glu Gly Ser Trp
            115                 120                 125

Leu Asp Val Ala Gln Arg Gly Lys Pro Glu Ala Gln Pro Phe Ala His
    130                 135                 140

Leu Thr Ile Asn Ala Ala Ser Ile Pro Ser Gly Ser His Lys Val Thr
145                 150                 155                 160

Leu Ser Ser Trp Tyr His Asp Arg Gly Trp Ala Lys Ile Ser Asn Met
                165                 170                 175

Thr Leu Ser Asn Gly Lys Leu Arg Val Asn Gln Asp Gly Phe Tyr Tyr
            180                 185                 190

Leu Tyr Ala Asn Ile Cys Phe Arg His His Glu Thr Ser Gly Ser Val
        195                 200                 205

Pro Thr Asp Tyr Leu Gln Leu Met Val Tyr Val Val Lys Thr Ser Ile
    210                 215                 220

Lys Ile Pro Ser Ser His Asn Leu Met Lys Gly Gly Ser Thr Lys Asn
225                 230                 235                 240

Trp Ser Gly Asn Ser Glu Phe His Phe Tyr Ser Ile Asn Val Gly Gly
                245                 250                 255

Phe Phe Lys Leu Arg Ala Gly Glu Glu Ile Ser Ile Gln Val Ser Asn
            260                 265                 270

Pro Ser Leu Leu Asp Pro Asp Gln Asp Ala Thr Tyr Phe Gly Ala Phe
        275                 280                 285

Lys Val Gln Asp Ile Asp
    290
```

(2) INFORMATION FOR SEQ ID NO:12:

(i) SEQUENCE CHARACTERISTICS:
        (A) LENGTH: 954 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (vi) ORIGINAL SOURCE:
        (A) ORGANISM: Homo sapiens (vii) IMMEDIATE SOURCE:
        (A) LIBRARY:
        (B) CLONE: huRANKL (full length)

(ix) FEATURE:
        (A) NAME/KEY: CDS
        (B) LOCATION: 1..951

(xi) SEQUENCE DESCRIPTION: SEQ ID NO:12:

```
ATG CGC CGC GCC AGC AGA GAC TAC ACC AAG TAC CTG CGT GGC TCG GAG        48
Met Arg Arg Ala Ser Arg Asp Tyr Thr Lys Tyr Leu Arg Gly Ser Glu
 1               5                  10                  15

GAG ATG GGC GGC GGC CCC GGA GCC CCG CAC GAG GGC CCC CTG CAC GCC        96
Glu Met Gly Gly Gly Pro Gly Ala Pro His Glu Gly Pro Leu His Ala
            20                  25                  30
```

-continued

| | | |
|---|---|---|
| CCG CCG CCG CCT GCG CCG CAC CAG CCC CCC GCC GCC TCC CGC TCC ATG<br>Pro Pro Pro Pro Ala Pro His Gln Pro Pro Ala Ala Ser Arg Ser Met<br>             35                     40                     45 | 144 |
| TTC GTG GCC CTC CTG GGG CTG GGG CTG GGC CAG GTT GTC TGC AGC GTC<br>Phe Val Ala Leu Leu Gly Leu Gly Leu Gly Gln Val Val Cys Ser Val<br>   50                    55                    60 | 192 |
| GCC CTG TTC TTC TAT TTC AGA GCG CAG ATG GAT CCT AAT AGA ATA TCA<br>Ala Leu Phe Phe Tyr Phe Arg Ala Gln Met Asp Pro Asn Arg Ile Ser<br>65                    70                     75                    80 | 240 |
| GAA GAT GGC ACT CAC TGC ATT TAT AGA ATT TTG AGA CTC CAT GAA AAT<br>Glu Asp Gly Thr His Cys Ile Tyr Arg Ile Leu Arg Leu His Glu Asn<br>             85                     90                    95 | 288 |
| GCA GAT TTT CAA GAC ACA ACT CTG GAG AGT CAA GAT ACA AAA TTA ATA<br>Ala Asp Phe Gln Asp Thr Thr Leu Glu Ser Gln Asp Thr Lys Leu Ile<br>                    100                  105                110 | 336 |
| CCT GAT TCA TGT AGG AGA ATT AAA CAG GCC TTT CAA GGA GCT GTG CAA<br>Pro Asp Ser Cys Arg Arg Ile Lys Gln Ala Phe Gln Gly Ala Val Gln<br>             115                  120                125 | 384 |
| AAG GAA TTA CAA CAT ATC GTT GGA TCA CAG CAC ATC AGA GCA GAG AAA<br>Lys Glu Leu Gln His Ile Val Gly Ser Gln His Ile Arg Ala Glu Lys<br>130                    135                  140 | 432 |
| GCG ATG GTG GAT GGC TCA TGG TTA GAT CTG GCC AAG AGG AGC AAG CTT<br>Ala Met Val Asp Gly Ser Trp Leu Asp Leu Ala Lys Arg Ser Lys Leu<br>145                    150                  155                160 | 480 |
| GAA GCT CAG CCT TTT GCT CAT CTC ACT ATT AAT GCC ACC GAC ATC CCA<br>Glu Ala Gln Pro Phe Ala His Leu Thr Ile Asn Ala Thr Asp Ile Pro<br>             165                  170                175 | 528 |
| TCT GGT TCC CAT AAA GTG AGT CTG TCC TCT TGG TAC CAT GAT CGG GGT<br>Ser Gly Ser His Lys Val Ser Leu Ser Ser Trp Tyr His Asp Arg Gly<br>                    180                  185                190 | 576 |
| TGG GCC AAG ATC TCC AAC ATG ACT TTT AGC AAT GGA AAA CTA ATA GTT<br>Trp Ala Lys Ile Ser Asn Met Thr Phe Ser Asn Gly Lys Leu Ile Val<br>             195                  200                205 | 624 |
| AAT CAG GAT GGC TTT TAT TAC CTG TAT GCC AAC ATT TGC TTT CGA CAT<br>Asn Gln Asp Gly Phe Tyr Tyr Leu Tyr Ala Asn Ile Cys Phe Arg His<br>210                    215                  220 | 672 |
| CAT GAA ACT TCA GGA GAC CTA GCT ACA GAG TAT CTT CAA CTA ATG GTG<br>His Glu Thr Ser Gly Asp Leu Ala Thr Glu Tyr Leu Gln Leu Met Val<br>225                    230                  235                240 | 720 |
| TAC GTC ACT AAA ACC AGC ATC AAA ATC CCA AGT TCT CAT ACC CTG ATG<br>Tyr Val Thr Lys Thr Ser Ile Lys Ile Pro Ser Ser His Thr Leu Met<br>             245                  250                255 | 768 |
| AAA GGA GGA AGC ACC AAG TAT TGG TCA GGG AAT TCT GAA TTC CAT TTT<br>Lys Gly Gly Ser Thr Lys Tyr Trp Ser Gly Asn Ser Glu Phe His Phe<br>                    260                  265                270 | 816 |
| TAT TCC ATA AAC GTT GGT GGA TTT TTT AAG TTA CGG TCT GGA GAG GAA<br>Tyr Ser Ile Asn Val Gly Gly Phe Phe Lys Leu Arg Ser Gly Glu Glu<br>             275                  280                285 | 864 |
| ATC AGC ATC GAG GTC TCC AAC CCC TCC TTA CTG GAT CCG GAT CAG GAT<br>Ile Ser Ile Glu Val Ser Asn Pro Ser Leu Leu Asp Pro Asp Gln Asp<br>290                    295                  300 | 912 |
| GCA ACA TAC TTT GGG GCT TTT AAA GTT CGA GAT ATA GAT TGA<br>Ala Thr Tyr Phe Gly Ala Phe Lys Val Arg Asp Ile Asp<br>305                    310                  315 | 954 |

(2) INFORMATION FOR SEQ ID NO:13:

(i) SEQUENCE CHARACTERISTICS:
        (A) LENGTH: 317 amino acids
        (B) TYPE: amino acid
        (D) TOPOLOGY: linear (ii) MOLECULE TYPE: protein (xi) SEQUENCE DESCRIPTION: SEQ ID NO:13:

| Met | Arg | Arg | Ala | Ser | Arg | Asp | Tyr | Thr | Lys | Tyr | Leu | Arg | Gly | Ser | Glu |
|---|---|---|---|---|---|---|---|---|---|---|---|---|---|---|---|
| 1 | | | | 5 | | | | | 10 | | | | | 15 | |

| Glu | Met | Gly | Gly | Gly | Pro | Gly | Ala | Pro | His | Glu | Gly | Pro | Leu | His | Ala |
|---|---|---|---|---|---|---|---|---|---|---|---|---|---|---|---|
| | | | 20 | | | | | 25 | | | | | 30 | | |

| Pro | Pro | Pro | Pro | Ala | Pro | His | Gln | Pro | Pro | Ala | Ala | Ser | Arg | Ser | Met |
|---|---|---|---|---|---|---|---|---|---|---|---|---|---|---|---|
| | | | 35 | | | | | 40 | | | | | 45 | | |

| Phe | Val | Ala | Leu | Leu | Gly | Leu | Gly | Leu | Gly | Gln | Val | Val | Cys | Ser | Val |
|---|---|---|---|---|---|---|---|---|---|---|---|---|---|---|---|
| | 50 | | | | | 55 | | | | | 60 | | | | |

| Ala | Leu | Phe | Phe | Tyr | Phe | Arg | Ala | Gln | Met | Asp | Pro | Asn | Arg | Ile | Ser |
|---|---|---|---|---|---|---|---|---|---|---|---|---|---|---|---|
| 65 | | | | | 70 | | | | | 75 | | | | | 80 |

| Glu | Asp | Gly | Thr | His | Cys | Ile | Tyr | Arg | Ile | Leu | Arg | Leu | His | Glu | Asn |
|---|---|---|---|---|---|---|---|---|---|---|---|---|---|---|---|
| | | | | 85 | | | | | 90 | | | | | 95 | |

| Ala | Asp | Phe | Gln | Asp | Thr | Thr | Leu | Glu | Ser | Gln | Asp | Thr | Lys | Leu | Ile |
|---|---|---|---|---|---|---|---|---|---|---|---|---|---|---|---|
| | | | 100 | | | | | 105 | | | | | 110 | | |

| Pro | Asp | Ser | Cys | Arg | Arg | Ile | Lys | Gln | Ala | Phe | Gln | Gly | Ala | Val | Gln |
|---|---|---|---|---|---|---|---|---|---|---|---|---|---|---|---|
| | | | 115 | | | | | 120 | | | | | 125 | | |

| Lys | Glu | Leu | Gln | His | Ile | Val | Gly | Ser | Gln | His | Ile | Arg | Ala | Glu | Lys |
|---|---|---|---|---|---|---|---|---|---|---|---|---|---|---|---|
| 130 | | | | | 135 | | | | | 140 | | | | | |

| Ala | Met | Val | Asp | Gly | Ser | Trp | Leu | Asp | Leu | Ala | Lys | Arg | Ser | Lys | Leu |
|---|---|---|---|---|---|---|---|---|---|---|---|---|---|---|---|
| 145 | | | | | 150 | | | | | 155 | | | | | 160 |

| Glu | Ala | Gln | Pro | Phe | Ala | His | Leu | Thr | Ile | Asn | Ala | Thr | Asp | Ile | Pro |
|---|---|---|---|---|---|---|---|---|---|---|---|---|---|---|---|
| | | | | 165 | | | | | 170 | | | | | 175 | |

| Ser | Gly | Ser | His | Lys | Val | Ser | Leu | Ser | Ser | Trp | Tyr | His | Asp | Arg | Gly |
|---|---|---|---|---|---|---|---|---|---|---|---|---|---|---|---|
| | | | 180 | | | | | 185 | | | | | 190 | | |

| Trp | Ala | Lys | Ile | Ser | Asn | Met | Thr | Phe | Ser | Asn | Gly | Lys | Leu | Ile | Val |
|---|---|---|---|---|---|---|---|---|---|---|---|---|---|---|---|
| | | | 195 | | | | | 200 | | | | | 205 | | |

| Asn | Gln | Asp | Gly | Phe | Tyr | Tyr | Leu | Tyr | Ala | Asn | Ile | Cys | Phe | Arg | His |
|---|---|---|---|---|---|---|---|---|---|---|---|---|---|---|---|
| | 210 | | | | | 215 | | | | | 220 | | | | |

| His | Glu | Thr | Ser | Gly | Asp | Leu | Ala | Thr | Glu | Tyr | Leu | Gln | Leu | Met | Val |
|---|---|---|---|---|---|---|---|---|---|---|---|---|---|---|---|
| 225 | | | | | 230 | | | | | 235 | | | | | 240 |

| Tyr | Val | Thr | Lys | Thr | Ser | Ile | Lys | Ile | Pro | Ser | Ser | His | Thr | Leu | Met |
|---|---|---|---|---|---|---|---|---|---|---|---|---|---|---|---|
| | | | | 245 | | | | | 250 | | | | | 255 | |

| Lys | Gly | Gly | Ser | Thr | Lys | Tyr | Trp | Ser | Gly | Asn | Ser | Glu | Phe | His | Phe |
|---|---|---|---|---|---|---|---|---|---|---|---|---|---|---|---|
| | | | 260 | | | | | 265 | | | | | 270 | | |

| Tyr | Ser | Ile | Asn | Val | Gly | Gly | Phe | Phe | Lys | Leu | Arg | Ser | Gly | Glu | Glu |
|---|---|---|---|---|---|---|---|---|---|---|---|---|---|---|---|
| | | 275 | | | | | 280 | | | | | 285 | | | |

| Ile | Ser | Ile | Glu | Val | Ser | Asn | Pro | Ser | Leu | Leu | Asp | Pro | Asp | Gln | Asp |
|---|---|---|---|---|---|---|---|---|---|---|---|---|---|---|---|
| | 290 | | | | | 295 | | | | | 300 | | | | |

| Ala | Thr | Tyr | Phe | Gly | Ala | Phe | Lys | Val | Arg | Asp | Ile | Asp | | | |
|---|---|---|---|---|---|---|---|---|---|---|---|---|---|---|---|
| 305 | | | | | 310 | | | | | 315 | | | | | |

(2) INFORMATION FOR SEQ ID NO:14:

(i) SEQUENCE CHARACTERISTICS:
        (A) LENGTH: 1878 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (vi) ORIGINAL SOURCE:
  (A) ORGANISM: Murine (vii) IMMEDIATE SOURCE:
  (A) LIBRARY: Murine Fetal Liver Epithelium
  (B) CLONE: muRANK (ix) FEATURE:
  (A) NAME/KEY: CDS
  (B) LOCATION: 1..1875

(xi) SEQUENCE DESCRIPTION: SEQ ID NO:14:

```
ATG GCC CCG CGC GCC CGG CGG CGC CGC CAG CTG CCC GCG CCG CTG CTG      48
Met Ala Pro Arg Ala Arg Arg Arg Arg Gln Leu Pro Ala Pro Leu Leu
 1               5                  10                  15

GCG CTC TGC GTG CTG CTC GTT CCA CTG CAG GTG ACT CTC CAG GTC ACT      96
Ala Leu Cys Val Leu Leu Val Pro Leu Gln Val Thr Leu Gln Val Thr
             20                  25                  30

CCT CCA TGC ACC CAG GAG AGG CAT TAT GAG CAT CTC GGA CGG TGT TGC     144
Pro Pro Cys Thr Gln Glu Arg His Tyr Glu His Leu Gly Arg Cys Cys
         35                  40                  45

AGC AGA TGC GAA CCA GGA AAG TAC CTG TCC TCT AAG TGC ACT CCT ACC     192
Ser Arg Cys Glu Pro Gly Lys Tyr Leu Ser Ser Lys Cys Thr Pro Thr
     50                  55                  60

TCC GAC AGT GTG TGT CTG CCC TGT GGC CCC GAT GAG TAC TTG GAC ACC     240
Ser Asp Ser Val Cys Leu Pro Cys Gly Pro Asp Glu Tyr Leu Asp Thr
 65                  70                  75                  80

TGG AAT GAA GAA GAT AAA TGC TTG CTG CAT AAA GTC TGT GAT GCA GGC     288
Trp Asn Glu Glu Asp Lys Cys Leu Leu His Lys Val Cys Asp Ala Gly
                 85                  90                  95

AAG GCC CTG GTG GCG GTG GAT CCT GGC AAC CAC ACG GCC CCG CGT CGC     336
Lys Ala Leu Val Ala Val Asp Pro Gly Asn His Thr Ala Pro Arg Arg
            100                 105                 110

TGT GCT TGC ACG GCT GGC TAC CAC TGG AAC TCA GAC TGC GAG TGC TGC     384
Cys Ala Cys Thr Ala Gly Tyr His Trp Asn Ser Asp Cys Glu Cys Cys
        115                 120                 125

CGC AGG AAC ACG GAG TGT GCA CCT GGC TTC GGA GCT CAG CAT CCC TTG     432
Arg Arg Asn Thr Glu Cys Ala Pro Gly Phe Gly Ala Gln His Pro Leu
    130                 135                 140

CAG CTC AAC AAG GAT ACG GTG TGC ACA CCC TGC CTC CTG GGC TTC TTC     480
Gln Leu Asn Lys Asp Thr Val Cys Thr Pro Cys Leu Leu Gly Phe Phe
145                 150                 155                 160

TCA GAT GTC TTT TCG TCC ACA GAC AAA TGC AAA CCT TGG ACC AAC TGC     528
Ser Asp Val Phe Ser Ser Thr Asp Lys Cys Lys Pro Trp Thr Asn Cys
                165                 170                 175

ACC CTC CTT GGA AAG CTA GAA GCA CAC CAG GGG ACA ACG GAA TCA GAT     576
Thr Leu Leu Gly Lys Leu Glu Ala His Gln Gly Thr Thr Glu Ser Asp
            180                 185                 190

GTG GTC TGC AGC TCT TCC ATG ACA CTG AGG AGA CCA CCC AAG GAG GCC     624
Val Val Cys Ser Ser Ser Met Thr Leu Arg Arg Pro Pro Lys Glu Ala
        195                 200                 205

CAG GCT TAC CTG CCC AGT CTC ATC GTT CTG CTC CTC TTC ATC TCT GTG     672
Gln Ala Tyr Leu Pro Ser Leu Ile Val Leu Leu Leu Phe Ile Ser Val
    210                 215                 220

GTA GTA GTG GCT GCC ATC ATC TTC GGC GTT TAC TAC AGG AAG GGA GGG     720
Val Val Val Ala Ala Ile Ile Phe Gly Val Tyr Tyr Arg Lys Gly Gly
225                 230                 235                 240

AAA GCG CTG ACA GCT AAT TTG TGG AAT TGG GTC AAT GAT GCT TGC AGT     768
Lys Ala Leu Thr Ala Asn Leu Trp Asn Trp Val Asn Asp Ala Cys Ser
                245                 250                 255

AGT CTA AGT GGA AAT AAG GAG TCC TCA GGG GAC CGT TGT GCT GGT TCC     816
```

-continued

```
                Ser Leu Ser Gly Asn Lys Glu Ser Ser Gly Asp Arg Cys Ala Gly Ser
                            260                 265                 270

CAC TCG GCA ACC TCC AGT CAG CAA GAA GTG TGT GAA GGT ATC TTA CTA           864
His Ser Ala Thr Ser Ser Gln Gln Glu Val Cys Glu Gly Ile Leu Leu
            275                 280                 285

ATG ACT CGG GAG GAG AAG ATG GTT CCA GAA GAC GGT GCT GGA GTC TGT           912
Met Thr Arg Glu Glu Lys Met Val Pro Glu Asp Gly Ala Gly Val Cys
290                 295                 300

GGG CCT GTG TGT GCG GCA GGT GGG CCC TGG GCA GAA GTC AGA GAT TCT           960
Gly Pro Val Cys Ala Ala Gly Gly Pro Trp Ala Glu Val Arg Asp Ser
305                 310                 315                 320

AGG ACG TTC ACA CTG GTC AGC GAG GTT GAG ACG CAA GGA GAC CTC TCG          1008
Arg Thr Phe Thr Leu Val Ser Glu Val Glu Thr Gln Gly Asp Leu Ser
                325                 330                 335

AGG AAG ATT CCC ACA GAG GAT GAG TAC ACG GAC CGG CCC TCG CAG CCT          1056
Arg Lys Ile Pro Thr Glu Asp Glu Tyr Thr Asp Arg Pro Ser Gln Pro
            340                 345                 350

TCG ACT GGT TCA CTG CTC CTA ATC CAG CAG GGA AGC AAA TCT ATA CCC          1104
Ser Thr Gly Ser Leu Leu Leu Ile Gln Gln Gly Ser Lys Ser Ile Pro
        355                 360                 365

CCA TTC CAG GAG CCC CTG GAA GTG GGG GAG AAC GAC AGT TTA AGC CAG          1152
Pro Phe Gln Glu Pro Leu Glu Val Gly Glu Asn Asp Ser Leu Ser Gln
    370                 375                 380

TGT TTC ACC GGG ACT GAA AGC ACG GTG GAT TCT GAG GGC TGT GAC TTC          1200
Cys Phe Thr Gly Thr Glu Ser Thr Val Asp Ser Glu Gly Cys Asp Phe
385                 390                 395                 400

ACT GAG CCT CCG AGC AGA ACT GAC TCT ATG CCC GTG TCC CCT GAA AAG          1248
Thr Glu Pro Pro Ser Arg Thr Asp Ser Met Pro Val Ser Pro Glu Lys
                405                 410                 415

CAC CTG ACA AAA GAA ATA GAA GGT GAC AGT TGC CTC CCC TGG GTG GTC          1296
His Leu Thr Lys Glu Ile Glu Gly Asp Ser Cys Leu Pro Trp Val Val
            420                 425                 430

AGC TCC AAC TCA ACA GAT GGC TAC ACA GGC AGT GGG AAC ACT CCT GGG          1344
Ser Ser Asn Ser Thr Asp Gly Tyr Thr Gly Ser Gly Asn Thr Pro Gly
        435                 440                 445

GAG GAC CAT GAA CCC TTT CCA GGG TCC CTG AAA TGT GGA CCA TTG CCC          1392
Glu Asp His Glu Pro Phe Pro Gly Ser Leu Lys Cys Gly Pro Leu Pro
    450                 455                 460

CAG TGT GCC TAC AGC ATG GGC TTT CCC AGT GAA GCA GCA GCC AGC ATG          1440
Gln Cys Ala Tyr Ser Met Gly Phe Pro Ser Glu Ala Ala Ala Ser Met
465                 470                 475                 480

GCA GAG GCG GGA GTA CGG CCC CAG GAC AGG GCT GAT GAG AGG GGA GCC          1488
Ala Glu Ala Gly Val Arg Pro Gln Asp Arg Ala Asp Glu Arg Gly Ala
                485                 490                 495

TCA GGG TCC GGG AGC TCC CCC AGT GAC CAG CCA CCT GCC TCT GGG AAC          1536
Ser Gly Ser Gly Ser Ser Pro Ser Asp Gln Pro Pro Ala Ser Gly Asn
            500                 505                 510

GTG ACT GGA AAC AGT AAC TCC ACG TTC ATC TCT AGC GGG CAG GTG ATG          1584
Val Thr Gly Asn Ser Asn Ser Thr Phe Ile Ser Ser Gly Gln Val Met
        515                 520                 525

AAC TTC AAG GGT GAC ATC ATC GTG GTG TAT GTC AGC CAG ACC TCG CAG          1632
Asn Phe Lys Gly Asp Ile Ile Val Val Tyr Val Ser Gln Thr Ser Gln
    530                 535                 540

GAG GGC CCG GGT TCC GCA GAG CCC GAG TCG GAG CCC GTG GGC CGC CCT          1680
Glu Gly Pro Gly Ser Ala Glu Pro Glu Ser Glu Pro Val Gly Arg Pro
545                 550                 555                 560

GTG CAG GAG GAG ACG CTG GCA CAC AGA GAC TCC TTT GCG GGC ACC GCG          1728
Val Gln Glu Glu Thr Leu Ala His Arg Asp Ser Phe Ala Gly Thr Ala
                565                 570                 575
```

```
CCG CGC TTC CCC GAC GTC TGT GCC ACC GGG GCT GGG CTG CAG GAG CAG     1776
Pro Arg Phe Pro Asp Val Cys Ala Thr Gly Ala Gly Leu Gln Glu Gln
        580                     585                 590

GGG GCA CCC CGG CAG AAG GAC GGG ACA TCG CGG CCG GTG CAG GAG CAG     1824
Gly Ala Pro Arg Gln Lys Asp Gly Thr Ser Arg Pro Val Gln Glu Gln
            595                 600                 605

GGT GGG GCG CAG ACT TCA CTC CAT ACC CAG GGG TCC GGA CAA TGT GCA     1872
Gly Gly Ala Gln Thr Ser Leu His Thr Gln Gly Ser Gly Gln Cys Ala
610                 615                 620

GAA TGA                                                             1878
Glu
625

(2) INFORMATION FOR SEQ ID NO:15:

(i) SEQUENCE CHARACTERISTICS:
        (A) LENGTH: 625 amino acids
        (B) TYPE: amino acid
        (D) TOPOLOGY: linear (ii) MOLECULE TYPE: protein (xi) SEQUENCE DESCRIPTION: SEQ ID NO:15:

Met Ala Pro Arg Ala Arg Arg Arg Gln Leu Pro Ala Pro Leu Leu
1               5                   10                  15

Ala Leu Cys Val Leu Leu Val Pro Leu Gln Val Thr Leu Gln Val Thr
                20                  25                  30

Pro Pro Cys Thr Gln Glu Arg His Tyr Glu His Leu Gly Arg Cys Cys
            35                  40                  45

Ser Arg Cys Glu Pro Gly Lys Tyr Leu Ser Ser Lys Cys Thr Pro Thr
        50                  55                  60

Ser Asp Ser Val Cys Leu Pro Cys Gly Pro Asp Glu Tyr Leu Asp Thr
65                  70                  75                  80

Trp Asn Glu Glu Asp Lys Cys Leu Leu His Lys Val Cys Asp Ala Gly
                85                  90                  95

Lys Ala Leu Val Ala Val Asp Pro Gly Asn His Thr Ala Pro Arg Arg
            100                 105                 110

Cys Ala Cys Thr Ala Gly Tyr His Trp Asn Ser Asp Cys Glu Cys Cys
        115                 120                 125

Arg Arg Asn Thr Glu Cys Ala Pro Gly Phe Gly Ala Gln His Pro Leu
130                 135                 140

Gln Leu Asn Lys Asp Thr Val Cys Thr Pro Cys Leu Leu Gly Phe Phe
145                 150                 155                 160

Ser Asp Val Phe Ser Ser Thr Asp Lys Cys Lys Pro Trp Thr Asn Cys
                165                 170                 175

Thr Leu Leu Gly Lys Leu Glu Ala His Gln Gly Thr Thr Glu Ser Asp
            180                 185                 190

Val Val Cys Ser Ser Ser Met Thr Leu Arg Arg Pro Pro Lys Glu Ala
        195                 200                 205

Gln Ala Tyr Leu Pro Ser Leu Ile Val Leu Leu Phe Ile Ser Val
210                 215                 220

Val Val Val Ala Ala Ile Ile Phe Gly Val Tyr Tyr Arg Lys Gly Gly
225                 230                 235                 240

Lys Ala Leu Thr Ala Asn Leu Trp Asn Trp Val Asn Asp Ala Cys Ser
                245                 250                 255

Ser Leu Ser Gly Asn Lys Glu Ser Ser Gly Asp Arg Cys Ala Gly Ser
            260                 265                 270
```

-continued

```
His Ser Ala Thr Ser Ser Gln Gln Glu Val Cys Glu Gly Ile Leu Leu
        275                 280                 285
Met Thr Arg Glu Glu Lys Met Val Pro Glu Asp Gly Ala Gly Val Cys
290                 295                 300
Gly Pro Val Cys Ala Ala Gly Gly Pro Trp Ala Glu Val Arg Asp Ser
305                 310                 315                 320
Arg Thr Phe Thr Leu Val Ser Glu Val Glu Thr Gln Gly Asp Leu Ser
                325                 330                 335
Arg Lys Ile Pro Thr Glu Asp Glu Tyr Thr Asp Arg Pro Ser Gln Pro
            340                 345                 350
Ser Thr Gly Ser Leu Leu Ile Gln Gln Gly Ser Lys Ser Ile Pro
        355                 360                 365
Pro Phe Gln Glu Pro Leu Glu Val Gly Glu Asn Asp Ser Leu Ser Gln
370                 375                 380
Cys Phe Thr Gly Thr Glu Ser Thr Val Asp Ser Glu Gly Cys Asp Phe
385                 390                 395                 400
Thr Glu Pro Pro Ser Arg Thr Asp Ser Met Pro Val Ser Pro Glu Lys
                405                 410                 415
His Leu Thr Lys Glu Ile Glu Gly Asp Ser Cys Leu Pro Trp Val Val
            420                 425                 430
Ser Ser Asn Ser Thr Asp Gly Tyr Thr Gly Ser Gly Asn Thr Pro Gly
        435                 440                 445
Glu Asp His Glu Pro Phe Pro Gly Ser Leu Lys Cys Gly Pro Leu Pro
450                 455                 460
Gln Cys Ala Tyr Ser Met Gly Phe Pro Ser Glu Ala Ala Ala Ser Met
465                 470                 475                 480
Ala Glu Ala Gly Val Arg Pro Gln Asp Arg Ala Asp Glu Arg Gly Ala
                485                 490                 495
Ser Gly Ser Gly Ser Ser Pro Ser Asp Gln Pro Pro Ala Ser Gly Asn
            500                 505                 510
Val Thr Gly Asn Ser Asn Ser Thr Phe Ile Ser Ser Gly Gln Val Met
        515                 520                 525
Asn Phe Lys Gly Asp Ile Ile Val Val Tyr Val Ser Gln Thr Ser Gln
530                 535                 540
Glu Gly Pro Gly Ser Ala Glu Pro Glu Ser Glu Pro Val Gly Arg Pro
545                 550                 555                 560
Val Gln Glu Glu Thr Leu Ala His Arg Asp Ser Phe Ala Gly Thr Ala
                565                 570                 575
Pro Arg Phe Pro Asp Val Cys Ala Thr Gly Ala Gly Leu Gln Glu Gln
            580                 585                 590
Gly Ala Pro Arg Gln Lys Asp Gly Thr Ser Arg Pro Val Gln Glu Gln
        595                 600                 605
Gly Gly Ala Gln Thr Ser Leu His Thr Gln Gly Ser Gly Gln Cys Ala
610                 615                 620
Glu
625
```

(2) INFORMATION FOR SEQ ID NO:16:

(i) SEQUENCE CHARACTERISTICS:
      (A) LENGTH: 20 amino acids
      (B) TYPE: amino acid
      (D) TOPOLOGY: linear (ii) MOLECULE TYPE: protein -continued

```
(xi) SEQUENCE DESCRIPTION: SEQ ID NO:16:

Met Glu Thr Asp Thr Leu Leu Leu Trp Val Leu Leu Leu Trp Val Pro
  1               5                  10                  15

Gly Ser Thr Gly
            20

(2) INFORMATION FOR SEQ ID NO:17:

(i) SEQUENCE CHARACTERISTICS:
        (A) LENGTH: 5 amino acids
        (B) TYPE: amino acid
        (D) TOPOLOGY: linear (ii) MOLECULE TYPE: protein (xi) SEQUENCE DESCRIPTION: SEQ ID NO:17:

Asp Tyr Lys Asp Glu
                  5

(2) INFORMATION FOR SEQ ID NO:18:

(i) SEQUENCE CHARACTERISTICS:
        (A) LENGTH: 6 amino acids
        (B) TYPE: amino acid
        (D) TOPOLOGY: linear (ii) MOLECULE TYPE: protein (xi) SEQUENCE DESCRIPTION: SEQ ID NO:18:

His His His His His His
                      5

(2) INFORMATION FOR SEQ ID NO:19:

(i) SEQUENCE CHARACTERISTICS:
        (A) LENGTH: 33 amino acids
        (B) TYPE: amino acid
        (D) TOPOLOGY: linear (ii) MOLECULE TYPE: protein (xi) SEQUENCE DESCRIPTION: SEQ ID NO:19:

Arg Met Lys Gln Ile Glu Asp Lys Ile Glu Glu Ile Leu Ser Lys Ile
  1               5                  10                  15

Tyr His Ile Glu Asn Glu Ile Ala Arg Ile Lys Lys Leu Ile Gly Glu
                 20                  25                  30

Arg
```